United States Patent
Jakobi et al.

(10) Patent No.: US 10,743,540 B2
(45) Date of Patent: Aug. 18, 2020

(54) 3-AMINO-1,2,4-TRIAZINE DERIVATIVES AND THEIR USE FOR CONTROLLING UNDESIRED PLANT GROWTH

(71) Applicant: BAYER CROPSCIENCE AKTIENGESELLSCHAFT, Monheim am Rhein (DE)

(72) Inventors: Harald Jakobi, Frankfurt (DE); Klemens Minn, Hattersheim (DE); Estella Buscató Arsequell, Frankfurt am Main (DE); Hansjörg Dietrich, Liederbach am Taunus (DE); Elmar Gatzweiler, Bad Nauheim (DE); Christopher Hugh Rosinger, Hofheim (DE); Anu Bheemaiah Machettira, Frankfurt am Main (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/312,095

(22) PCT Filed: Jun. 19, 2017

(86) PCT No.: PCT/EP2017/064889
§ 371 (c)(1),
(2) Date: Dec. 20, 2018

(87) PCT Pub. No.: WO2017/220467
PCT Pub. Date: Dec. 28, 2017

(65) Prior Publication Data
US 2019/0230927 A1    Aug. 1, 2019

(30) Foreign Application Priority Data
Jun. 24, 2016 (EP) .................................. 16176110

(51) Int. Cl.
| | | |
|---|---|---|
| A01N 43/707 | (2006.01) |
| C07D 253/07 | (2006.01) |
| C07D 253/075 | (2006.01) |
| C07D 405/12 | (2006.01) |
| C07D 249/14 | (2006.01) |

(52) U.S. Cl.
CPC ......... *A01N 43/707* (2013.01); *C07D 249/14* (2013.01); *C07D 253/07* (2013.01); *C07D 253/075* (2013.01); *C07D 405/12* (2013.01)

(58) Field of Classification Search
CPC . A01N 43/707; C07D 253/07; C07D 253/075
See application file for complete search history.

(56) References Cited

U.S. PATENT DOCUMENTS

| | | |
|---|---|---|
| 8,114,991 B2 | 2/2012 | Ahrens et al. |
| 9,375,002 B2 | 6/2016 | Minn et al. |
| 2004/0157739 A1 | 8/2004 | Ahrens et al. |
| 2012/0101287 A1 | 4/2012 | Ahrens et al. |
| 2015/0094205 A1 | 4/2015 | Minn et al. |

FOREIGN PATENT DOCUMENTS

| | | |
|---|---|---|
| WO | 2004/069814 A1 | 8/2004 |
| WO | 2013/144187 A1 | 10/2013 |

OTHER PUBLICATIONS

International Search Report of International Patent Application No. PCT/EP2017/064889 dated Jul. 26, 2017.

*Primary Examiner* — Brenda L Coleman
(74) *Attorney, Agent, or Firm* — McBee Moore & Vanik IP, LLC

(57) ABSTRACT

The invention relates to compounds of general formula (I), to the agrochemically compatible salts thereof, to a method for the production thereof and to the use thereof in the field of plant protection.

20 Claims, No Drawings

3-AMINO-1,2,4-TRIAZINE DERIVATIVES AND THEIR USE FOR CONTROLLING UNDESIRED PLANT GROWTH

CROSS-REFERENCE TO RELATED APPLICATIONS

This application is a National Stage entry of International Application No. PCT/EP2017/064889, filed 19 Jun. 2017, which claims priority to European Patent Application No. 16176110.1, filed 24 Jun. 2016.

BACKGROUND

Field

The invention relates to the technical field of crop protection compositions, particularly to that of herbicides for selective control of broad-leaved weeds and weed grasses in crops of useful plants and in the ornamental garden sector and for general control of broad-leaved weeds and weed grasses in areas of the environment where plant growth is disruptive.

More particularly, the invention relates to substituted 3-amino-1,2,4-triazine derivatives, to processes for their preparation and to their use for control of harmful plants.

Description of Related Art

The compounds of the formula (I) according to the invention have, in the 3 position of the 1,2,4-triazine, a partially hydrogenated bicyclic substituent attached via an amine to the aromatic system in the alpha position, where the triazine may also be substituted in the 5 position and 6 position and the amine substituent $R^1$ together with the substituent in the adjacent position ($R^2$) may form a ring.

The prior art does not disclose the herbicidal action of such 1,2,4-triazines.

The use of the known selective herbicides for control of harmful plants or as plant growth regulators in various crops of useful plants frequently entails an application rate that incurs high costs or results in unwanted damage to the useful plants. Moreover, in many cases, the use of the active compounds is uneconomic owing to comparatively high production costs.

It is therefore desirable to provide alternative chemical active compounds which can be used as herbicides or plant growth regulators and which are associated with certain advantages compared to systems known from the prior art.

SUMMARY

It is an object of the present invention to provide alternative active compounds which can be used as herbicides or plant growth regulators, having satisfactory herbicidal action and a broad spectrum of activity against harmful plants and/or having high selectivity in crops of useful plants.

The object is achieved by means of specifically substituted 3-amino-1,2,4-triazine derivatives of the formula (I) as claimed in claim 1, which can advantageously be used as herbicides and also as plant growth regulators.

Accordingly, the present invention provides compounds of the formula (I)

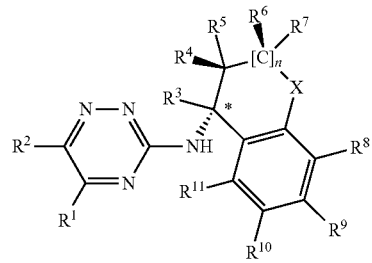

and the agrochemically acceptable salts thereof in which represents hydrogen, amino, hydrazino, hydroxyamino, ($(C_1-C_6)$-alkyl)-amino, ($(C_3-C_6)$-cycloalkyl)-amino, di-($(C_1-C_6)$-alkyl)-amino, $(C_1-C_6)$-alkylcarbonylamino and bis-($(C_1-C_6)$-alkyl)-carbonylamino;

$R^2$ is selected from the group consisting of
- hydrogen, halogen, hydroxy, nitro, amino, cyano, C(O)OH, C(O)NH$_2$;
- $(C_1-C_6)$-alkyl, $(C_1-C_6)$-haloalkyl, $(C_1-C_6)$-alkylcarbonyl, $(C_1-C_6)$-haloalkylcarbonyl, $(C_1-C_6)$-alkylcarbonyloxy, $(C_1-C_6)$-haloalkylcarbonyloxy, $(C_1-C_6)$-alkylcarbonyl-$(C_1-C_4)$-alkyl;
- $(C_1-C_6)$-alkoxy, $(C_1-C_6)$-haloalkoxy, $(C_1-C_6)$-alkoxycarbonyl, $(C_1-C_6)$-haloalkoxycarbonyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl;
- $(C_2-C_6)$-alkenyl, $(C_2-C_6)$-haloalkenyl, $(C_2-C_6)$-alkenylcarbonyl, $(C_2-C_6)$-haloalkenylcarbonyl, $(C_2-C_6)$-alkenyloxy, $(C_2-C_6)$-haloalkenyloxy, $(C_2-C_6)$-alkenyloxycarbonyl, $(C_2-C_6)$-haloalkenyloxycarbonyl;
- $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl;
- tri-$(C_1-C_6)$-alkylsilyl-$(C_2-C_6)$-alkynyl, di-$(C_1-C_6)$-alkylsilyl-$(C_2-C_6)$-alkynyl, $(C_1-C_6)$-alkylsilyl-$(C_2-C_6)$-alkynyl; phenylsilyl-$(C_2-C_6)$-alkynyl;
- $(C_6-C_{14})$-aryl, $(C_6-C_{14})$-aryloxy, $(C_6-C_{14})$-arylcarbonyl and $(C_6-C_{14})$-aryloxycarbonyl, each of which may be substituted in the aryl moiety by halogen, $(C_1-C_6)$-alkyl and/or $(C_1-C_6)$-haloalkyl;
- $(C_6-C_{14})$-aryl-$(C_1-C_6)$-alkyl, $(C_6-C_{14})$-aryl-$(C_1-C_6)$-alkoxy, $(C_6-C_{14})$-aryl-$(C_1-C_6)$-alkylcarbonyl, $(C_6-C_{14})$-aryl-$(C_1-C_6)$-alkylcarbonyloxy, $(C_6-C_{14})$-aryl-$(C_1-C_6)$-alkoxycarbonyl, $(C_6-C_{14})$-aryl-$(C_1-C_6)$-alkoxycarbonyloxy;
- aminocarbonyl-$(C_1-C_6)$-alkyl, di-$(C_1-C_6)$-alkylaminocarbonyl-$(C_1-C_6)$-alkyl;
- N—(($C_1-C_6)$-haloalkanoyl)aminocarbonyl, (($C_6-C_{14})$-aryl)aminocarbonyl, di-(($C_6-C_{14})$-(($C_1-C_6)$-alkylsulfonyl)aminocarbonyl, N—(($C_1-C_6)$-haloalkylsulfonyl)aminocarbonyl, N—(($C_6-C_{14})$-arylsulfonyl)aminocarbonyl;
- $(C_1-C_6)$-alkoxy-$(C_1-C_6)$-alkyl, $(C_1-C_6)$-alkoxy-$(C_1-C_6)$-alkoxy, $(C_1-C_6)$-alkoxycarbonyl-$(C_1-C_6)$-alkoxy;
- $(C_3-C_8)$-cycloalkyl which may optionally be substituted in the cycloalkyl radical by $(C_1-C_6)$-alkyl and/or halogen; $(C_3-C_8)$-cycloalkoxy, $(C_3-C_8)$-cycloalkyl-$(C_1-C_6)$-alkyl, $(C_3-C_8)$-cycloalkyl-$(C_1-C_6)$- haloalkyl, $(C_3-C_8)$-cycloalkyl-$(C_1-C_6)$-alkoxy, $(C_3-C_8)$-cycloalkyl-$(C_1-C_6)$-haloalkoxy, $(C_3-C_8)$-cycloalkylcarbonyl, $(C_3-C_8)$-cycloalkoxycarbonyl, $(C_3-C_8)$-cycloalkyl-$(C_1-C_6)$-alkylcarbonyl, $(C_3-C_8)$-cycloalkyl-$(C_1-C_6)$-haloalkylcarbonyl, $(C_3-C_8)$-cycloalkyl-$(C_1-C_6)$-alkoxycarbonyl, $(C_3-C_8)$-cycloalkyl-$(C_1-C_6)$-haloalkoxycarbonyl, $(C_3-C_8)$-cycloalkylcarbonyloxy, $(C_3-C_8)$-cycloalkoxycarbonyloxy, $(C_3-C_8)$-cycloalkyl-$(C_1-C_6)$-alkylcarbonyloxy, $(C_3-C_8)$-cycloalkyl-$(C_1-C_6)$-haloalkylcarbonyloxy, $(C_3-C_8)$-cycloalkyl-$(C_1-C_6)$-alkoxycarbonyloxy, $(C_3-C_8)$-cycloalkyl-$(C_1-C_6)$-haloalkoxycarbonyloxy;

$(C_3-C_8)$-cycloalkenyl, $(C_3-C_8)$-cycloalkenyloxy, $(C_3-C_8)$-cycloalkenyl-$(C_1-C_6)$-alkyl, $(C_3-C_8)$-cyclo alkenyl-$(C_1-C_6)$-halo alkyl, $(C_3-C_8)$-cycloalkenyl-$(C_1-C_6)$-alkoxy, $(C_3-C_8)$-cycloalkenyl-$(C_1-C_6)$-haloalkoxy, $(C_3-C_8)$-cycloalkenylcarbonyl, $(C_3-C_8)$-cycloalkenyloxycarbonyl, $(C_3-C_8)$-cycloalkenyl-$(C_1-C_6)$-alkylcarbonyl, $(C_3-C_8)$-cycloalkenyl-$(C_1-C_6)$-haloalkylcarbonyl, $(C_3-C_8)$-cycloalkenyl-$(C_1-C_6)$-alkoxycarbonyl, $(C_3-C_8)$-cycloalkenyl-$(C_1-C_6)$-haloalkoxycarbonyl, $(C_3-C_8)$-cycloalkenylcarbonyloxy, $(C_3-C_8)$-cycloalkenyloxycarbonyloxy, $(C_3-C_8)$-cycloalkenyl-$(C_1-C_6)$-alkylcarbonyloxy, $(C_3-C_8)$-cycloalkenyl-$(C_1-C_6)$-haloalkylcarbonyloxy, $(C_3-C_8)$-cycloalkenyl-$(C_1-C_6)$-alkoxycarbonyloxy, $(C_3-C_8)$-cycloalkenyl-$(C_1-C_6)$-haloalkoxycarbonyloxy;
hydroxy-$(C_1-C_6)$-alkyl, hydroxy-$(C_1-C_6)$-alkoxy, cyano-$(C_1-C_6)$-alkoxy, cyano-$(C_1-C_6)$-alkyl; and
$(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylthio, $(C_1-C_6)$-haloalkylsulfinyl, $(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, $(C_1-C_6)$-haloalkylsulfinyl-$(C_1-C_6)$-haloalkyl, $(C_1-C_6)$-alkylsulfonyloxy, $(C_1-C_6)$-haloalkylsulfonyloxy, $(C_1-C_6)$-alkylthiocarbonyl, $(C_1-C_6)$-haloalkylthiocarbonyl, $(C_1-C_6)$-alkylthiocarbonyloxy, $(C_1-C_6)$-haloalkylthiocarbonyloxy, $(C_1-C_6)$-alkylthio-$(C_1-C_6)$-alkyl, $(C_1-C_6)$-alkylthio-$(C_1-C_6)$-alkoxy, $(C_1-C_6)$-alkylthio-$(C_1-C_6)$-alkylcarbonyl, $(C_1-C_6)$-alkylthio-$(C_1-C_6)$-alkylcarbonyloxy; $(C_4-C_{14})$-arylsulfonyl, $(C_6-C_{14})$-arylthio, $(C_6-C_{14})$-arylsulfinyl, $(C_3-C_8)$-cycloalkylthio, $(C_3-C_8)$-alkenylthio, $(C_3-C_8)$-cycloalkenylthio and $(C_3-C_6)$-alkynylthio; or $R^1$ may be attached to $R^2$ via a bond, resulting in a 5- to 7-membered partially hydrogenated carbocycle or heterocycle having at least one heteroatom selected from the group consisting of N, O, S and P, which carbocycle or heterocycle is optionally substituted by one or more substituents selected from the group consisting of hydroxy, =O, =N—O—H, =N—O—$(C_1-C_6)$-alkyl, =N—O-benzyl, =N—O-phenyl, phenyl, phenyl substituted by one or more identical or different halogen atoms, $(C_1-C_6)$-alkyl, $(C_3-C_6)$-cycloalkyl and $(C_1-C_6)$-haloalkyl;

$R^3$ is selected from the group consisting of hydrogen, $(C_1-C_6)$-alkyl, $(C_1-C_6)$-alkoxy, $(C_1-C_6)$-alkoxy-$(C_1-C_6)$-alkyl, $(C_1-C_6)$-alkoxycarbonyl and aminocarbonyl;

$R^4$ and $R^5$ are each independently of one another selected from the group consisting of hydrogen, $(C_1-C_6)$-alkyl, $(C_1-C_6)$-haloalkyl, hydroxy, $(C_1-C_6)$-alkoxy and $(C_1-C_6)$-haloalkoxy; or $R^4$ and $R^5$ together with the carbon atom to which they are attached form a saturated three- to seven-membered ring which may contain one or more heteroatoms selected from the group consisting of oxygen, sulfur and nitrogen;

$R^6$ and $R^7$ are each independently of one another selected from the group consisting of hydrogen, $(C_1-C_6)$-alkyl, $(C_1-C_6)$-haloalkyl, $(C_1-C_6)$-alkoxy, $(C_1-C_6)$-haloalkoxy, $(C_6-C_{14})$-aryl, $(C_6-C_{14})$-aryloxy, $(C_6-C_{14})$-arylcarbonyl and $(C_6-C_{14})$-aryloxycarbonyl; or the $R^6$ and $R^7$ radicals together form a $(C_1-C_7)$-alkylene group which may contain one or more oxygen and/or sulfur atoms, where the $(C_1-C_7)$-alkylene group may be mono- or polysubstituted by halogen and the respective halogen substituents may be identical or different;

n is the running number 0, 1 or 2;

$R^8$, $R^9$, $R^{10}$ and $R^{11}$ are each independently of one another selected from the group consisting of hydrogen, halogen, cyano, C(O)OH, C(O)NH$_2$, $(C_1-C_6)$-alkyl, $(C_1-C_6)$-alkylcarbonyl, $(C_1-C_6)$-alkyloxycarbonyl, $(C_1-C_6)$-alkylaminocarbonyl, $(C_1-C_6)$-dialkylaminocarbonyl, $(C_1-C_6)$-haloalkyl, $(C_1-C_6)$-alkoxy, $(C_1-C_6)$-haloalkoxy, $(C_2-C_6)$-alkenyl, $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl and nitro, where the $R^9$ and $R^{10}$ radicals may be attached to one another via an —O—CH$_2$—O— group forming a ring;

X represents a bond, CH$_2$, O, S, carbonyl, NH, CR$^{12}$R$^{13}$, NR$^{14}$, CH$_2$O or CH$_2$S, where in the two last-mentioned groups the carbon atom is attached to the aromatic moiety and the heteroatom O or S is attached to the partially hydrogenated moiety of the amine;

$R^{12}$ and $R^{13}$ are each independently of one another selected from the group consisting of hydrogen, $(C_1-C_6)$-alkyl and $(C_1-C_6)$-haloalkyl; and $R^{14}$ is selected from the group consisting of hydrogen, $(C_1-C_6)$-alkyl and $(C_1-C_6)$-haloalkyl.

The amino group in the 3 position of the 1,2,4-triazine in the bis(amino)triazines of the formula (I) according to the invention has a partially hydrogenated bicyclic substituent, said partially hydrogenated bicyclic substituent being attached to the amine in the alpha position to the aromatic system.

DETAILED DESCRIPTION OF A PREFERRED EMBODIMENT

As well as a good profile of efficacy and good crop plant compatibility, the compounds of the formula (I) are notable for their inexpensive preparation, since the substances of the invention can be prepared from inexpensive and readily available precursors by inexpensive processes. It is therefore possible to dispense with the use of intermediates that are costly and difficult to obtain.

There follows a description of preferred, particularly preferred and very particularly preferred definitions of each of the individual substituents. The other substituents of the general formula (I) which are not specified hereinafter have the definition given above. The same also applies to the running number n, meaning that the running number n in the embodiments which follow is 0, 1 or 2.

A first embodiment of the present invention encompasses compounds of the general formula (I) in which $R^1$ is preferably selected from the group consisting of hydrogen, amino, (($C_1$-$C_6$)-alkyl)amino, (($C_3$-$C_6$)-cycloalkyl)amino and di-(($C_1$-$C_6$)-alkyl)amino;

$R^1$ is particularly preferably selected from the group consisting of hydrogen, amino, (($C_1$-$C_3$)-alkyl)amino, (($C_3$-$C_6$)-cycloalkyl)amino and di-(($C_1$-$C_3$)-alkyl)amino;

$R^1$ is very particularly preferably selected from the group consisting of hydrogen, amino, $NH(CH_3)$, $N(H)$-cyclopropyl and $N(CH_3)_2$; and in which $R^1$ most preferably represents hydrogen and amino and very particularly preferably amino.

A second embodiment of the present invention encompasses compounds of the general formula (I) in which $R^2$ is preferably selected from the group consisting of hydrogen, halogen, hydroxy, nitro, amino, cyano, C(O)OH, $C(O)NH_2$;
($C_1$-$C_6$)-alkyl, ($C_1$-$C_6$)-haloalkyl;
($C_1$-$C_6$)-alkylcarbonyl, ($C_1$-$C_6$)-haloalkylcarbonyl, ($C_1$-$C_6$)-alkoxycarbonyl, ($C_1$-$C_6$)-haloalkoxycarbonyl;
($C_2$-$C_6$)-alkenyl, ($C_2$-$C_6$)-haloalkenyl;
($C_2$-$C_6$)-alkynyl, ($C_2$-$C_6$)-haloalkynyl;
($C_6$-$C_{14}$)-aryl which may be substituted in the aryl moiety by halogen, ($C_1$-$C_6$)-alkyl and/or ($C_1$-$C_6$)-haloalkyl;
($C_1$-$C_6$)-alkoxy-($C_1$-$C_6$)-alkyl, hydroxy-($C_1$-$C_6$)-alkyl;
(($C_1$-$C_6$)-alkyl)aminocarbonyl, di-(($C_1$-$C_6$)-alkyl)aminocarbonyl, N—(($C_1$-$C_6$)-alkylsulfonyl)aminocarbonyl, N—(($C_1$-$C_6$)-haloalkylsulfonyl)aminocarbonyl, ($C_3$-$C_8$)-cycloalkylcarbonyl, ($C_3$-$C_8$)-cycloalkoxycarbonyl;
($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylsulfinyl, ($C_4$-$C_{14}$)-arylsulfonyl and ($C_6$-$C_{14}$)-arylsulfinyl; ($C_1$-$C_6$)-alkoxy-($C_1$-$C_6$)-alkyl, $R^2$ is more preferably selected from the group consisting of halogen, cyano, C(O)OH,
($C_1$-$C_6$)-alkyl, ($C_1$-$C_6$)-haloalkyl;
($C_1$-$C_6$)-alkylcarbonyl, ($C_1$-$C_6$)-haloalkylcarbonyl, ($C_1$-$C_6$)-alkoxycarbonyl, ($C_1$-$C_6$)-haloalkoxycarbonyl;
($C_2$-$C_6$)-alkenyl, ($C_2$-$C_6$)-haloalkenyl;
($C_2$-$C_6$)-alkynyl, ($C_2$-$C_6$)-haloalkynyl;
phenyl which may be substituted in the aryl moiety by halogen, ($C_1$-$C_6$)-alkyl and/or ($C_1$-$C_6$)-haloalkyl;
($C_1$-$C_3$)-alkoxy-($C_1$-$C_6$)-alkyl, hydroxy-($C_1$-$C_6$)-alkyl;
(($C_1$-$C_3$)-alkyl)aminocarbonyl, di-(($C_1$-$C_3$)-alkyl)aminocarbonyl;
N—(($C_1$-$C_3$)-alkylsulfonyl)aminocarbonyl, N—(($C_1$-$C_3$)-haloalkylsulfonyl)aminocarbonyl, ($C_3$-$C_6$)-cycloalkylcarbonyl, ($C_3$-$C_6$)-cycloalkoxycarbonyl;
($C_1$-$C_3$)-alkylsulfonyl, ($C_1$-$C_3$)-alkylsulfinyl, ($C_1$-$C_3$)-haloalkylsulfonyl, ($C_1$-$C_6$)-haloalkylsulfinyl, ($C_4$-$C_{14}$)-arylsulfonyl and ($C_6$-$C_{14}$)-arylsulfinyl;

$R^2$ is particularly preferably selected from the group consisting of
Cl, Br, cyano, C(O)OH, $C(O)NH_2$;
($C_1$-$C_6$)-alkyl, ($C_1$-$C_6$)-haloalkyl, ($C_1$-$C_6$)-alkylcarbonyl, ($C_1$-$C_6$)-haloalkylcarbonyl;
($C_1$-$C_6$)-alkoxycarbonyl, ($C_1$-$C_6$)-haloalkoxycarbonyl;
($C_2$-$C_6$)-alkenyl, ($C_2$-$C_6$)-haloalkenyl;
($C_2$-$C_6$)-alkynyl, ($C_2$-$C_6$)-haloalkynyl;
phenyl which may be substituted by F, Cl, Br, methyl and/or trifluoromethyl;
($C_1$-$C_3$)-alkoxy-($C_1$-$C_3$)-alkyl, hydroxy-($C_1$-$C_3$)-alkyl;
(($C_1$-$C_2$)-alkyl)aminocarbonyl, di-(($C_1$-$C_2$)-alkyl)aminocarbonyl, N—(($C_1$-$C_2$)-alkylsulfonyl)aminocarbonyl, N—(($C_1$-$C_2$)-haloalkylsulfonyl)aminocarbonyl;
($C_3$-$C_6$)-cycloalkylcarbonyl, ($C_3$-$C_6$)-cycloalkoxycarbonyl;
($C_1$-$C_3$)-alkylsulfonyl, ($C_1$-$C_3$)-alkylsulfinyl, ($C_1$-$C_3$)-haloalkylsulfonyl, ($C_1$-$C_6$)-haloalkylsulfinyl, ($C_4$-$C_{14}$)-arylsulfonyl, ($C_6$-$C_{14}$)-arylsulfinyl;

$R^2$ is very particularly preferably selected from the group consisting of
Cl, cyano, $C(O)NH_2$;
($C_1$-$C_3$)-haloalkyl, ($C_1$-$C_3$)-alkylcarbonyl, ($C_1$-$C_3$)-haloalkylcarbonyl;
($C_1$-$C_6$)-alkoxycarbonyl, ($C_1$-$C_6$)-haloalkoxycarbonyl;
($C_2$-$C_6$)-alkenyl, ($C_2$-$C_6$)-haloalkenyl;
methoxy-($C_1$-$C_3$)-alkyl, hydroxy-($C_1$-$C_3$)-alkyl;
(($C_1$-$C_2$)-alkyl)aminocarbonyl, di-(($C_1$-$C_2$)-alkyl)aminocarbonyl, ($C_1$-$C_3$)-alkylsulfonyl, ($C_1$-$C_3$)-alkylsulfinyl; and in which $R^2$ most preferably represents Cl, cyano, $C(O)NH_2$, trifluoromethyl, acetyl ($C(O)CH_3$), trifluoroacetyl ($C(O)CF_3$), methoxy-($C_2$-$C_3$)-alkyl, hydroxy-($C_2$-$C_3$)-alkyl, ($C_1$-$C_2$)-alkoxycarbonyl, ($C_2$-$C_3$)-alkenyl, ($C_2$-$C_3$)-haloalkenyl, methylaminocarbonyl, dimethylaminocarbonyl, methylsulfonyl and methylsulfinyl.

A third embodiment of the present invention encompasses compounds of the general formula (I) in which $R^3$ preferably represents hydrogen.

A fourth embodiment of the present invention encompasses compounds of the general formula (I) in which $R^4$ and $R^5$ are preferably each independently of one another selected from the group consisting of hydrogen, hydroxy, ($C_1$-$C_6$)-alkyl, ($C_1$-$C_6$)-alkylphenyl and ($C_1$-$C_6$)-alkoxy;

$R^4$ and $R^5$ are particularly preferably each independently of one another selected from the group consisting of hydrogen, ($C_1$-$C_6$)-alkyl and ($C_1$-$C_6$)-alkoxy;

$R^4$ and $R^5$ are very particularly preferably each independently of one another selected from the group consisting of hydrogen, ($C_1$-$C_3$)-alkyl, ($C_1$-$C_6$)-alkoxy; and in which $R^4$ and $R^5$ most preferably each independently of one another represent hydrogen or methyl.

In this fourth embodiment, it is especially preferable for at least one of the $R^4$ and $R^5$ radicals to represent hydrogen. In other words, when in each case at least one of the $R^4$ and $R^5$ radicals is hydrogen and the other $R^4$ and $R^5$ radical is not hydrogen, especially ($C_1$-$C_6$)-alkyl, preferably methyl ($CH_3$).

A fifth embodiment of the present invention encompasses compounds of the general formula (I) in which $R^4$ and $R^5$ together with the carbon atom to which they are attached form a saturated three- to six-membered ring which may contain a heteroatom selected from the group consisting of oxygen, sulfur and nitrogen;

$R^4$ and $R^5$ together with the carbon atom to which they are attached preferably form a saturated three- to six-membered ring which may contain an oxygen atom;

$R^4$ and $R^5$ together with the carbon atom to which they are attached particularly preferably form a saturated three- to six-membered ring which may contain an oxygen atom; and in which $R^4$ and $R^5$ together with the carbon atom to which they are attached most preferably form a saturated three-membered ring which may contain an oxygen atom or form a 4-pyran ring.

A sixth embodiment of the present invention encompasses compounds of the general formula (I) in which $R^6$ and $R^7$ are preferably independently of one another selected from the group consisting of hydrogen, $(C_1-C_6)$-alkyl and $(C_6-C_{14})$-aryl;

$R^6$ and $R^7$ are particularly preferably independently of one another selected from the group consisting of hydrogen, methyl and phenyl;

$R^6$ and $R^7$ very particularly preferably each independently of one another represent hydrogen or methyl; and in which $R^6$ and $R^7$ most preferably represent hydrogen.

A seventh embodiment of the present invention encompasses compounds of the general formula (I) in which $R^8$ is preferably selected from the group consisting of hydrogen, halogen, $(C_1-C_6)$-alkyl, $(C_1-C_6)$-alkoxy and $(C_6-C_{14})$-aryl;

$R^8$ is particularly preferably selected from the group consisting of hydrogen, halogen, $(C_1-C_3)$-alkyl and $(C_6-C_8)$-aryl;

$R^8$ is very particularly preferably selected from the group consisting of hydrogen, fluorine, chlorine, $CH_3$ and phenyl; and in which $R^8$ most preferably represents hydrogen or $CH_3$.

An eighth embodiment of the present invention encompasses compounds of the general formula (I) in which $R^9$ is preferably selected from the group consisting of hydrogen, halogen, $(C_1-C_6)$-alkyl and $(C_1-C_6)$-alkoxy;

$R^9$ is particularly preferably selected from the group consisting of hydrogen, chlorine, fluorine and $(C_1-C_3)$-alkoxy;

$R^9$ is very particularly preferably selected from the group consisting of hydrogen, fluorine, chlorine and methoxy; and in which $R^9$ most preferably represents hydrogen.

A ninth embodiment of the present invention encompasses compounds of the general formula (I) in which $R^{10}$ is preferably selected from the group consisting of hydrogen, halogen, cyano, aminocarbonyl, hydroxycarbonyl, $(C_1-C_6)$-alkyl, $(C_1-C_6)$-haloalkyl, $(C_1-C_6)$-alkoxy, $(C_2-C_6)$-alkenyl, $(C_2-C_6)$-alkynyl, $(C_1-C_6)$-alkyl-$(C_2-C_6)$-alkynyl, hydroxy-$(C_1-C_6)$-alkyl-$(C_2-C_6)$-alkynyl, $(C_1-C_6)$-alkoxy-$(C_2-C_6)$-alkynyl and aryl-$(C_2-C_6)$-alkynyl;

$R^{10}$ is particularly preferably selected from the group consisting of hydrogen, fluorine, chlorine, bromine, iodine, cyano, methoxy ($OCH_3$), $(C_1-C_3)$-alkyl, $(C_1-C_3)$-haloalkyl, $(C_1-C_3)$-alkoxy, $(C_2-C_4)$-alkenyl, $(C_2-C_4)$-alkynyl, $(C_1-C_3)$-alkyl-$(C_2-C_4)$-alkynyl, hydroxy-$(C_1-C_3)$-alkyl-$(C_2-C_4)$-alkynyl, $(C_1-C_3)$-alkoxy-$(C_2-C_4)$-alkynyl and phenyl-$(C_2-C_4)$-alkynyl;

$R^{10}$ is very particularly preferably selected from the group consisting of hydrogen, fluorine, chlorine, bromine, iodine, cyano, methyl, C≡CH and C≡CCH$_3$; and in which $R^{10}$ most preferably represents hydrogen or $CH_3$.

A tenth embodiment of the present invention encompasses compounds of the general formula (I) in which $R^{11}$ is preferably selected from the group consisting of hydrogen and $(C_1-C_6)$-alkyl;

$R^{11}$ is particularly preferably selected from the group consisting of hydrogen and $(C_1-C_4)$-alkyl;

$R^{11}$ very particularly preferably represents hydrogen or methyl; and in which $R^{11}$ most preferably represents hydrogen.

An eleventh embodiment of the present invention encompasses compounds of the general formula (I) in which X is preferably selected from the group consisting of a chemical bond, $CH_2$, O, S, carbonyl, NH, $CH(C_1-C_6)$-alkyl, $N(C_1-C_6)$-alkyl, $OCH_2$ and $SCH_2$, where in the two last-mentioned groups the carbon atom is attached to the aromatic moiety and the heteroatom O or S is attached to the partially hydrogenated moiety of the amine;

X is particularly preferably selected from the group consisting of a chemical bond, $CH_2$, O, S, $CHCH_3$, $NCH_3$, $OCH_2$ and $SCH_2$, where in the two last-mentioned groups the carbon atom is attached to the aromatic moiety and the heteroatom O or S is attached to the partially hydrogenated moiety of the amine; and in which X most preferably represents a chemical bond or $CH_2$.

A twelfth embodiment of the present invention encompasses compounds of the general formula (I) in which n is preferably 0 or 1.

In the context of the present invention, it is possible to combine the individual preferred, particularly preferred, very particularly preferred and most preferred meanings of the substituents $R^1$ to $R^{11}$ and X with one another as desired, where the running number n is 0, 1 or 2, preferably 0 or 1.

This means that the present invention encompasses compounds of the general formula (I) in which, for example, the substituent $R^1$ has a preferred meaning and the substituents $R^2$ to $R^{14}$ have the general meaning or else the substituent $R^2$ has a preferred meaning, the substituent $R^3$ has a particularly preferred or very particularly preferred meaning and the remaining substituents have a general meaning.

Four of these combinations of the definitions given above for the substituents $R^1$ to $R^{11}$ and X are illustrated by way of example hereinafter and each are disclosed as further embodiments:

combination of the definitions given above for the substituents $R^1$ to $R^{11}$ and X in each case as being particularly preferred (twelfth embodiment), combination of the definitions given above for the substituents $R^1$ to $R^{11}$ and X in each case as being very particularly preferred (thirteenth embodiment), and combination of the definition given above for the substituent $R^1$ as being very particularly preferred with the definitions given above for the substituents $R^1$ to $R^{11}$ and X in each case as being particularly preferred (fourteenth embodiment).

The aforementioned further embodiments that are based on the combinations of the substituents are disclosed explicitly hereinafter for reasons of clarity:

A thirteenth embodiment of the present invention encompasses compounds of the general formula (I) in which $R^1$ is selected from the group consisting of hydrogen, amino, $((C_1-C_3)$-alkyl)amino, $((C_3-C_6)$-cycloalkyl)amino, di-$((C_1-C_3)$-alkyl)amino;

$R^2$ is selected from the group consisting of Cl, Br, cyano, C(O)OH, C(O)NH$_2$;
$(C_1-C_6)$-alkyl, $(C_1-C_6)$-haloalkyl, $(C_1-C_6)$-alkylcarbonyl, $(C_1-C_6)$-haloalkylcarbonyl;
$(C_1-C_6)$-alkoxycarbonyl, $(C_1-C_6)$-haloalkoxycarbonyl;
$(C_2-C_6)$-alkenyl, $(C_2-C_6)$-haloalkenyl;

($C_2$-$C_6$)-alkynyl, ($C_2$-$C_6$)-haloalkynyl;
phenyl which may be substituted by F, Cl, Br, methyl and/or trifluoromethyl;
($C_1$-$C_6$)-alkoxy-($C_1$-$C_6$)-alkyl, hydroxy-($C_1$-$C_6$)-alkyl;
(($C_1$-$C_2$)-alkyl)aminocarbonyl, di-(($C_1$-$C_2$)-alkyl) aminocarbonyl, N—(($C_1$-$C_2$)-alkylsulfonyl)aminocarbonyl, N—(($C_1$-$C_2$)-haloalkylsulfonyl)aminocarbonyl;
($C_3$-$C_6$)-cycloalkylcarbonyl, ($C_3$-$C_6$)-cycloalkoxycarbonyl;
($C_1$-$C_3$)-alkylsulfonyl, ($C_1$-$C_3$)-alkylsulfinyl, ($C_1$-$C_3$)-haloalkylsulfonyl, ($C_1$-$C_6$)-haloalkylsulfinyl, ($C_4$-$C_{14}$)-arylsulfonyl, ($C_6$-$C_{14}$)-arylsulfinyl;
$R^3$ represents hydrogen;
$R^4$ and $R^5$ are each independently of one another selected from the group consisting of hydrogen, ($C_1$-$C_6$)-alkyl and ($C_1$-$C_6$)-alkoxy;
$R^6$ and $R^7$ are independently of one another selected from the group consisting of hydrogen, methyl and phenyl;
$R^8$ is selected from the group consisting of hydrogen, halogen, ($C_1$-$C_3$)-alkyl and ($C_6$-$C_8$)-aryl;
$R^9$ is selected from the group consisting of hydrogen, chlorine, fluorine and ($C_1$-$C_3$)-alkoxy;
$R^{10}$ is selected from the group consisting of hydrogen, fluorine, chlorine, bromine, iodine, cyano, methoxy ($OCH_3$), ($C_1$-$C_3$)-alkyl, ($C_1$-$C_3$)-haloalkyl, ($C_1$-$C_3$)-alkoxy, ($C_2$-$C_4$)-alkenyl, ($C_2$-$C_4$)-alkynyl, ($C_1$-$C_3$)-alkyl-($C_2$-$C_4$)-alkynyl, hydroxy-($C_1$-$C_3$)-alkyl-($C_2$-$C_4$)-alkynyl, ($C_1$-$C_3$)-alkoxy-($C_2$-$C_4$)-alkynyl and phenyl-($C_2$-$C_4$)-alkynyl;
$R^{11}$ is selected from the group consisting of hydrogen and ($C_1$-$C_4$)-alkyl; and
X is selected from the group consisting of a chemical bond, $CH_2$, O, S, $CHCH_3$, $NCH_3$, $OCH_2$ and $SCH_2$, where in the two last-mentioned groups the carbon atom is attached to the aromatic moiety and the heteroatom O or S is attached to the partially hydrogenated moiety of the amine.

A fourteenth embodiment of the present invention encompasses compounds of the general formula (I) in which
$R^1$ is selected from the group consisting of hydrogen, amino, $NH(CH_3)$, $N(H)$-cyclopropyl and $N(CH_3)_2$;
$R^2$ is selected from the group consisting of
Cl, cyano, $C(O)NH_2$;
($C_1$-$C_3$)-haloalkyl, ($C_1$-$C_3$)-alkylcarbonyl, ($C_1$-$C_3$)-haloalkylcarbonyl;
($C_1$-$C_6$)-alkoxycarbonyl, ($C_1$-$C_6$)-haloalkoxycarbonyl;
($C_2$-$C_6$)-alkenyl, ($C_2$-$C_6$)-haloalkenyl;
($C_1$-$C_3$)-alkoxy-($C_1$-$C_6$)-alkyl, hydroxy-($C_1$-$C_6$)-alkyl;
(($C_1$-$C_2$)-alkyl)aminocarbonyl, di-(($C_1$-$C_2$)-alkyl) aminocarbonyl;
($C_1$-$C_3$)-alkylsulfonyl, ($C_1$-$C_3$)-alkylsulfinyl;
$R^3$ represents hydrogen;
$R^4$ and $R^5$ are each independently of one another selected from the group consisting of hydrogen, ($C_1$-$C_3$)-alkyl, ($C_1$-$C_6$)-alkoxy;
$R^6$ and $R^7$ each independently of one another represent hydrogen or methyl;
$R^8$ is selected from the group consisting of hydrogen, fluorine, chlorine, $CH_3$ and phenyl;
$R^9$ is selected from the group consisting of hydrogen, fluorine, chlorine and methoxy;
$R^{10}$ is selected from the group consisting of hydrogen, fluorine, chlorine, bromine, iodine, cyano, methyl, $C\equiv CH$ and $C\equiv CCH_3$;
$R^{11}$ represents hydrogen or methyl; and
X is selected from the group consisting of a chemical bond, $CH_2$, O, S, $CHCH_3$, $NCH_3$, $OCH_2$ and $SCH_2$, where in the two last-mentioned groups the carbon atom is attached to the aromatic moiety and the heteroatom O or S is attached to the partially hydrogenated moiety of the amine.

A fifteenth embodiment of the present invention encompasses compounds of the general formula (I) in which
$R^4$ represents hydrogen and amino;
$R^2$ is selected from the group consisting of Cl, cyano, $C(O)NH_2$, trifluoromethyl, acetyl ($C(O)CH_3$), trifluoroacetyl ($C(O)CF_3$), ($C_1$-$C_2$)-alkoxycarbonyl, ($C_1$-$C_2$)-haloalkoxycarbonyl, ($C_2$-$C_3$)-alkenyl, ($C_2$-$C_3$)-haloalkenyl, ($C_1$-$C_3$)-alkoxy-($C_1$-$C_3$)-alkyl, hydroxy-($C_1$-$C_3$)-alkyl, methylaminocarbonyl, dimethylaminocarbonyl, methylsulfonyl and
$R^3$ represents hydrogen;
$R^4$ and $R^5$ each independently of one another represent hydrogen or methyl;
$R^6$ and $R^7$ represent hydrogen;
$R^8$ represents hydrogen or $CH_3$;
$R^9$ represents hydrogen;
$R^{10}$ represents hydrogen or $CH_3$;
$R^{11}$ represents hydrogen; and
X represents a chemical bond or $CH_2$.

A sixteenth embodiment of the present invention encompasses compounds of the general formula (I) in which
$R^1$ is selected from the group consisting of hydrogen, amino, $NH(CH_3)$, $N(H)$-cyclopropyl and $N(CH_3)_2$;
$R^2$ is selected from the group consisting of
Cl, cyano, $C(O)NH_2$;
($C_1$-$C_3$)-haloalkyl, ($C_1$-$C_3$)-alkylcarbonyl, ($C_1$-$C_3$)-haloalkylcarbonyl;
($C_1$-$C_6$)-alkoxycarbonyl, ($C_1$-$C_6$)-haloalkoxycarbonyl;
($C_2$-$C_6$)-alkenyl, ($C_2$-$C_6$)-haloalkenyl;
methoxy-($C_2$-$C_3$)-alkyl, hydroxy-($C_2$-$C_3$)-alkyl;
(($C_1$-$C_2$)-alkyl)aminocarbonyl, di-(($C_1$-$C_2$)-alkyl) aminocarbonyl;
($C_1$-$C_3$)-alkylsulfonyl, ($C_1$-$C_3$)-alkylsulfinyl;
$R^3$ represents hydrogen;
$R^4$ and $R^5$ together with the carbon atom to which they are attached form a saturated three- to six-membered ring which may contain an oxygen atom;
$R^6$ and $R^7$ each independently of one another represent hydrogen or methyl;
$R^8$ is selected from the group consisting of hydrogen, fluorine, chlorine, $CH_3$ and phenyl;
$R^9$ is selected from the group consisting of hydrogen, fluorine, chlorine and methoxy; cyano, methyl, $C\equiv CH$ and $C\equiv CCH_3$;
$R^{11}$ represents hydrogen or methyl; and
X represents a chemical bond or $CH_2$.

In the context of the present invention, the compound of the general formula (I) also includes compounds quaternized on a nitrogen atom by a) protonation, b) alkylation or c) oxidation. In this respect, particular mention should be made of the corresponding N-oxides.

The compounds of the formula (I) are capable of forming salts. Salts may be formed by the action of a base on those compounds of the formula (I) that bear an acidic hydrogen atom. Examples of suitable bases are organic amines such as trialkylamines, morpholine, piperidine or pyridine, and the hydroxides, carbonates and bicarbonates of ammonium, alkali metals or alkaline earth metals, especially sodium hydroxide, potassium hydroxide, sodium carbonate, potassium carbonate, sodium bicarbonate and potassium bicarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR'R''R''']⁺ in which R to R''' each independently of one another represent an organic radical, in particular alkyl, aryl, aralkyl or alkylaryl. Also suitable are alkylsulfonium and alkylsulfoxonium salts, such as $(C_1-C_4)$-trialkylsulfonium and $(C_1-C_4)$-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts will comprise the conjugated base of the acid as the anion.

Suitable substituents present in deprotonated form, such as, for example, sulfonic acids or carboxylic acids, may form inner salts with groups which for their part can be protonated, such as amino groups.

The compounds of the formula (I) and their salts are also referred to for short hereinafter as "compounds (I)" according to the invention or used in accordance with the invention.

In the general formula (I) and in all the other formulae of the present invention, the radicals alkyl, alkoxy, haloalkyl, haloalkoxy, alkylamino, alkylthio, haloalkylthio and the corresponding unsaturated and/or substituted radicals can in each case be straight-chain or branched in the carbon skeleton. Unless stated specifically, preference is given for these radicals to the lower carbon skeletons, for example those having 1 to 6 carbon atoms, in particular 1 to 4 carbon atoms, or in the case of unsaturated groups having 2 to 6 carbon atoms, in particular 2 to 4 carbon atoms. Alkyl radicals, both alone and in the composite definitions such as alkoxy, haloalkyl, etc., are, for example, methyl, ethyl, n-propyl or isopropyl, n-butyl, isobutyl, tert-butyl or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the definition of the possible unsaturated radicals corresponding to the alkyl radicals; where at least one double bond or triple bond is present, preferably one double bond or triple bond, respectively. Alkenyl is, for example, vinyl, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, ethynyl, propargyl, but-2-yn-1-yl, but-3-yn-1-yl and 1-methylbut-3-yn-1-yl.

Cycloalkyl groups are, for example, cyclopropyl, cyclobutyl, cyclopentyl, cyclohexyl, cycloheptyl and cyclooctyl. The cycloalkyl groups can be present in bi- or tricyclic form.

If haloalkyl groups and haloalkyl radicals of haloalkoxy, haloalkylthio, haloalkenyl, haloalkynyl etc. are stated, the lower carbon skeletons of these radicals having, for example, 1 to 6 carbon atoms or 2 to 6 carbon atoms, especially 1 to 4 carbon atoms or preferably 2 to 4 carbon atoms, and the corresponding unsaturated and/or substituted radicals are in each case straight-chain or branched in the carbon skeleton. Examples are difluoromethyl, 2,2,2-trifluoroethyl, trifluoroallyl, 1-chloroprop-1-yl-3-yl.

Alkylene groups in these radicals are the lower carbon skeletons, for example those having 1 to 10 carbon atoms, especially 1 to 6 carbon atoms, or preferably 2 to 4 carbon atoms, and also the corresponding unsaturated and/or substituted radicals in the carbon skeleton which may in each case be straight-chain or branched. Examples are methylene, ethylene, n- and isopropylene and n-, s-, iso-, t-butylene.

Hydroxyalkyl groups in these radicals are the lower carbon skeletons, for example those having 1 to 6 carbon atoms, especially 1 to 4 carbon atoms, and also the corresponding unsaturated and/or substituted radicals in the carbon skeleton which may in each case be straight-chain or branched. Examples of these are 1,2-dihydroxyethyl and 3-hydroxypropyl.

Halogen is fluorine, chlorine, bromine or iodine. Haloalkyl, -alkenyl and -alkynyl are alkyl, alkenyl and alkynyl partly or fully substituted by halogen, preferably by fluorine, chlorine or bromine, especially by fluorine and/or chlorine, for example monohaloalkyl, perhaloalkyl, $CF_3$, $CF_2Cl$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same correspondingly applies to haloalkenyl and other halogen-substituted radicals.

Aryl is a monocyclic, bicyclic or polycyclic aromatic system, for example phenyl or naphthyl, preferably phenyl.

Primarily for reasons of higher herbicidal activity, better selectivity and/or better preparability, compounds of the general formula (I) according to the invention or the agrochemical salts or quaternary N derivatives thereof that are of particular interest are those in which individual radicals have one of the preferred definitions already specified or specified below, or especially those in which one or more of the preferred definitions already specified or specified below occur in combination.

The abovementioned general or preferred radical definitions apply both to the end products of the general formula (I) and, correspondingly, to the starting materials and intermediates required in each case for the preparation. These radical definitions can be exchanged for one another, i.e. including between the given preferred ranges.

The present compounds of the general formula (I) have, at the point of attachment to the amino-1,2,4-triazine, a chiral carbon atom which, in the structure shown below, is indicated by the marker (*):

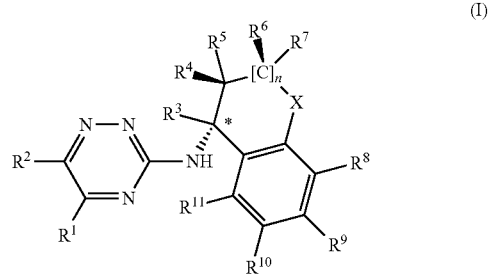

According to the rules of Cahn, Ingold and Prelog (CIP rules), this carbon atom can have either an (R) configuration or an (S) configuration.

The present invention encompasses compounds of the general formula (I) both with (S) and with (R) configuration, meaning that the present invention encompasses the compounds of the general formula (I) in which the carbon atom in question has
 (1) an (R) configuration; or
 (2) an (S) configuration.

In addition, the scope of the present invention also encompasses (3) any mixtures of compounds of the general formula (I) having an (R) configuration (compounds of the general formula (I-(R)) with compounds of the general formula (I) having an (S) configuration (compounds of the general formula (I-S)), the present invention also encompassing a racemic mixture of the compounds of the general formula (I) having (R) and (S) configuration.

However, within the context of the present invention, preference is given to using particularly compounds of the general formula (I) having (R) configuration with a selectivity of 60 to 100%, preferably 80 to 100%, especially 90 to 100%, very particularly 95 to 100%, where the particular (R) compound is present with an enantioselectivity of in each case more than 50% ee, preferably 60 to 100% ee, especially 80 to 100% ee, very particularly 90 to 100% ee, most preferably 95 to 100% ee, based on the total content of (R) compound in question.

Accordingly, the present invention relates especially to compounds of the general formula (I*) in which the stereochemical configuration on the carbon atom marked by (*) is present with a stereochemical purity of 60 to 100% (R), preferably 80 to 100% (R), especially 90 to 100% (R), very particularly 95 to 100% (R).

Taking into account the Cahn, Ingold and Prelog rule, at the carbon atom marked by (*) there may also be a situation in which, owing to the priority of the substituents in question, the (S) configuration is preferred at the carbon atom marked by (*). This is the case, for example, when the $R^4$ and/or $R^5$ radicals correspond to a $C_1$-$C_6$-alkoxy radical.

Accordingly, within the context of the present invention, preference is given especially to compounds of the general formula (I) whose spatial arrangement corresponds to that of the compounds of the general formula (I) where $R^4$ and $R^5$=hydrogen having the (R) configuration, with a selectivity of 60 to 100%, preferably 80 to 100%, especially 90 to 100%, very particularly 95 to 100%, where the respective (R)-analogous compound is present with an enantioselectivity of in each case more than 50% ee, preferably 60 to 100% ee, especially 80 to 100% ee, very particularly 90 to 100% ee, most preferably 95 to 100% ee, based on the total content of (R)-analogous compound in question. Accordingly, the present invention relates especially to compounds of the general formula (I) in which the stereochemical configuration on the carbon atom marked by (*) is present with a stereochemical purity of 60 to 100% (R or R analog), preferably 80 to 100% (R or R analog), especially 90 to 100% (R or R analog), very particularly 95 to 100% (R or R analog).

In particular, the compounds of the general formula (I) according to the invention may have further centers of chirality at the carbon atoms marked by () and (*):

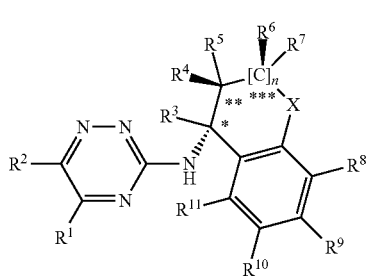

(I)

In the context of the present invention, any stereochemical configurations are possible at the carbon atoms marked by (*), () and (*):

| Configuration of carbon atom (*) | Configuration of carbon atom () | Configuration of carbon atom (*) |
|---|---|---|
| R | R | R |
| R | R | S |
| R | S | R |
| S | R | R |
| R | S | S |
| S | R | S |
| S | S | R |
| S | S | S |

In addition, depending on the respective radicals chosen, further stereoelements may be present in the compounds of the general formula (I) according to the invention.

If, for example, one or more alkenyl groups are present, diastereomers (Z and E isomers) may occur.

If, for example, one or more asymmetric carbon atoms are present, enantiomers and diastereomers may occur.

Corresponding stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention thus also relates to all stereoisomers which are encompassed by the general formula (I) but are not shown in their specific stereomeric form, and to mixtures thereof.

Particular preference is given to compounds of the general formula (I)

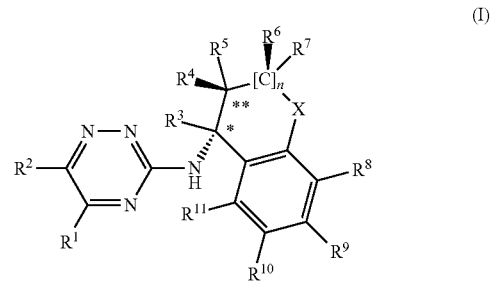

(I)

in which the chiral carbon atom marked by (*) has an (R) configuration and the chiral carbon atom marked by (**) has an (S) configuration.

The possible combinations of the various substituents of the general formula (I) should be understood such that the general principles of the construction of chemical compounds have to be observed, i.e. the formula (I) does not encompass any compounds known by the person skilled in the art to be chemically impossible.

Examples of the compounds of the general formula (I) are shown below in tabular form.

Table 1 below specifies the substituents defined in general terms in formula (I). In this table:

"$StNR^3$" is the stereochemical arrangement at the carbon atom to which NH and $R^3$ are attached, "$StR^4R^5$" and "$StR^6R^7$" are analogously the carbon atoms to which the respective substituents are attached, the bond of the substituents is on the left in each case, if two binding sites are given for X, the left bond attaches to the aromatic ring and the right bond to the hydrogenated part of the bicyclic amine, a hyphen "-" denotes a direct bond, and
if n=0, the table does not contain an entry in the corresponding field for $R^6$ and $R^7$.

TABLE 1

Examples of compounds of the general formula (I)

| No. | $R^1$ | $R^2$ | $R^3$ | St N $R^3$ | $R^4$ | $R^5$ | St $R^4$ $R^5$ | $R^6$ | $R^7$ | n | St $R^6$ $R^7$ | $R^8$ | $R^9$ | $R^{10}$ | $R^{11}$ | X |
|---|---|---|---|---|---|---|---|---|---|---|---|---|---|---|---|---|
| 1.1 | N(H)-cyclopropyl | Cl | H | R | H | H | | H | H | 2 | | H | H | H | H | — |
| 1.2 | N(H)-cyclopropyl | Cl | H | R | CH$_3$ | H | S | H | H | 1 | | H | H | CH$_3$ | H | — |
| 1.3 | NH$_2$ | Cl | H | R | CH$_3$ | H | S | H | H | 1 | | H | H | CH$_3$ | H | — |
| 1.4 | NH$_2$ | Cl | H | R | H | H | | H | H | 2 | | H | H | H | H | — |
| 1.5 | NH$_2$ | t-butyl | H | R | H | H | | H | H | 2 | | H | H | H | H | — |
| 1.6 | NH$_2$ | t-butyl | H | R | CH$_3$ | H | S | H | H | 1 | | H | H | CH$_3$ | H | — |
| 1.7 | NH$_2$ | t-butyl | H | R | H | H | | H | H | 1 | | H | H | H | H | — |
| 1.8 | NH$_2$ | t-butyl | H | rac | H | H | | H | H | 1 | | H | H | H | H | O |
| 1.9 | N(H)CH$_3$ | Cl | H | rac | H | H | | H | H | 2 | | H | H | H | H | — |
| 1.10 | N(H)-cyclopropyl | Cl | H | rac | H | H | | H | H | 2 | | H | H | H | H | — |
| 1.11 | N(H)-cyclopropyl | Cl | H | rac | H | H | | H | H | 1 | | H | H | H | H | — |
| 1.12 | N(CH$_3$)$_2$ | Cl | H | rac | H | H | | H | H | 1 | | H | H | H | H | — |
| 1.13 | N(H)CH$_3$ | Cl | H | rac | H | H | | H | H | 1 | | H | H | H | H | — |
| 1.14 | N(H)-cyclopropyl | Cl | H | rac | H | H | | H | H | 1 | | H | H | H | H | O |
| 1.15 | N(CH$_3$)$_2$ | Cl | H | rac | H | H | | H | H | 2 | | H | H | H | H | — |
| 1.16 | N(H)-cyclopropyl | Cl | H | R | H | H | | H | H | 1 | | H | H | H | H | O |
| 1.17 | N(CH$_3$)$_2$ | Cl | H | R | H | H | | H | H | 1 | | H | H | H | H | O |
| 1.18 | N(H)-cyclopropyl | Cl | H | rac | H | H | | H | H | 1 | | CH$_3$ | H | F | H | O |
| 1.19 | N(H)CH$_3$ | Cl | H | rac | H | H | | H | H | 1 | | CH$_3$ | H | F | H | O |
| 1.20 | N(H)CH$_3$ | Cl | H | rac | H | H | | H | H | 1 | | H | H | H | H | O |
| 1.21 | NH$_2$ | C(O)OCH$_2$CH$_3$ | H | R | CH$_3$ | H | S | H | H | 1 | | H | H | CH$_3$ | H | — |
| 1.22 | NH$_2$ | CF$_3$ | H | R | H | H | | H | H | 2 | | H | H | H | H | — |
| 1.23 | NH$_2$ | CF$_3$ | H | R | CH$_3$ | H | S | H | H | 1 | | H | H | CH$_3$ | H | — |
| 1.24 | NH$_2$ | CF$_3$ | H | R | H | H | | H | H | 1 | | H | H | H | H | — |
| 1.25 | NH$_2$ | CN | H | R | CH$_3$ | H | S | H | H | 1 | | H | H | CH$_3$ | H | — |
| 1.26 | NH$_2$ | C(O)CH$_3$ | H | R | CH$_3$ | H | S | H | H | 1 | | H | H | CH$_3$ | H | — |
| 1.27 | NH$_2$ | C(O)OH | H | R | H | H | | H | H | 1 | | H | H | H | H | — |
| 1.28 | NH$_2$ | C(O)OH | H | R | H | H | | H | H | 2 | | H | H | H | H | — |
| 1.29 | NH$_2$ | C(O)CH$_3$ | H | R | H | H | | H | H | 1 | | H | H | H | H | — |
| 1.30 | NH$_2$ | C(O)CH$_3$ | H | R | H | H | | H | H | 2 | | H | H | H | H | — |
| 1.31 | NH$_2$ | CF$_3$ | H | R | H | H | | H | H | 1 | | H | H | CH$_3$ | H | — |
| 1.32 | NH$_2$ | C(O)OCH$_2$CH$_3$ | H | R | H | H | | H | H | 2 | | H | H | H | H | — |
| 1.33 | NH$_2$ | C(O)OCH$_2$CH$_3$ | H | R | H | H | | H | H | 1 | | H | H | H | H | — |
| 1.34 | NH$_2$ | C(O)N(H)CH$_3$ | H | R | H | H | | H | H | 2 | | H | H | H | H | — |
| 1.35 | NH$_2$ | C(O)N(H)CH$_3$ | H | rac | H | H | | H | H | 1 | | H | H | H | H | — |
| 1.36 | NH$_2$ | C(O)OH | H | R | CH$_3$ | H | S | H | H | 1 | | H | H | CH$_3$ | H | — |
| 1.37 | NH$_2$ | CN | H | R | H | H | | H | H | 2 | | H | H | H | H | — |
| 1.38 | NH$_2$ | CN | H | R | H | H | | H | H | 1 | | H | H | H | H | — |
| 1.39 | NH$_2$ | C(O)N(H)CH(CH$_3$)$_2$ | H | R | CH$_3$ | H | S | H | H | 1 | | H | H | CH$_3$ | H | — |
| 1.40 | NH$_2$ | C(O)N(CH$_3$)$_2$ | H | R | CH$_3$ | H | S | H | H | 1 | | H | H | CH$_3$ | H | — |
| 1.41 | NH$_2$ | C(O)N(H)CH$_3$ | H | R | CH$_3$ | H | S | H | H | 1 | | H | H | CH$_3$ | H | — |
| 1.42 | NH$_2$ | C(O)N(H)(CH$_2$)$_2$C(O)OEt | H | R | CH$_3$ | H | S | H | H | 1 | | H | H | CH$_3$ | H | — |
| 1.43 | NH$_2$ | C(O)N(H)CH$_2$C(O)OEt | H | R | CH$_3$ | H | S | H | H | 1 | | H | H | CH$_3$ | H | — |
| 1.44 | NH$_2$ | S(O)CH$_3$ | H | R | CH$_3$ | H | S | H | H | 1 | | H | H | CH$_3$ | H | — |
| 1.45 | NH$_2$ | S(O)$_2$CH$_3$ | H | R | CH$_3$ | H | S | H | H | 1 | | H | H | CH$_3$ | H | — |
| 1.46 | NH$_2$ | CF$_3$ | H | rac | H | H | | H | H | 2 | | H | F | H | H | — |
| 1.47 | NH$_2$ | CF$_3$ | H | rac | H | H | | H | H | 1 | | H | H | H | H | O |
| 1.48 | NH$_2$ | CF$_3$ | H | rac | H | H | | | | 0 | | H | H | H | H | O |
| 1.49 | NH$_2$ | CF$_3$ | H | rac | H | H | | H | H | 1 | | H | H | F | H | O |
| 1.50 | NH$_2$ | CF$_3$ | H | S | H | H | | H | H | 1 | | H | H | CH$_3$ | H | — |
| 1.51 | NH$_2$ | C(O)N(H)S(O)$_2$CH$_3$ | H | R | CH$_3$ | H | S | H | H | 1 | | H | H | CH$_3$ | H | — |
| 1.52 | NH$_2$ | CF$_3$ | H | R | H | H | | H | H | 2 | | H | H | CH$_3$ | H | — |
| 1.53 | NH$_2$ | C(O)N(H)S(O)$_2$CH$_2$CH$_2$CH$_3$ | H | R | CH$_3$ | H | S | H | H | 1 | | H | H | CH$_3$ | H | — |
| 1.54 | NH$_2$ | C(O)N(H)S(O)$_2$(4-Cl—Ph) | H | R | CH$_3$ | H | S | H | H | 1 | | H | H | CH$_3$ | H | — |
| 1.55 | NH$_2$ | C(O)N(H)S(O)$_2$Ph | H | R | CH$_3$ | H | S | H | H | 1 | | H | H | CH$_3$ | H | — |
| 1.56 | NH$_2$ | C(O)N(H)S(O)$_2$(4-NO$_2$—Ph) | H | R | CH$_3$ | H | S | H | H | 1 | | H | H | CH$_3$ | H | — |
| 1.57 | NH$_2$ | C(O)N(H)S(O)$_2$CF$_3$ | H | R | CH$_3$ | H | S | H | H | 1 | | H | H | CH$_3$ | H | — |
| 1.58 | NH$_2$ | Cl | H | rac | H | H | | H | H | 1 | | H | H | CH$_3$ | H | — |
| 1.59 | NH$_2$ | Cl | H | R | H | H | | H | H | 1 | | H | H | H | H | — |
| 1.60 | NH$_2$ | CN | H | rac | H | H | | H | H | 1 | | H | H | H | H | O |
| 1.61 | NH$_2$ | CN | H | S | H | H | | H | H | 1 | | H | H | CH$_3$ | H | — |
| 1.62 | NH$_2$ | CN | H | rac | H | H | | | | 0 | | H | H | H | H | O |
| 1.63 | NH$_2$ | CN | H | rac | H | H | | H | H | 2 | | H | F | H | H | — |

TABLE 1-continued

Examples of compounds of the general formula (I)

| No. | R$^1$ | R$^2$ | R$^3$ | St N R$^3$ | R$^4$ | R$^5$ | St R$^4$ R$^5$ | R$^6$ | R$^7$ | n | St R$^6$ R$^7$ | R$^8$ | R$^9$ | R$^{10}$ | R$^{11}$ | X |
|---|---|---|---|---|---|---|---|---|---|---|---|---|---|---|---|---|
| 1.64 | NH$_2$ | CN | H | rac | H | H | | H | H | 1 | | H | H | F | H | O |
| 1.65 | NH$_2$ | S(O)CH$_3$ | H | R | H | H | | H | H | 2 | | H | H | H | H | — |
| 1.66 | NH$_2$ | S(O)$_2$CH$_3$ | H | R | H | H | | H | H | 2 | | H | H | H | H | — |
| 1.67 | NH$_2$ | CF$_3$ | H | R | H | H | | H | H | 1 | | H | H | CH$_3$ | H | — |
| 1.68 | NH$_2$ | S(O)$_2$CH$_3$ | H | R | H | H | | H | H | 2 | | H | H | CH$_3$ | H | — |
| 1.69 | NH$_2$ | S(O)CH$_3$ | H | R | H | H | | H | H | 2 | | H | H | CH$_3$ | H | — |
| 1.70 | NH$_2$ | CN | H | R | H | H | | H | H | 1 | | H | H | CH$_3$ | H | — |
| 1.71 | NH$_2$ | S(O)CH$_3$ | H | R | H | H | | H | H | 1 | | H | H | CH$_3$ | H | — |
| 1.72 | NH$_2$ | C(O)CH$_3$ | H | R | H | H | | H | H | 1 | | H | H | CH$_3$ | H | — |
| 1.73 | NH$_2$ | S(O)$_2$CH$_3$ | H | R | H | H | | H | H | 1 | | H | H | CH$_3$ | H | — |
| 1.74 | NH$_2$ | C(O)OCH$_2$CH$_3$ | H | R | H | H | | H | H | 1 | | H | H | CH$_3$ | H | — |
| 1.75 | NH$_2$ | C(O)OH | H | R | H | H | | H | H | 1 | | H | H | CH$_3$ | H | — |
| 1.76 | NH$_2$ | C(O)N(H)CH$_3$ | H | R | H | H | | H | H | 1 | | H | H | CH$_3$ | H | — |
| 1.77 | NH$_2$ | C(O)N(CH$_3$)$_2$ | H | R | H | H | | H | H | 1 | | H | H | CH$_3$ | H | — |
| 1.78 | NH$_2$ | C(O)NH$_2$ | H | R | H | H | | H | H | 1 | | H | H | CH$_3$ | H | — |
| 1.79 | NH$_2$ | 4-Cl—Ph | H | R | CH$_3$ | H | S | H | H | 1 | | H | H | CH$_3$ | H | — |
| 1.80 | NH$_2$ | C(H)=CH$_2$ | H | R | CH$_3$ | H | S | H | H | 1 | | H | H | CH$_3$ | H | — |
| 1.81 | NH$_2$ | C(CF$_3$)=CH$_2$ | H | R | CH$_3$ | H | S | H | H | 1 | | H | H | CH$_3$ | H | — |
| 1.82 | NH$_2$ | CF$_3$ | H | S | OH | H | S | H | H | 1 | | H | H | H | H | — |
| 1.83 | NH$_2$ | CF$_3$ | H | R | OH | H | S | H | H | 1 | | H | H | H | H | — |
| 1.84 | NH$_2$ | CF$_3$ | H | rac | OH | H | rac | H | H | 1 | | H | H | H | H | — |
| 1.85 | NH$_2$ | CF$_3$ | H | rac | OMe | H | rac | H | H | 1 | | H | H | H | H | — |
| 1.86 | NH$_2$ | CF$_3$ | H | S | OMe | H | S | H | H | 1 | | H | H | H | H | — |
| 1.87 | NH$_2$ | S(O)$_2$CH$_3$ | H | S | OH | H | S | H | H | 1 | | H | H | H | H | — |
| 1.88 | NH$_2$ | S(O)$_2$CH$_3$ | H | rac | OH | H | rac | H | H | 1 | | H | H | H | H | — |
| 1.89 | NH$_2$ | S(O)$_2$CH$_3$ | H | rac | OMe | H | rac | H | H | 1 | | H | H | H | H | — |
| 1.90 | NH$_2$ | CN | H | S | OH | H | S | H | H | 1 | | H | H | H | H | — |
| 1.91 | NH$_2$ | CN | H | rac | OH | H | rac | H | H | 1 | | H | H | H | H | — |
| 1.92 | NH$_2$ | CN | H | rac | OMe | H | rac | H | H | 1 | | H | H | H | H | — |
| 1.93 | NH$_2$ | CF$_3$ | H | R | OMe | H | S | H | H | 1 | | H | H | H | H | — |
| 1.94 | NH$_2$ | S(O)$_2$CH$_3$ | H | R | OMe | H | S | H | H | 1 | | H | H | H | H | — |
| 1.95 | NH$_2$ | CN | H | R | OMe | H | S | H | H | 1 | | H | H | H | H | — |
| 1.96 | NH$_2$ | C(O)OCH$_2$CH$_3$ | H | R | OMe | H | S | H | H | 1 | | H | H | H | H | — |
| 1.97 | NH$_2$ | CF$_3$ | H | R | OMe | H | R | H | H | 1 | | H | H | H | H | — |
| 1.98 | NH$_2$ | S(O)$_2$CH$_3$ | H | R | OMe | H | R | H | H | 1 | | H | H | H | H | — |
| 1.99 | NH$_2$ | CN | H | R | OMe | H | R | H | H | 1 | | H | H | H | H | — |
| 1.100 | NH$_2$ | C(O)OCH$_2$CH$_3$ | H | R | OMe | H | R | H | H | 1 | | H | H | H | H | — |
| 1.101 | NH$_2$ | CH$_2$OH | H | R | CH$_3$ | H | S | H | H | 1 | | H | H | CH$_3$ | H | — |
| 1.102 | NH$_2$ | CH$_2$OH | H | R | H | H | | H | H | 1 | | H | H | CH$_3$ | H | — |
| 1.103 | NH$_2$ | CH(CH$_3$)OH | H | R | CH$_3$ | H | S | H | H | 1 | | H | H | CH$_3$ | H | — |
| 1.104 | NH$_2$ | CH(CH$_3$)OH | H | R | H | H | | H | H | 1 | | H | H | CH$_3$ | H | — |
| 1.105 | NH$_2$ | C(CH$_3$)$_2$OH | H | R | CH$_3$ | H | S | H | H | 1 | | H | H | CH$_3$ | H | — |
| 1.106 | NH$_2$ | C(CH$_3$)$_2$OH | H | R | H | H | | H | H | 1 | | H | H | CH$_3$ | H | — |
| 1.107 | H | C(CH$_3$)$_2$OH | H | R | CH$_3$ | H | S | H | H | 1 | | H | H | CH$_3$ | H | — |
| 1.108 | H | C(CH$_3$)$_2$OH | H | R | H | H | | H | H | 1 | | H | H | CH$_3$ | H | — |
| 1.109 | H | CH(CH$_3$)OH | H | R | CH$_3$ | H | S | H | H | 1 | | H | H | CH$_3$ | H | — |
| 1.110 | H | CH(CH$_3$)OH | H | R | H | H | | H | H | 1 | | H | H | CH$_3$ | H | — |
| 1.111 | H | C(CH$_3$)$_2$F | H | R | CH$_3$ | H | S | H | H | 1 | | H | H | CH$_3$ | H | — |
| 1.112 | H | C(CH$_3$)$_2$F | H | R | H | H | | H | H | 1 | | H | H | CH$_3$ | H | — |
| 1.113 | H | CH(CH$_3$)F | H | R | CH$_3$ | H | S | H | H | 1 | | H | H | CH$_3$ | H | — |
| 1.114 | H | CH(CH$_3$)F | H | R | H | H | | H | H | 1 | | H | H | CH$_3$ | H | — |
| 1.115 | H | S(O)$_2$CH$_3$ | H | R | CH$_3$ | H | S | H | H | 1 | | H | H | CH$_3$ | H | — |
| 1.116 | H | S(O)$_2$CH$_3$ | H | R | H | H | | H | H | 1 | | H | H | CH$_3$ | H | — |
| 1.117 | NH$_2$ | C(O)CF$_3$ | H | R | CH$_3$ | H | S | H | H | 1 | | H | H | CH$_3$ | H | — |
| 1.118 | NH$_2$ | C(O)CF$_3$ | H | R | H | H | | H | H | 1 | | H | H | CH$_3$ | H | — |
| 1.119 | NH$_2$ | CF$_3$ | H | R | CH$_3$ | H | S | H | H | 1 | | H | H | CH$_3$ | H | — |
| 1.120 | NH$_2$ | CF$_3$ | H | R | H | H | | H | H | 1 | | H | H | CH$_3$ | H | — |
| 1.121 | NH$_2$ | cyclopropyl | H | R | CH$_3$ | H | S | H | H | 1 | | H | H | CH$_3$ | H | — |
| 1.122 | NH$_2$ | CH(CH$_3$)F | H | R | CH$_3$ | H | S | H | H | 1 | | H | H | CH$_3$ | H | — |
| 1.123 | NH$_2$ | CH(CH$_3$)F | H | R | H | H | | H | H | 1 | | H | H | CH$_3$ | H | — |
| 1.124 | NH$_2$ | C(CH$_3$)$_2$F | H | R | CH$_3$ | H | S | H | H | 1 | | H | H | CH$_3$ | H | — |
| 1.125 | NH$_2$ | C(CH$_3$)$_2$F | H | R | H | H | | H | H | 1 | | H | H | CH$_3$ | H | — |
| 1.126 | H | C(CH$_3$)$_2$OCH$_3$ | H | R | CH$_3$ | H | S | H | H | 1 | | H | H | CH$_3$ | H | — |
| 1.127 | NH$_2$ | C(CH$_3$)$_2$OCH$_3$ | H | R | CH$_3$ | H | S | H | H | 1 | | H | H | CH$_3$ | H | — |
| 1.128 | H | C(CH$_3$)$_2$OCH$_3$ | H | R | H | H | | H | H | 1 | | H | H | CH$_3$ | H | — |
| 1.129 | NH$_2$ | C(CH$_3$)$_2$OCH$_3$ | H | R | H | H | | H | H | 1 | | H | H | CH$_3$ | H | — |
| 1.130 | H | CHF$_2$ | H | R | CH$_3$ | H | S | H | H | 1 | | H | H | CH$_3$ | H | — |
| 1.131 | NH$_2$ | CHF$_2$ | H | R | CH$_3$ | H | S | H | H | 1 | | H | H | CH$_3$ | H | — |
| 1.132 | H | CHF$_2$ | H | R | H | H | | H | H | 1 | | H | H | CH$_3$ | H | — |
| 1.133 | NH$_2$ | CHF$_2$ | H | R | H | H | | H | H | 1 | | H | H | CH$_3$ | H | — |
| 1.134 | H | CF$_3$ | H | R | CH$_3$ | H | S | H | H | 1 | | H | H | CH$_3$ | H | — |
| 1.135 | H | CF$_3$ | H | R | H | H | | H | H | 1 | | H | H | CH$_3$ | H | — |
| 1.136 | NH$_2$ | S(O)CH$_3$ | H | R | OMe | H | S | H | H | 1 | | H | H | H | H | — |
| 1.137 | NH$_2$ | S(O)$_2$CH$_3$ | H | R | OH | H | S | H | H | 1 | | H | H | H | H | — |
| 1.138 | NH$_2$ | S(O)CH$_3$ | H | R | OH | H | S | H | H | 1 | | H | H | H | H | — |

TABLE 1-continued

Examples of compounds of the general formula (I)

| No. | $R^1$ | $R^2$ | $R^3$ | St N $R^3$ | $R^4$ | $R^5$ | St $R^4 R^5$ | $R^6$ | $R^7$ | n | St $R^6 R^7$ | $R^8$ | $R^9$ | $R^{10}$ | $R^{11}$ | X |
|---|---|---|---|---|---|---|---|---|---|---|---|---|---|---|---|---|
| 1.139 | $NH_2$ | $S(O)CH_3$ | H | rac | OH | H | rac | H | H | 1 | | H | H | H | H | — |
| 1.140 | $NH_2$ | CN | H | R | OH | H | S | H | H | 1 | | H | H | H | H | — |
| 1.141 | $NH_2$ | C≡CH | H | R | $CH_3$ | H | S | H | H | 1 | | H | H | $CH_3$ | H | — |
| 1.142 | $NH_2$ | C≡CH | H | R | H | H | | H | H | 1 | | H | H | $CH_3$ | H | — |
| 1.143 | $NH_2$ | C≡CSi$(CH_3)_3$ | H | R | $CH_3$ | H | S | H | H | 1 | | H | H | $CH_3$ | H | — |
| 1.144 | $NH_2$ | C≡CSi$(CH_3)_3$ | H | R | H | H | | H | H | 1 | | H | H | $CH_3$ | H | — |
| 1.145 | $NH_2$ | OMe | H | R | $CH_3$ | H | S | H | H | 1 | | H | H | $CH_3$ | H | — |
| 1.146 | $NH_2$ | OMe | H | R | H | H | | H | H | 1 | | H | H | $CH_3$ | H | — |
| 1.147 | $NH_2$ | C≡$CCH_3$ | H | R | $CH_3$ | H | S | H | H | 1 | | H | H | $CH_3$ | H | — |
| 1.148 | $NH_2$ | C≡$CCH_3$ | H | R | H | H | | H | H | 1 | | H | H | $CH_3$ | H | — |
| 1.149 | H | $C(O)CH_3$ | H | R | $CH_3$ | H | S | H | H | 1 | | H | H | $CH_3$ | H | — |
| 1.150 | H | $C(O)CH_3$ | H | R | H | H | | H | H | 1 | | H | H | $CH_3$ | H | — |
| 1.151 | H | $C(CH_3)_2OH$ | H | R | $CH_3$ | H | S | H | H | 1 | | H | H | H | H | — |
| 1.152 | H | $C(CH_3)_2OH$ | H | R | H | H | | H | H | 1 | | H | H | H | H | — |
| 1.153 | H | $C(CH_3)_2OH$ | H | R | H | H | | H | H | 2 | | H | H | H | H | — |
| 1.154 | H | $C(CH_3)_2OH$ | H | rac | H | H | | H | H | 1 | | H | H | H | H | O |
| 1.155 | H | $C(CH_3)_2OH$ | H | R | H | H | | H | H | 1 | | H | H | $CH_2CH_3$ | H | — |
| 1.156 | H | $C(CH_3)_2OH$ | H | S | OH | H | S | H | H | 1 | | H | H | H | H | — |
| 1.157 | H | $C(CH_3)_2OH$ | H | S | $OCH_3$ | H | S | H | H | 1 | | H | H | H | H | — |
| 1.158 | H | $C(CH_3)_2OH$ | H | R | H | H | | H | H | 2 | $OCH_3$ | H | H | H | — |
| 1.159 | H | $C(CH_3)_2OH$ | H | R | H | H | | H | H | 2 | $CH_3$ | H | H | H | — |
| 1.160 | H | $C(CH_3)_2OH$ | H | R | H | H | | H | H | 2 | | H | H | $CH_3$ | H | — |
| 1.161 | H | $C(CH_3)_2OH$ | H | R | $CH_3$ | H | S | H | H | 2 | | H | H | $CH_2CH_3$ | H | — |
| 1.162 | H | $C(CH_3)_2OH$ | H | R | H | H | | H | H | 2 | | F | H | H | H | — |
| 1.163 | H | $C(CH_3)_2OH$ | H | R | H | H | | H | H | 1 | | H | H | $CH_3$ | H | O |
| 1.164 | H | $C(CH_3)_2OH$ | H | rac | H | H | | H | H | 1 | | H | H | F | H | O |
| 1.165 | H | $C(CH_3)_2OH$ | H | rac | H | H | | | | 0 | | H | H | H | H | O |
| 1.166 | H | $C(CH_3)_2OH$ | H | R | H | H | | H | H | 2 | | H | H | F | H | — |
| 1.167 | H | $C(CH_3)_2OH$ | H | R | H | H | | H | H | 1 | | H | H | F | H | — |
| 1.168 | H | $C(CH_3)_2OH$ | H | R | H | H | | H | H | 2 | | H | H | $CH_2CH_3$ | H | — |
| 1.169 | $NH_2$ | $S(O)_2CH_3$ | H | R | H | H | | H | H | 2 | $CH_3$ | H | H | H | — |
| 1.170 | $NH_2$ | $CF_3$ | H | R | H | H | | H | H | 2 | $CH_3$ | H | H | H | — |
| 1.171 | $NH_2$ | $S(O)_2CH_3$ | H | rac | H | H | | H | H | 2 | $CH_3$ | H | H | H | — |
| 1.172 | $NH_2$ | $CF_3$ | H | rac | H | H | | H | H | 2 | $CH_3$ | H | H | H | — |

The present invention further provides processes for preparing corresponding compounds of the general formula (I) and/or salts thereof and/or agrochemically acceptable quaternized nitrogen derivatives thereof:

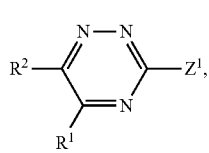
(I)

in which the $R^1$ to $R^{11}$ and X radicals and n have the above meanings, and where according to a first process a) a compound of the general formula (II)

(II)

$$R^2 \underset{R^1}{\overset{N-N}{\diagdown}} Z^1$$

where $R^1$, $R^2$ have the meaning given above and $Z^1$ represents an exchangeable radical or a leaving group, is reacted with an amine of the general formula (III) or an acid addition salt of the amine of the general formula (III)

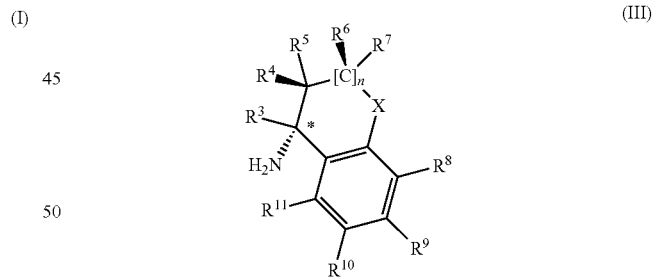
(III)

where the $R^3$ to $R^{11}$ and X radicals and n have the above meaning.

The exchangeable radical $Z^1$ or the leaving group $Z^1$ represents fluorine, chlorine, bromine, iodine, a $(C_1-C_4)$-alkylsulfanyl or a $(C_1-C_4)$-alkylsulfinyl or a $(C_1-C_4)$-alkylsulfonyl, an unsubstituted phenyl-$(C_1-C_4)$-alkylsulfonyl or a phenyl-$(C_1-C_4)$-alkylsulfonyl which is mono- or polysubstituted by fluorine, chlorine, bromine or $(C_1-C_4)$-alkyl or $(C_1-C_4)$-alkoxy or represents a $(C_1-C_4)$-alkylphenylsulfonyl.

If necessary, a $Z^1$ radical can be converted into another group of better exchangeability. For example, in the context of a two-stage one-pot method, a $(C_1-C_4)$-alkylsulfanyl can be converted with an oxidizing agent such as m-chloroperbenzoic acid or Oxone® into a $(C_1-C_4)$-alkylsulfinyl or a $(C_1-C_4)$-alkylsulfonyl or mixtures thereof, and then reacted with an amine of the general formula (III) or an acid addition salt using an auxiliary base, for example triethylamine or potassium carbonate.

The reaction may optionally also be catalyzed by various auxiliaries, for example by the reagents potassium phosphate, copper(I) iodide and N,N-diethyl-2-hydroxybenzamide, or in the manner of a Buchwald-Hartwig coupling by special transition metal catalyst systems.

The compounds of the general formula (II) are commercially available or can be prepared by known methods. Substituted 1,2,4-triazines of the general formula (II) are a class of compounds that is very familiar to the person skilled in the art. There is a large number of different synthesis methods of general applicability (for a review, see, for example, Houben-Weyl Methods of Organic Chemistry, 4th Edition (1997), Vol. E 9c, Hetarenes IV, pages 582-666 and the literature cited therein).

The amines of the general formula (III) or the acid addition salt thereof are commercially available, or the synthesis thereof is described in WO 2004/069814 A1.

b.) Compounds of the general formula (I) can also be prepared by initially preparing a compound of the general formula (II-a),

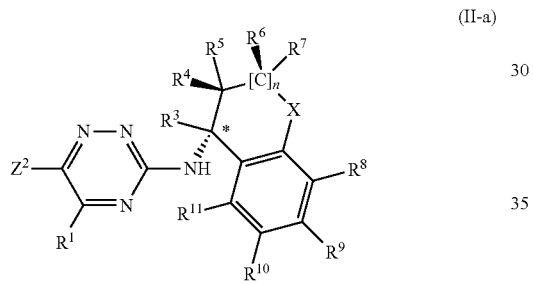

where $Z^2$ represents a radical from the group consisting of halogen, cyano, $(C_1-C_6)$-alkoxycarbonyl, $(C_1-C_6)$-alkylcarbonyl and $(C_1-C_6)$-alkylthio which can be modified or exchanged, by the process described under a).

Thus, for example, in the case that $Z^2$ represents cyano, the cyano group can be hydrolyzed with bases such as aqueous sodium hydroxide solution or potassium hydroxide to give carboxamides.

In the case that $Z^2$ represents a halogen atom, preferably chlorine, it can be reacted, for example, with alcohols, optionally using additional bases such as sodium, sodium hydride or the alkoxide of the alcohol in question, to give alkoxy derivatives in position $R^2$.

In the case that $Z^2$ represents halogen, preferably bromine or iodine, it can be reacted, for example, under palladium catalysis with aromatic, heteroaromatic or aliphatic boronic acids (Suzuki reaction) or with alkenes or alkynes to give the corresponding target structures of the formula (I).

In the case that $Z^2$ represents $(C_1-C_6)$-alkylthio, this group can be converted with an oxidizing agent such as m-chloroperbenzoic acid or Oxone® into a $(C_1-C_6)$-alkylsulfinyl or a $(C_1-C_6)$-alkylsulfonyl.

In the case that $Z^2$ represents $(C_1-C_6)$-alkoxycarbonyl, these esters can be hydrolyzed, for example, with bases such as aqueous sodium hydroxide solution or potassium hydroxide to give the carboxylic acids [formula 1, $R^2=C(O)OH$]. For their part, the resulting carboxylic acids can in turn be reacted, for example, with amines using auxiliary reagents such as propanephosphonic anhydride (T3P) to give substituted carboxamides in position $R^2$. The resulting carboxylic acids can also be converted, for example, into carbonyl chlorides and then be reacted with amines to give substituted carboxamides in position $R^2$.

In the case that $Z^2$ represents $(C_1-C_6)$-alkoxycarbonyl, these esters can be reacted, for example, with Grignard reagents ($R^4$MgHal) to give the corresponding alcohols [formula 1, $R^2=C(R^4)_2OH$].

In the case that $Z^2$ represents $(C_1-C_6)$-alkylcarbonyl, these ketones can be reacted, for example, with Grignard reagents ($R^4$MgHal) to give the corresponding alcohols [formula 1, $R^2=C[(C_1-C_6)\text{-alkyl}](R^4)OH$].

If necessary, a $Z^2$ radical can also be converted to another $Z^2$ radical first. Thus, for example, using the processes described above, first an intermediate of type (II-a) may be prepared in which the $Z^2$ radical represents halogen, preferably chlorine, which can be converted with nucleophiles, for example sodium cyanide, into the nitrile ($Z^2$=cyano) or, for example, with mercaptans, optionally using additional bases such as sodium, sodium hydride or the thiolate of the thiol in question, into compounds where $Z^2=(C_1-C_6)$-alkylthio.

c.) Compounds of the general formula (I) in which $R^1$ represents amino can also be prepared by condensing guanidines of type (IV) or acid addition salts thereof

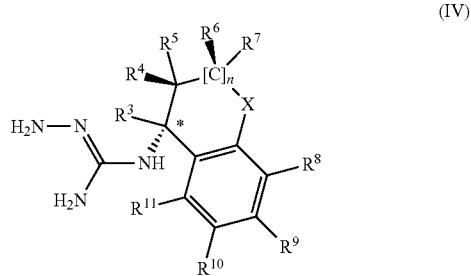

with acylcyanides of the formula (V)

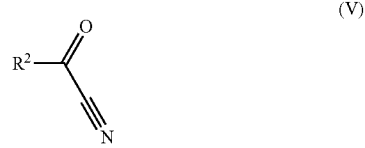

(see, for example, Houben-Weyl Methods of Organic Chemistry, 4th Edition (1997), Vol. E 9c, Hetarenes IV, page 597; Chem. Ber. 1960, 93, 2209).

d.) Compounds of the general formula (II) in which the $Z^1$ radical represents $(C_1-C_4)$-alkylthio and the $R^1$ radical represents amino can be prepared analogously to the process described under c.) using instead of (IV) S—$(C_1-C_4)$-alkyl isothiosemicarbazides or acid addition salts thereof of the general formula (IVa)

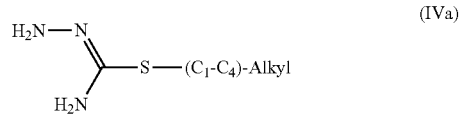

(see, for example, Houben-Weyl Methods of Organic Chemistry, 4th Edition (1997), Vol. E 9c, Hetarenes IV, page 597; Bull. Chem. Soc. Jpn. 1978, 51, 1846).

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from Teledyne ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, compounds of the general formula (I) and salts thereof can be prepared completely or partially by solid-phase-supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid-phase-supported synthesis methods permits a number of protocols, which are known from the literature and which for their part may be performed manually or in an automated manner.

Both in the solid and in the liquid phase, the implementation of individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

On account of the herbicidal property of the compounds of the general formula (I), the invention also further provides for the use of the compounds of the general formula (I) according to the invention as herbicides for control of harmful plants.

Herbicides are used in agriculturally utilized crops during various cultivation phases. Thus, the application of some products even takes place before or during sowing. Others are applied before the crop plant emerges, i.e. before the seedling breaks through the earth's surface (pre-emergence herbicides). Finally, post-emergence herbicides are used if either already the seed leaves or foliage leaves have been formed by the crop plant.

The compounds of the invention can be employed either pre-emergence or post-emergence, preference being given to pre-emergence use of the compounds of the invention.

The pre-emergence treatment includes both the treatment of the area under cultivation prior to sowing (ppi=pre plant incorporation) and the treatment of the sown areas of cultivation which do not yet sustain any growth.

The compounds of the formula (I) according to the invention and their salts, also referred to synonymously and collectively hereinafter as compounds of the formula (I), have excellent herbicidal efficacy against a broad spectrum of economically important monocotyledonous and dicotyledonous harmful plants. The active compounds also have good control over perennial weeds which are difficult to control and produce shoots from rhizomes, root stocks or other perennial organs. It does not matter here whether the substances are applied by the presowing method, the pre-emergence method or the post-emergence method.

Specific examples of some representatives of the monocotyledonous and dicotyledonous weed flora which can be controlled by the compounds of the general formula (I) according to the invention are mentioned, without any intention that the enumeration is to impose a restriction to particular species.

On the side of the monocotyledonous weed species, e.g. *Agrostis, Alopecurus, Apera, Avena, Brachicaria, Bromus, Dactyloctenium, Digitaria, Echinochloa, Eleocharis, Eleusine, Festuca, Fimbristylis, Ischaemum, Lolium, Monochoria, Panicum, Paspalum, Phalaris, Phleum, Poa, Sagittaria, Scirpus, Setaria, Sphenoclea*, and also *Cyperus* species predominantly from the annual group and on the sides of the perennial species *Agropyron, Cynodon, Imperata* and *Sorghum* and also perennial *Cyperus* species are well controlled.

On the side of the dicotyledonous weed species, the activity spectrum extends, for example, to species such as *Galium, Viola, Veronica, Lamium, Stellaria, Amaranthus, Sinapis, Ipomoea, Matricaria, Abutilon* and *Sida* on the annual side, and *Convolvulus, Cirsium, Rumex* and *Artemisia* in the case of the perennial weeds. Moreover, herbicidal action is observed in the case of dicotyledonous weeds such as *Ambrosia, Anthemis, Carduus, Centaurea, Chenopodium, Cirsium, Convolvulus, Datura, Emex, Galeopsis, Galinsoga, Lepidium, Lindernia, Papaver, Portlaca, Polygonum, Ranunculus, Rorippa, Rotala, Seneceio, Sesbania, Solanum, Sonchus, Taraxacum, Trifolium, Urtica* and *Xanthium*.

If the compounds of the general formula (I) according to the invention are applied to the soil surface before germination, either the emergence of the weed seedlings is prevented completely or the weeds grow until they have reached the cotyledon stage, but then they stop growing and ultimately die completely after three to four weeks have passed.

If the active compounds of the general formula (I) are applied post-emergence to the green parts of the plants, growth likewise stops sharply very rapidly after the treatment, and the weed plants remain at the growth stage at the time of application or die completely after a certain time, such that competition by the weeds, which is harmful to the crop plants, is thus eliminated very early and in a lasting manner.

Although the compounds of the general formula (I) according to the invention have excellent herbicidal activity in respect of monocotyledonous and dicotyledonous weeds, crop plants of economically important crops, for example wheat, barley, rye, rice, corn, sugar beet, cotton, oilseed rape and soybean, are only damaged negligibly, if at all. This is why the present compounds are highly suitable for the selective control of unwanted plant growth in agriculturally useful plants.

In addition, the substances of the general formula (I) according to the invention have excellent growth regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since this can reduce or completely prevent lodging.

By virtue of their herbicidal and plant growth regulatory properties, the active compounds can also be used to control harmful plants in crops of genetically modified plants which are known or are yet to be developed. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or those with a different fatty acid composition in the harvested material. Other particular properties may be tolerance or resistance to abiotic stressors, for example heat, low temperatures, drought, salinity and ultraviolet radiation.

It is preferable to employ the compounds of the general formula (I) according to the invention or salts thereof in economically important transgenic crops of useful plants and ornamental plants, for example of cereals such as wheat, barley, rye, oats, sorghum and millet, rice, cassava and corn or else crops of sugar beet, cotton, soybean, oilseed rape, potato, tomato, peas and other vegetables.

It is preferable to employ the compounds of the general formula (I) as herbicides in crops of useful plants which are resistant, or have been made resistant by recombinant means, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods (see, for example, EP 0221044, EP 0131624). For example, there have been descriptions in several cases of:

genetic modifications of crop plants for the purpose of modifying the starch synthesized in the plants (for example WO 92/011376, WO 92/014827, WO 91/019806), transgenic crop plants which are resistant to certain herbicides of the glufosinate type (cf., for example, EP 0242236, EP 0242246) or the glyphosate type (WO 92/000377) or the sulfonylurea type (EP 0257993, U.S. Pat. No. 5,013,659), transgenic crop plants, for example cotton, which is capable of producing *Bacillus thuringiensis* toxins (Bt toxins), which make the plants resistant to certain pests (EP 0142924, EP 0193259), transgenic crop plants having a modified fatty acid composition (WO 91/013972), genetically modified crop plants with novel constituents or secondary metabolites, for example novel phytoalexins, which bring about an increased disease resistance (EP 0309862, EP 0464461), genetically modified plants having reduced photorespiration, which have higher yields and higher stress tolerance (EP 0305398), transgenic crop plants which produce pharmaceutically or diagnostically important proteins ("molecular pharming"), transgenic crop plants which feature higher yields or better quality, transgenic crop plants which feature a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431).

For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To join the DNA fragments with one another, adapters or linkers can be placed onto the fragments, see, for example, Sambrook et al., 1989, Molecular Cloning, A Laboratory Manual, 2nd edition Cold Spring Harbor Laboratory Press, Cold Spring Harbor, N.Y., or Winnacker "Gene and Klone [Genes and clones]", VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl.

Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

It is preferable to use the compounds of the general formula (I) according to the invention in transgenic crops which are resistant to growth regulators, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active compounds.

When the active compounds of the general formula (I) according to the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the general formula (I) according to the invention as herbicides for control of harmful plants in transgenic crop plants.

The compounds of the general formula (I) can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", M C Publ. Corp., Ridgewood N.J.; Sisley and Wood, "Encyclopedia of Surface Active Agents", Chem. Publ. Co. Inc., N.Y. 1964, Schönfeldt, "Grenzflächenaktive Äthylenoxidaddukte [Interface-active ethylene oxide adducts]", Wiss. Verlagsgesell., Stuttgart 1976, Winnacker-Küchler, "Chemische Technologie [Chemical Technology]", Volume 7, C. Hanser Verlag Munich, 4th Ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the active herbicidal compounds are finely ground, for example in customary apparatuses such as hammer mills, blower mills and air-jet mills, and simultaneously or subsequently mixed with the formulation auxiliaries.

Emulsifiable concentrates are prepared by dissolving the active compound in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophillite, or diatomaceous earth.

Suspension concentrates may be water- or oil-based. They can be produced, for example, by wet grinding by means of standard commercial bead mills and optionally the addition of surfactants, as have already been listed above, for example, for the other types of formulation.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be produced either by spraying the active compound onto adsorptive granular inert material or by applying active compound concentrates to the surface of carriers, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London, J. E. Browning, "Agglomeration", Chemical and Engineering 1967, pages 147 ff; "Perry's Chemical Engineer's Handbook", 5th Ed., McGraw Hill, New York 1973, p. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1% to 99% by weight, especially 0.1% to 95% by weight, of active compound of the formula (I).

In wettable powders, the active compound concentration is, for example, about 10% to 90% by weight, the remainder to 100% by weight consisting of customary formulation components. In emulsifiable concentrates, the active compound concentration may be about 1% to 90% and preferably 5% to 80% by weight. Formulations in the form of dusts comprise 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is present in liquid or solid form and on which granulation auxiliaries, fillers, etc., are used. In the water-dispersible granules, the content of active compound is, for example, between 1% and 95% by weight, preferably between 10% and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

The compounds of the general formula (I) or salts thereof can be used as such or in the form of their preparations (formulations) in a combination with other pesticidally active substances, for example insecticides, acaricides, nematicides, herbicides, fungicides, safeners, fertilizers and/or growth regulators, for example in the form of a finished formulation or of a tank mix.

For application, the formulations in the commercial form are diluted if appropriate in a customary manner, for example with water in the case of wettable powders, emulsifiable concentrates, dispersions and water-dispersible granules. Dust-type preparations, granules for soil application or granules for scattering and sprayable solutions are not normally diluted further with other inert substances prior to application.

The required application rate of the compounds of the general formula (I) varies according to the external conditions such as, inter alia, temperature, humidity and the type of herbicide used. It can vary within wide limits, for example between 0.001 and 10.0 kg/ha or more of active substance, but it is preferably between 0.005 and 5 kg/ha.

The present invention is illustrated in detail by the examples which follow, but these examples do not restrict the invention in any way.

A. SYNTHESIS EXAMPLES

6-Chloro-$N^3$-[(1R,2S)-2,6-dimethyl-2,3-dihydro-1H-inden-1-yl]-1,2,4-triazine-3,5-diamine (Ex. 1.3)

In a microwave oven, 1.100 g (6.667 mmol) of 3,6-dichloro-1,2,4-triazine-5-amine, 1.290 g (8.001 mmol) of (1R,2S)-2,6-dimethylindane-1-amine and 5.210 g (26.669 mmol) of dicyclohexylmethylamine in 10.0 ml of 1-methylpyrrolidin-2-one were heated at 160° C. for 1 h. The mixture was poured into water and extracted three times with ethyl acetate. The combined organic phases were washed successively four times with water and once with saturated aqueous sodium chloride solution and dried over sodium sulfate, the solvent was distilled off under reduced pressure and the residue was purified by chromatography (start: ethyl acetate/n-heptane (5:95), over 30 min to ethyl acetate/n-heptane (60:40). Crystallization of the crude product from a mixture of ethyl acetate and n-heptane (4:1) gave 1.210 g (44%) of 6-chloro-$N^3$-[(1R,2S)-2,6-dimethyl-2,3-dihydro-1H-inden-1-yl]-1,2,4-triazine-3,5-diamine.

6-(4-Chlorophenyl)-$N^3$-[(1R,2S)-2,6-dimethyl-2,3-dihydro-1H-inden-1-yl]-1,2,4-triazine-3,5-diamine (Ex. 1.79)

To a solution of 0.150 g (0.518 mmol) of 6-chloro-$N^3$-[(1R,2S)-2,6-dimethyl-2,3-dihydro-1H-inden-1-yl]-1,2,4-triazine-3,5-diamine (see above, Ex. 1.3) in 4.0 ml of 1,2-dimethoxyethane, 0.185 g (0.776 mmol) of 2-(4-chlorophenyl)-4,4,5,5-tetramethyl-1,3,2-dioxaborolane, 0.018 g (0.026 mmol) of bis(triphenylphosphine)palladium(II) chloride and 0.414 ml (1.035 mmol) of a 2.5 molar aqueous cesium carbonate solution were added in succession under argon. In a microwave oven, the mixture was heated at 80° C. for 3 h. Water and ethyl acetate were added and the aqueous phase was washed twice with ethyl acetate. The combined organic phases were dried over sodium sulfate, the solvent was then distilled off under reduced pressure and the residue was purified by chromatography [start: ethyl acetate/n-heptane (5:95), over 25 min to ethyl acetate/n-heptane (50:50)]. This gave 0.153 g (81%) of 6-(4-chlorophenyl)-$N^3$-[(1R,2S)-2,6-dimethyl-2,3-dihydro-1H-inden-1-yl]-1,2,4-triazine-3,5-diamine.

Ethyl 5-amino-3-[(1R)-1,2,3,4-tetrahydronaphthalen-1-ylamino]-1,2,4-triazine-6-carboxylate (Ex. 1.32)

0.759 g (3.081 mmol) of meta-chloroperbenzoic acid dissolved in 20 ml of trichloromethane was added dropwise to a solution of 0.300 g (1.400 mmol) of ethyl 5-amino-3-(methylsulfanyl)-1,2,4-triazine-6-carboxylate in 20 ml of trichloromethane. The mixture was stirred at 0° C. for 1 h, and 0.543 g (4.201 mmol) of N,N-diisopropylethylamine and 0.309 g (2.100 mmol) of (1R)-1,2,3,4-tetrahydronaphthalen-1-amine dissolved in 2 ml trichloromethane were added in succession. The mixture was stirred at 50° C. for 2 h, water and dichloromethane were added and the aqueous phase was extracted twice with dichloromethane. The combined organic phases were dried over sodium sulfate, the solvent was then removed under reduced pressure and the residue was taken up in acetonitrile. The insoluble residue (3-chlorobenzoic acid) was filtered off and the solvent was then removed under reduced pressure, giving, after purification of the residue by chromatography [start: ethyl acetate/n-heptane (5:95), over 60 min to ethyl acetate/n-heptane (45:55)], 0.338 g (73%) of ethyl 5-amino-3-[(1R)-1,2,3,4-tetrahydronaphthalen-1-ylamino]-1,2,4-triazine-6-carboxylate.

5-Amino-3-[(1R)-1,2,3,4-tetrahydronaphthalen-1-ylamino]-1,2,4-triazine-6-carboxylic acid (Ex. 1.28)

0.245 g (0.782 mmol) of ethyl 5-amino-3-[(1R)-1,2,3,4-tetrahydronaphthalen-1-ylamino]-1,2,4-triazine-6-carboxylate (see above, Ex. 1.32) were taken up in 6 ml of methanol and added to a solution of 0.263 g (4.691 mmol) of potassium hydroxide in 6 ml of water. The mixture was heated under reflux for 2 hours. After removal of the alcohols under reduced pressure, the aqueous solution that remained was adjusted to pH 2 using concentrated hydrochloric acid. Filtration and drying of the precipitate formed gave 0.169 g (72%) of 5-amino-3-[(1R)-1,2,3,4-tetrahydronaphthalen-1-ylamino]-1,2,4-triazine-6-carboxylic acid as a colorless solid.

5-Amino-N-methyl-3-[(1R)-1,2,3,4-tetrahydronaphthalen-1-ylamino]-1,2,4-triazine-6-carboxamide (Ex. 1.34)

At 0° C., 0.377 g (0.592 mmol) of propanephosphonic anhydride (T3P, 50% strength solution in tetrahydrofuran) was added to a solution of 0.130 g (0.456 mmol) of 5-amino-3-[(1R)-1,2,3,4-tetrahydronaphthalen-1-ylamino]-1,2,4-triazine-6-carboxylic acid (see above, Ex. 1.28), 0.017 g (0.547 mmol) of methanamine (2 molar solution in tetrahydrofuran) and 0.138 g (1.367 mmol) of triethylamine in 5 ml of dichloromethane, and the mixture was stirred at 25° C. for 12 h. Water was added to the mixture and the aqueous phase was extracted twice with dichloromethane. The combined organic phases were dried over sodium sulfate, the solvent was then distilled off under reduced pressure and the residue was purified by chromatography [start: ethyl acetate/n-heptane (5:95), over 40 min to 100% ethyl acetate], giving 0.015 (11%) of 5-amino-N-methyl-3-[(1R)-1,2,3,4-tetrahydronaphthalen-1-ylamino]-1,2,4-triazine-6-carboxamide.

1-[5-Amino-3-[(1R)-2,3-dihydro-1H-inden-1-ylamino]-1,2,4-triazin-6-yl]ethanone (Ex. 1.29)

1. 0.785 g (18.692 mmol) of lithium hydroxide was added to a solution of 1.000 g (4.673 mmol) of ethyl 5-amino-3-(methylsulfanyl)-1,2,4-triazine-6-carboxylate in 20 ml of tetrahydrofuran, and the mixture was stirred at 25° C. for 4 h. The solvent was removed under reduced pressure, 20 ml of water were added to the residue and the pH was adjusted to 4 using 4N hydrochloric acid. Filtration and drying of the precipitate formed gave 0.800 g (90%) of 5-amino-3-(methylsulfanyl)-1,2,4-triazine-6-carboxylic acid as a colorless solid.
2. Successively, 1.79 ml of triethylamine, 0.781 g (5.106 mmol) of 1-hydroxybenzotriazole (HOBt), 0.975 g (5.106 mmol) of N'-(3-dimethylaminopropyl)-N-ethylcarbodiimide hydrochloride (EDC×HCl) and 0.500 g (5.106 mmol) of N-methoxymethanamine were added to a solution of 0.800 g (4.255 mmol) of 5-amino-3-(methylsulfanyl)-1,2,4-triazine-6-carboxylic acid in 10 ml of dimethylformamide, and the mixture was stirred at 25° C. for 16 h. 20 ml of water were added to the mixture and the aqueous phase was extracted three times with ethyl acetate. After drying of the combined organic phases over sodium sulfate, the solvent was distilled off under reduced pressure giving 0.870 g (88%) of 5-amino-N-methoxy-N-methyl-3-(methylsulfanyl)-1,2,4-triazine-6-carboxamide as a yellow oil.
3. At 0° C., 6.67 ml (12.987 mmol) of methylmagnesium bromide (1 molar solution in THF) were added to a solution of 0.600 g (2.597 mmol) of 5-amino-N-methoxy-N-methyl-3-(methylsulfanyl)-1,2,4-triazine-6-carboxamide in 10 ml of tetrahydrofuran, and the mixture was stirred at 25° C. for 5 h. Saturated aqueous ammonium chloride solution was added dropwise to the mixture and the aqueous phase was extracted three times with ethyl acetate. The combined organic phases were dried over sodium sulfate, the solvent was then distilled off under reduced pressure and the residue was purified by chromatography [ethyl acetate/n-hexane (20:80)], giving 0.200 g (41%) of 1-[5-amino-3-(methylsulfanyl)-1,2,4-triazin-6-yl]ethanone. $^1$H-NMR (400 MHz in CDCl$_3$): δ=2.54 (3H, s), 2.62 (3H, s), 8.20 (1H, bs), 8.52 (1H, bs).
4. At 0° C., 0.442 g (1.791 mmol) of meta-chloroperbenzoic acid dissolved in 20 ml of trichloromethane was added dropwise to a solution of 0.150 g (0.814 mmol) of 1-[5-amino-3-(methylsulfanyl)-1,2,4-triazin-6-yl]ethanone in 40 ml of trichloromethane. The mixture was stirred at 20° C. for 1 h, and 0.316 g (2.443 mmol) of N,N-diisopropylethylamine and 0.163 g (1.221 mmol) of (1R)-indane-1-amine dissolved in 2 ml of trichloromethane were added in succession. The mixture was stirred at 50° C. for 2 h, water and dichloromethane were added and the aqueous phase was extracted twice with dichloromethane. The combined organic phases were dried over sodium sulfate, the solvent was then removed under reduced pressure and the residue was taken up in acetonitrile. The insoluble residue (3-chlorobenzoic acid) was filtered off and the solvent was then removed under reduced pressure, giving, after purification of the residue by chromatography [start: ethyl acetate/n-heptane (5:95), over 60 min to ethyl acetate/n-heptane (45:55)], 0.108 g (49%) of 1-{5-amino-3-[(1R)-2,3-dihydro-1H-inden-1-ylamino]-1,2,4-triazin-6-yl}ethanone (Ex. 1.29).

N$^3$-(3,4-Dihydro-2H-chromen-4-yl)-6-(trifluoromethyl)-1,2,4-triazine-3,5-diamine (Ex. 1.47)

1. 25 ml of a saturated aqueous ammonium hydroxide solution were added to a solution of 18.00 g (42.92 mmol) of 5-chloro-3-(methylsulfanyl)-6-(trifluoromethyl)-1,2,4-triazine in 33 ml of 1,4-dioxane, and the mixture was stirred at 25° C. for 10 min. 150 ml of water were added. Filtration and washing of the solid formed with water and n-hexane gave 14.6 g (88%) of 3-(methylsulfanyl)-6-(trifluoromethyl)-1,2,4-triazine-5-amine as a brown solid. $^1$H-NMR (400 MHz in CDCl$_3$): δ=2.61 (3H, s), 5.51 (2H, bs).
2. 0.250 g (1.130 mmol) of 3-(methylsulfanyl)-6-(trifluoromethyl)-1,2,4-triazine-5-amine and 0.337 g (2.260 mmol) of chroman-4-amine in 2.0 ml of 1-methylpyrrolidin-2-one are heated at 180° C. for 30 h. The solvent was removed under high vacuum, the residue was taken up in ethyl acetate and water and the aqueous phase was extracted three times with ethyl acetate. The combined organic phases were washed successively once with water and once with saturated aqueous sodium chloride solution and dried over sodium sulfate, the solvent was distilled off under reduced pressure and the residue was purified by chromatography (acetonitrile/water). Under reduced pressure, the acetonitrile was removed from the product fraction, the aqueous solution that remained was adjusted to pH 9 using saturated aqueous sodium carbonate solution and the mixture was extracted three times with dichloromethane. After drying of the combined organic phases over sodium sulfate, the solvent was distilled off under reduced pressure giving 0.035 g (10%) of $N^3$-(3,4-dihydro-2H-chromen-4-yl)-6-(trifluoromethyl)-1,2,4-triazine-3,5-diamine (Ex. 1.47).

NMR Data of Selected Examples

NMR Peak List Method

The 1H-NMR data of selected examples are noted in the form of 1H-NMR peak lists. For each signal peak, first the δ value in ppm and then the signal intensity in round brackets are listed. The pairs of δ value-signal intensity numbers for different signal peaks are listed with separation from one another by semicolons.

The peak list of an example therefore takes the form of:
$\delta_1$ (intensity$_1$); $\delta_2$ (intensity$_2$); ... ; $\delta_i$ (intensity$_i$); ... ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form the subject-matter of the invention, and/or peaks of impurities.

In the reporting of compound signals in the delta range of solvents and/or water, our lists of 1H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

Example 1.1: $^1$H-NMR (400.1 MHz, CDCl$_3$): δ=7.517 (0.5); 7.400 (3.3); 7.383 (4.1); 7.378 (4.2); 7.259 (82.8); 7.254 (7.8); 7.206 (0.9); 7.201 (1.4); 7.188 (3.6); 7.183 (4.5); 7.175 (3.8); 7.172 (8.0); 7.169 (7.2); 7.166 (6.8); 7.157 (3.7); 7.152 (4.3); 7.138 (1.5); 7.134 (1.1); 7.122 (4.5); 7.116 (4.6); 7.106 (2.1); 7.103 (2.5); 7.100 (2.8); 6.995 (0.5); 5.570 (2.2); 5.296 (16.0); 5.245 (0.6); 5.225 (0.5); 3.371 (0.5); 3.196 (0.6); 2.896 (0.7); 2.881 (1.3); 2.865 (0.8); 2.854 (1.9); 2.839 (3.6); 2.823 (2.4); 2.813 (3.0); 2.796 (4.8); 2.780 (3.6); 2.754 (1.3); 2.738 (0.9); 2.714 (0.4); 2.149 (0.5); 2.138 (0.8); 2.127 (1.0); 2.116 (1.7); 2.105 (2.0); 2.094 (1.8); 2.085 (1.6); 2.073 (1.3); 2.015 (1.0); 2.002 (1.6); 1.987 (1.5); 1.980 (1.5); 1.970 (1.4); 1.965 (1.4); 1.957 (1.2); 1.950 (1.4); 1.938 (1.5); 1.931 (1.5); 1.923 (1.4); 1.916 (2.0); 1.906 (1.5); 1.896 (2.3); 1.887 (1.8); 1.881 (2.1); 1.872 (2.2); 1.864 (1.8); 1.861 (1.8); 1.855 (1.7); 1.852 (1.7); 1.845 (1.5); 1.836 (1.3); 1.827 (0.8); 1.818 (0.7); 1.810 (0.6); 1.802 (0.5); 1.636 (0.7); 1.628 (0.7); 1.624 (0.7); 1.606 (0.6); 1.292 (0.3); 1.284 (0.4); 1.274 (0.5); 1.256 (1.2); 1.231 (0.4); 0.886 (1.8); 0.882 (1.3); 0.869 (7.6); 0.855 (6.8); 0.852 (6.5); 0.848 (3.9); 0.839 (2.1); 0.815 (0.4); 0.797 (0.3); 0.645 (2.0); 0.632 (5.9); 0.627 (6.2); 0.623 (6.2); 0.606 (1.7); 0.008 (0.8); 0.000 (30.3)

Example 1.2: $^1$H-NMR (400.1 MHz, CDCl$_3$): δ=10.681 (0.9); 10.661 (1.0); 7.518 (0.8); 7.360 (0.4); 7.310 (2.1); 7.260 (108.6); 7.211 (1.5); 7.160 (0.3); 7.089 (1.7); 7.070 (3.6); 7.036 (2.6); 7.016 (1.3); 7.000 (3.6); 6.559 (1.1); 5.158 (1.1); 5.138 (2.1); 5.117 (1.1); 3.165 (1.3); 3.146 (1.4); 3.127 (1.5); 3.108 (1.5); 2.978 (0.4); 2.968 (0.9); 2.958 (1.3); 2.950 (1.8); 2.940 (1.9); 2.931 (1.3); 2.922 (1.0); 2.912 (0.5); 2.701 (0.6); 2.688 (0.6); 2.664 (0.9); 2.646 (1.1); 2.627 (0.9); 2.607 (0.6); 2.550 (1.3); 2.528 (0.9); 2.512 (1.2); 2.490 (0.9); 2.352 (0.4); 2.302 (16.0); 1.273 (12.3); 1.266 (1.3); 1.256 (12.1); 1.232 (0.3); 1.009 (0.5); 1.004 (0.6); 0.998 (1.1); 0.991 (3.4); 0.986 (1.8); 0.980 (1.8); 0.975 (2.9); 0.973 (3.1); 0.967 (1.4); 0.963 (1.0); 0.958 (0.9); 0.783 (1.1); 0.780 (1.2); 0.773 (3.0); 0.771 (3.0); 0.763 (3.0); 0.757 (2.0); 0.748 (1.0); 0.737 (0.3); 0.050 (0.7); 0.008 (0.9)

Example 1.3: $^1$H-NMR (400.0 MHz, CDCl$_3$): δ=7.518 (0.6); 7.259 (102.6); 7.086 (1.5); 7.066 (3.1); 7.031 (4.3); 7.015 (1.7); 6.995 (0.6); 5.324 (1.5); 5.297 (5.0); 3.064 (1.1); 3.045 (1.3); 3.026 (1.4); 3.006 (1.4); 2.537 (0.9); 2.515 (1.1); 2.499 (0.8); 2.477 (1.0); 2.301 (16.0); 2.284 (0.8); 2.264 (0.9); 2.245 (0.7); 1.284 (0.5); 1.270 (12.6); 1.253 (12.4); 0.008 (1.3); 0.000 (43.8); −0.009 (1.3)

Example 1.4: $^1$H-NMR (400.1 MHz, CDCl$_3$): δ=7.520 (2.0); 7.361 (0.5); 7.334 (5.7); 7.315 (7.1); 7.261 (358.3); 7.213 (1.6); 7.205 (2.1); 7.191 (7.1); 7.187 (7.3); 7.174 (16.0); 7.169 (16.0); 7.155 (7.5); 7.151 (7.7); 7.137 (3.0); 7.122 (9.3); 7.103 (5.7); 7.075 (0.5); 7.051 (0.4); 6.997 (2.1); 5.935 (0.3); 5.901 (0.5); 5.869 (0.5); 5.852 (0.5); 5.828 (0.4); 5.557 (0.3); 5.552 (0.3); 5.472 (0.4); 5.419 (0.9); 5.279 (6.4); 5.213 (2.3); 5.062 (0.5); 2.886 (1.1); 2.870 (1.9); 2.843 (3.3); 2.827 (6.1); 2.808 (4.5); 2.792 (6.4); 2.775 (4.1); 2.749 (1.9); 2.734 (1.2); 2.123 (1.6); 2.090 (3.9); 2.079 (3.2); 2.064 (2.7); 2.045 (1.2); 1.893 (6.7); 1.878 (9.2); 1.862 (8.1); 1.845 (4.0); 1.733 (0.4); 1.720 (0.4); 1.712 (0.4); 1.582 (54.0); 1.407 (0.4); 1.321 (0.9); 1.304 (1.7); 1.265 (7.6); 1.229 (0.7); 0.899 (3.6); 0.882 (9.5); 0.864 (4.2); 0.146 (0.6); 0.050 (0.4); 0.000 (119.4)

Example 1.5: $^1$H-NMR (400.1 MHz, CDCl$_3$): δ=7.386 (0.4); 7.370 (0.4); 7.365 (0.4); 7.262 (6.1); 7.260 (6.5); 7.171 (0.4); 7.167 (0.4); 7.154 (0.9); 7.140 (0.4); 7.136 (0.5); 7.111 (0.5); 7.106 (0.5); 5.298 (1.6); 5.297 (1.7); 5.166 (0.5); 3.001 (0.7); 2.820 (0.4); 2.802 (0.3); 2.784 (0.4); 2.716 (1.0); 2.043 (0.3); 1.898 (0.3); 1.447 (16.0); 1.433 (0.4); 1.407 (0.3); 1.228 (3.5); 0.002 (2.1); 0.000 (2.3)

Example 1.6: $^1$H-NMR (400.1 MHz, CDCl$_3$): δ=7.259 (9.2); 7.081 (0.4); 7.071 (0.6); 7.063 (0.7); 7.014 (0.4); 5.297 (4.7); 3.000 (0.5); 2.715 (0.6); 2.714 (0.7); 2.292 (2.7); 2.043 (0.5); 1.468 (0.5); 1.455 (0.7); 1.436 (0.4); 1.419 (0.8); 1.284 (2.2); 1.273 (4.0); 1.267 (2.4); 1.258 (0.5)

Example 1.7: $^1$H-NMR (400.1 MHz, CDCl$_3$): δ=7.352 (0.3); 7.265 (0.4); 7.259 (18.3); 7.255 (0.7); 7.254 (0.6); 7.253 (0.6); 7.252 (0.6); 7.251 (0.7); 7.250 (0.8); 7.246 (0.8); 7.234 (0.5); 7.231 (0.4); 7.217 (0.5); 5.085 (0.3); 1.451 (16.0); 1.287 (3.3)

Example 1.8: $^1$H-NMR (400.0 MHz, CDCl$_3$): δ=7.293 (55.9); 7.287 (0.4); 7.204 (0.5); 7.202 (0.5); 7.199 (0.5); 7.187 (0.3); 7.185 (0.4); 7.183 (0.5); 7.181 (0.4); 6.904 (0.3); 6.888 (0.3); 6.885 (0.6); 6.873 (0.6); 6.871 (0.5); 6.852 (0.5); 6.849 (0.4); 4.312 (0.3); 2.261 (0.5); 2.247 (0.5); 1.458 (16.0); 0.041 (0.5); 0.037 (0.4); 0.033 (14.9); 0.025 (0.4)

Example 1.14: $^1$H-NMR (399.8 MHz, CDCl$_3$): δ=12.248 (0.5); 9.846 (0.4); 8.814 (1.2); 7.519 (2.1); 7.371 (0.7); 7.329 (9.6); 7.310 (10.3); 7.260 (374.7); 7.215 (4.7); 7.212 (4.8); 7.194 (9.9); 7.177 (6.1); 7.173 (5.7); 6.996 (2.2); 6.925 (7.2); 6.907 (12.5); 6.888 (5.7); 6.862 (12.1); 6.841 (10.6); 5.612 (5.8); 5.233 (5.9); 5.159 (0.7); 4.323 (2.0); 4.309 (3.1); 4.295 (6.5); 4.283 (9.2); 4.271 (11.5); 4.260 (6.4); 4.249 (6.7); 4.240 (8.2); 4.233 (2.5); 4.220 (2.5); 4.212 (2.5); 4.111 (0.5); 3.702 (0.5); 3.563 (0.6); 3.535 (0.7); 3.508 (0.7); 2.830 (0.5); 2.803 (3.6); 2.795 (4.8); 2.786 (4.8); 2.777 (3.6); 2.769 (2.4); 2.759 (1.1); 2.597 (1.9); 2.314 (1.3); 2.292 (3.4); 2.280 (5.0); 2.271 (7.7); 2.258 (10.3); 2.249 (8.4); 2.236 (3.8); 2.224 (1.8); 2.212 (1.4); 2.177 (0.7); 2.071 (0.5); 2.055 (0.5); 2.044 (0.8); 1.607 (0.7); 1.537 (141.6); 1.478 (6.3); 1.415 (0.8); 1.333 (1.6); 1.319 (0.8); 1.294 (1.1); 1.284 (2.4); 1.256 (9.2); 1.214 (0.6); 0.901 (3.6); 0.888 (16.0); 0.873 (15.7); 0.855 (3.4); 0.830 (0.9); 0.687 (0.6); 0.652 (5.1); 0.640 (13.9); 0.634 (14.5); 0.625 (11.6); 0.615 (3.8); 0.146 (1.7); 0.068 (0.7); 0.000 (374.6); −0.065 (0.6); −0.149 (2.0)

Example 1.16: $^1$H-NMR (400.0 MHz, CDCl$_3$): δ=7.519 (0.9); 7.329 (2.6); 7.325 (2.8); 7.311 (3.3); 7.306 (3.0); 7.260 (166.3); 7.216 (1.6); 7.212 (1.4); 7.198 (2.4); 7.195 (2.8); 7.177 (2.1); 7.173 (1.9); 6.996 (0.9); 6.927 (2.5); 6.924 (2.7); 6.908 (3.6); 6.905 (3.9); 6.890 (2.0); 6.887 (2.1); 6.863 (4.4); 6.861 (4.0); 6.843 (3.9); 6.840 (3.5); 5.634 (1.4); 5.299 (16.0); 5.232 (1.1); 4.323 (0.6); 4.309 (0.9); 4.294 (1.9); 4.283 (2.7); 4.271 (3.8); 4.261 (2.1); 4.250 (2.1); 4.241 (2.5); 4.234 (0.9); 4.221 (0.8); 4.213 (0.8); 4.091 (1.0); 2.804 (1.0); 2.796 (1.4); 2.787 (1.3); 2.778 (1.0); 2.288 (0.7); 2.277 (1.4); 2.267 (2.2); 2.255 (2.8); 2.245 (2.3); 2.233 (1.3); 2.220 (0.6); 2.053 (0.5); 2.044 (0.6); 1.333 (0.7); 1.284 (1.0); 1.258 (1.5); 0.985 (0.8); 0.970 (0.7); 0.967 (0.6); 0.910 (0.8); 0.903 (1.2); 0.891 (4.6); 0.876 (4.6); 0.873 (4.4); 0.864 (1.3); 0.858 (1.2); 0.717 (0.6); 0.713 (0.8); 0.710 (0.7); 0.707 (0.7); 0.703 (0.8); 0.700 (0.7); 0.656 (1.6); 0.643 (3.7); 0.638 (3.9); 0.634 (3.7); 0.628 (3.2); 0.618 (1.2); 0.008 (1.8); 0.000 (56.6); −0.009 (1.9)

Example 1.17: $^1$H-NMR (400.0 MHz, CDCl$_3$): δ=7.295 (0.6); 7.292 (0.7); 7.276 (1.0); 7.275 (1.0); 7.274 (1.0); 7.273 (1.2); 7.272 (1.2); 7.271 (1.2); 7.270 (1.2); 7.2694 (1.2); 7.2686 (1.3); 7.264 (50.2); 7.186 (0.7); 7.168 (0.5); 6.916 (0.6); 6.913 (0.7); 6.897 (0.9); 6.894 (1.0); 6.876 (0.5); 6.855 (1.1); 6.852 (0.9); 6.834 (0.9); 6.832 (0.8); 5.301 (5.2); 4.268 (0.6); 4.261 (0.7); 4.253 (0.7); 4.240 (0.5); 4.232 (0.6); 3.754 (9.5); 3.386 (16.0); 3.268 (8.3); 3.238 (4.3); 3.203 (9.8); 3.160 (2.3); 2.219 (0.6); 0.008 (0.6); 0.000 (18.8); −0.009 (0.6)

Example 1.18: $^1$H-NMR (400.0 MHz, CDCl$_3$): δ=7.275 (1.0); 7.261 (80.3); 6.897 (1.1); 6.889 (1.2); 6.875 (1.2); 6.867 (1.2); 6.801 (1.2); 6.794 (1.0); 6.780 (1.2); 6.772 (0.9); 5.646 (0.8); 5.300 (8.4); 5.221 (0.6); 4.302 (1.0); 4.294 (1.0); 4.287 (1.1); 4.278 (0.9); 4.261 (1.1); 4.254 (1.4); 4.239 (1.2); 4.232 (1.5); 4.225 (0.6); 4.211 (0.7); 4.203 (0.6); 2.806 (0.6); 2.796 (0.8); 2.788 (0.8); 2.779 (0.6); 2.260 (0.6); 2.247 (0.6); 2.236 (0.5); 2.217 (0.6); 2.209 (0.7); 2.202 (0.9); 2.195 (1.3); 2.182 (16.0); 2.136 (0.8); 2.044 (0.8); 1.625 (1.0); 1.259 (0.9); 0.910 (0.5); 0.895 (2.7); 0.881 (2.7); 0.878 (2.5); 0.868 (0.5); 0.863 (0.8); 0.662 (0.9); 0.652 (1.8); 0.649 (2.2); 0.644 (2.2); 0.640 (2.1); 0.635 (1.7); 0.623 (0.6); 0.008 (1.0); 0.000 (27.7); −0.009 (0.7)

Example 1.19: $^1$H-NMR (400.0 MHz, CDCl$_3$): δ=10.842 (0.7); 7.519 (5.9); 7.373 (0.6); 7.322 (0.8); 7.314 (0.7); 7.293 (2.6); 7.260 (1060.1); 7.230 (1.1); 7.210 (2.9); 6.996 (5.9); 6.789 (1.3); 6.768 (1.4); 6.759 (1.5); 6.737 (1.6); 6.614 (0.8); 5.298 (1.2); 5.279 (1.1); 4.405 (0.9); 4.389 (1.3); 4.372 (1.0); 4.361 (0.8); 4.320 (0.8); 4.308 (1.2); 4.293 (1.0); 4.277 (1.0); 3.210 (8.6); 3.197 (8.5); 3.157 (1.8); 3.144 (1.8); 2.687 (4.6); 2.272 (1.8); 2.258 (3.1); 2.244 (3.4); 2.229 (1.8); 2.172 (15.9); 2.007 (16.0); 1.284 (0.7); 1.255 (0.8); 0.146 (1.2); 0.033 (0.7); 0.008 (13.9); 0.000 (371.9); −0.009 (11.8); −0.050 (1.0); −0.150 (1.3)

Example 1.20: $^1$H-NMR (400.0 MHz, CDCl$_3$): δ=7.519 (1.6); 7.309 (3.6); 7.305 (3.8); 7.290 (3.9); 7.286 (4.4); 7.260 (273.2); 7.229 (0.7); 7.213 (2.5); 7.209 (2.6); 7.192 (4.2); 7.174 (3.2); 7.170 (2.8); 6.996 (1.6); 6.922 (3.5); 6.919 (3.9); 6.903 (5.2); 6.900 (5.8); 6.885 (2.9); 6.882 (3.1); 6.861 (6.1); 6.858 (5.5); 6.841 (5.3); 6.838 (4.8); 5.571 (1.3); 5.299 (14.8); 5.233 (1.8); 4.321 (0.9); 4.311 (1.2); 4.307 (1.1); 4.293 (3.0); 4.283 (2.9); 4.278 (3.4); 4.267 (4.1); 4.258 (3.9); 4.244 (3.3); 4.236 (3.7); 4.230 (1.3); 4.216 (1.4); 4.208 (1.3); 4.130 (0.5); 4.112 (0.6); 3.180 (12.7); 3.154 (9.2); 3.141 (9.1); 3.033 (16.0); 3.020 (15.6); 2.315 (1.2); 2.307 (1.3); 2.299 (0.8); 2.286 (1.4); 2.276 (1.8); 2.264 (3.2); 2.252 (1.9); 2.243 (1.9); 2.236 (1.9); 2.230 (2.2); 2.223 (2.3); 2.209 (1.5); 2.196 (0.9); 2.187 (0.8); 2.057 (0.6); 2.044 (2.5); 1.606 (1.5); 1.284 (0.6); 1.277 (0.9); 1.259 (1.9); 1.241 (0.9); 0.008 (3.4); 0.000 (97.6); −0.008 (2.9)

Example 1.21: $^1$H-NMR (400.0 MHz, CDCl$_3$): δ=7.518 (0.9); 7.259 (153.3); 7.106 (1.6); 7.087 (3.0); 7.046 (2.6); 7.026 (1.6); 7.004 (1.1); 6.995 (1.4); 5.109 (0.6); 4.492 (0.7); 4.474 (2.2); 4.456 (2.3); 4.439 (0.9); 3.106 (1.2); 3.087 (1.2); 3.067 (1.4); 3.048 (1.4); 2.565 (0.8); 2.543 (1.0); 2.527 (0.7); 2.504 (0.9); 2.342 (0.9); 2.323 (0.6); 2.299 (16.0); 1.467 (9.4); 1.49 (20.0); 1.431 (9.2); 1.278 (5.8); 1.262 (6.9); 0.899 (1.1); 0.882 (4.3); 0.864 (1.5); 0.008 (1.7); 0.000 (63.3); −0.009 (1.9)

Example 1.22: $^1$H-NMR (400.0 MHz, CDCl$_3$): δ=7.518 (4.0); 7.292 (4.3); 7.281 (3.7); 7.259 (719.4); 7.251 (2.6); 7.225 (2.2); 7.221 (3.0); 7.207 (9.6); 7.203 (9.7); 7.189 (14.1); 7.185 (16.8); 7.180 (11.7); 7.167 (8.0); 7.162 (9.9); 7.148 (3.4); 7.137 (10.9); 7.133 (10.3); 7.118 (6.7); 6.995 (3.9); 5.981 (1.4); 5.577 (0.7); 5.271 (3.4); 5.152 (2.9); 2.888 (2.3); 2.862 (3.6); 2.846 (6.5); 2.831 (3.7); 2.822 (4.3); 2.806 (7.1); 2.790 (4.2); 2.765 (2.3); 2.748 (1.4); 2.625 (10.0); 2.091 (2.0); 1.895 (6.7); 1.878 (6.5); 1.590 (9.5); 1.265 (7.8); 0.899 (4.3); 0.882 (16.0); 0.864 (5.8); 0.146 (0.8); 0.008 (7.9); 0.000 (270.1); −0.009 (7.5); −0.150 (0.8)

Example 1.23: $^1$H-NMR (400.6 MHz, CDCl$_3$): δ=7.107 (6.9); 6.888 (3.3); 6.869 (1.1); 6.860 (1.4); 6.850 (1.7); 5.142 (1.0); 2.876 (0.6); 2.858 (0.7); 2.839 (0.7); 2.457 (1.8); 2.387 (0.7); 2.364 (0.8); 2.349 (0.8); 2.326 (0.8); 2.169 (2.6); 2.154 (16.0); 1.160 (1.6); 1.143 (1.7); 1.132 (0.9); 1.114 (13.3); 1.098 (13.0)

Example 1.24: $^1$H-NMR (400.6 MHz, CDCl$_3$): δ=7.315 (5.8); 7.299 (7.3); 7.259 (51.8); 7.247 (23.0); 7.231 (13.1); 7.223 (7.8); 7.213 (8.2); 7.205 (5.2); 7.192 (2.8);

6.148 (1.7); 5.847 (0.7); 5.464 (2.0); 5.318 (7.7); 5.297 (5.3); 5.176 (0.7); 3.044 (3.0); 3.035 (3.5); 3.023 (3.5); 3.013 (3.9); 3.005 (6.2); 2.995 (6.6); 2.983 (6.5); 2.974 (6.4); 2.928 (3.4); 2.908 (6.9); 2.888 (5.4); 2.868 (3.6); 2.848 (2.1); 2.634 (2.2); 2.612 (4.9); 2.594 (1.5); 2.044 (1.5); 1.893 (2.8); 1.645 (16.0); 1.283 (0.7); 1.276 (0.7); 1.258 (1.8); 1.240 (0.5); 0.882 (0.7); 0.008 (5.1); 0.000 (121.0); −0.008 (3.6); −0.022 (0.6)

Example 1.25: $^1$H-NMR (400.0 MHz, CDCl$_3$): δ=7.258 (59.3); 7.111 (1.1); 7.092 (2.4); 7.065 (2.5); 7.063 (2.7); 7.062 (2.6); 7.044 (1.2); 7.043 (1.3); 6.994 (0.6); 6.982 (2.0); 6.176 (0.5); 5.395 (1.5); 5.104 (0.6); 5.083 (1.1); 5.061 (0.6); 3.109 (1.2); 3.089 (1.2); 3.070 (1.4); 3.051 (1.4); 2.568 (0.7); 2.545 (0.8); 2.530 (0.6); 2.508 (0.7); 2.368 (0.6); 2.350 (0.7); 2.331 (0.7); 2.310 (16.0); 1.577 (0.6); 1.271 (6.4); 1.254 (5.4); 0.008 (0.8); 0.000 (24.7); −0.009 (0.7)

Example 1.26: $^1$H-NMR (400.0 MHz, CDCl$_3$): δ=7.518 (1.1); 7.259 (204.8); 7.118 (1.7); 7.098 (3.2); 7.057 (2.9); 7.038 (1.6); 7.013 (1.2); 6.995 (1.2); 5.136 (0.7); 3.114 (1.2); 3.095 (1.2); 3.075 (1.4); 3.057 (1.4); 2.728 (7.5); 2.574 (0.6); 2.554 (0.7); 2.537 (0.6); 2.514 (0.6); 2.347 (0.7); 2.307 (16.0); 1.547 (1.6); 1.427 (0.6); 1.284 (3.0); 1.268 (2.7); 0.882 (0.5); 0.008 (2.6); 0.000 (84.5); −0.009 (2.3)

Example 1.27: $^1$H-NMR (400.0 MHz, d$_6$-DMSO): δ=8.520 (1.9); 8.502 (2.0); 8.063 (1.7); 7.905 (1.9); 7.755 (0.7); 7.271 (5.9); 7.255 (16.0); 7.235 (9.8); 7.216 (10.8); 7.213 (8.6); 7.198 (5.6); 7.195 (4.3); 7.178 (7.1); 7.175 (7.1); 7.160 (8.0); 7.141 (2.7); 5.462 (1.8); 5.444 (1.8); 3.342 (1.6); 3.029 (1.8); 3.022 (2.1); 3.008 (2.1); 3.000 (2.4); 2.990 (3.0); 2.982 (3.2); 2.969 (3.0); 2.961 (2.9); 2.856 (1.8); 2.836 (3.7); 2.816 (3.1); 2.796 (2.5); 2.776 (1.4); 2.675 (1.0); 2.670 (1.4); 2.666 (1.1); 2.524 (3.8); 2.519 (5.4); 2.510 (71.3); 2.506 (157.7); 2.501 (222.6); 2.497 (158.6); 2.492 (74.2); 2.456 (3.1); 2.451 (3.0); 2.333 (1.0); 2.328 (1.4); 2.323 (1.0); 2.319 (0.5); 2.042 (2.0); 2.020 (5.6); 2.010 (2.3); 1.999 (5.5); 1.989 (5.0); 1.978 (2.3); 1.968 (4.9); 1.946 (1.7); 0.008 (1.7); 0.006 (0.6); 0.000 (60.8); −0.007 (0.9); −0.009 (2.0)

Example 1.28: $^1$H-NMR (400.0 MHz, d$_6$-DMSO): δ=8.410 (1.9); 8.391 (1.9); 7.933 (1.7); 7.906 (2.2); 7.903 (3.8); 7.898 (2.7); 7.894 (2.4); 7.890 (1.8); 7.887 (2.0); 7.820 (1.6); 7.721 (3.9); 7.718 (1.1); 7.699 (1.2); 7.696 (1.3); 7.661 (1.0); 7.568 (1.6); 7.548 (2.8); 7.528 (1.4); 7.177 (4.2); 7.171 (4.8); 7.159 (9.3); 7.141 (11.0); 7.136 (11.4); 7.130 (10.8); 7.113 (16.0); 7.094 (5.5); 5.523 (0.6); 5.153 (1.9); 3.316 (7.2); 2.809 (1.0); 2.787 (2.7); 2.767 (3.8); 2.756 (4.5); 2.742 (4.5); 2.701 (1.4); 2.675 (1.7); 2.670 (2.2); 2.665 (1.7); 2.563 (0.7); 2.554 (0.6); 2.523 (6.1); 2.519 (8.6); 2.510 (117.4); 2.506 (257.1); 2.501 (359.2); 2.496 (250.6); 2.492 (112.6); 2.332 (1.4); 2.328 (2.0); 2.323 (1.6); 1.990 (4.7); 1.977 (4.8); 1.964 (5.1); 1.832 (2.5); 1.813 (2.6); 1.789 (1.5); 1.743 (2.1); 1.235 (1.8); 0.008 (2.4); 0.000 (90.6); −0.009 (2.5)

Example 1.29: $^1$H-NMR (400.0 MHz, CDCl$_3$): δ=8.466 (1.0); 7.518 (1.8); 7.326 (2.3); 7.310 (2.4); 7.292 (2.0); 7.291 (1.6); 7.282 (11.8); 7.279 (13.7); 7.274 (9.9); 7.273 (9.4); 7.272 (9.9); 7.2684 (12.6); 7.2677 (12.6); 7.266 (11.0); 7.265 (11.3); 7.2644 (11.9); 7.2637 (10.1); 7.263 (10.2); 7.259 (339.4); 7.2554 (9.1); 7.2545 (7.1); 7.254 (6.1); 7.253 (5.5); 7.252 (5.4); 7.2512 (5.7); 7.2505 (5.8); 7.250 (5.8); 7.248 (4.6); 7.247 (4.8); 7.246 (4.4); 7.242 (5.3); 7.234 (3.1); 7.228 (3.9); 7.226 (4.0); 7.210 (2.5); 7.202 (1.3); 6.995 (1.9); 6.093 (1.9); 5.509 (1.2); 5.434 (1.1); 5.340 (0.7); 4.301 (0.5); 4.130 (0.5); 3.312 (7.6); 3.083 (1.5); 3.074 (1.6); 3.061 (1.7); 3.052 (1.8); 3.043 (2.9); 3.034 (3.1); 3.022 (3.1); 3.012 (3.0); 3.006 (2.4); 2.957 (1.7); 2.937 (3.4); 2.918 (2.6); 2.897 (2.0); 2.877 (1.3); 2.720 (16.0); 2.708 (12.2); 2.655 (1.2); 2.043 (2.4); 1.988 (1.8); 1.967 (3.2); 1.956 (2.0); 1.948 (3.2); 1.935 (3.1); 1.928 (1.8); 1.916 (2.8); 1.895 (1.4); 1.591 (1.0); 1.441 (0.6); 1.424 (1.1); 1.406 (0.6); 1.304 (0.9); 1.276 (2.1); 1.264 (3.8); 1.258 (3.6); 1.240 (1.2); 0.899 (2.1); 0.882 (8.3); 0.864 (2.9); 0.008 (4.7); 0.006 (1.5); 0.0054 (1.6); 0.0046 (2.1); 0.004 (2.8); 0.003 (4.2); 0.002 (6.3); 0.000 (147.9); −0.003 (7.6); −0.0035 (5.2); −0.0044 (3.4); −0.005 (2.5); −0.006 (2.2); −0.007 (2.0); −0.009 (5.0); −0.011 (1.3); −0.012 (1.3); −0.013 (1.0); −0.015 (0.7)

Example 1.30: $^1$H-NMR (400.0 MHz, CDCl$_3$): δ=8.467 (1.2); 7.518 (1.4); 7.283 (2.7); 7.270 (2.2); 7.259 (259.2); 7.228 (1.7); 7.224 (2.0); 7.210 (5.9); 7.206 (5.9); 7.192 (8.5); 7.187 (9.3); 7.182 (6.3); 7.164 (5.8); 7.143 (7.6); 7.124 (4.2); 6.995 (1.5); 6.059 (1.2); 5.661 (0.6); 5.438 (1.2); 5.197 (1.5); 3.312 (6.4); 3.006 (1.6); 2.911 (0.8); 2.896 (1.4); 2.869 (2.1); 2.852 (3.8); 2.839 (2.7); 2.830 (2.9); 2.814 (4.5); 2.798 (2.7); 2.787 (1.2); 2.771 (1.7); 2.715 (16.0); 2.708 (13.8); 2.095 (1.4); 2.043 (1.4); 1.904 (4.6); 1.887 (4.5); 1.579 (1.1); 1.424 (0.8); 1.265 (3.2); 1.240 (0.8); 1.237 (0.8); 1.220 (0.6); 0.899 (1.6); 0.882 (5.7); 0.864 (2.2); 0.008 (3.5); 0.000 (103.6); −0.009 (3.7)

Example 1.31: $^1$H-NMR (400.0 MHz, CDCl$_3$): δ=7.259 (49.9); 7.156 (1.5); 7.137 (2.7); 7.117 (1.2); 7.085 (2.5); 7.066 (1.5); 5.297 (1.8); 5.258 (1.2); 2.976 (0.6); 2.968 (0.9); 2.959 (0.9); 2.946 (0.9); 2.937 (0.9); 2.888 (0.5); 2.868 (1.0); 2.848 (0.8); 2.828 (0.6); 2.333 (16.0); 1.911 (0.8); 1.892 (0.9); 1.880 (0.8); 1.860 (0.7); 1.258 (0.6); 0.008 (0.8); 0.000 (19.9); −0.009 (0.7)

Example 1.32: $^1$H-NMR (400.0 MHz, CDCl$_3$): δ=8.057 (1.0); 8.053 (1.6); 8.048 (1.1); 7.950 (1.0); 7.947 (1.3); 7.944 (1.0); 7.931 (1.2); 7.928 (1.6); 7.925 (1.3); 7.885 (1.3); 7.518 (2.6); 7.475 (0.7); 7.473 (0.7); 7.470 (0.8); 7.467 (0.6); 7.455 (0.9); 7.453 (0.9); 7.450 (1.0); 7.447 (0.9); 7.358 (1.7); 7.338 (2.6); 7.318 (1.8); 7.310 (1.9); 7.292 (2.9); 7.283 (3.1); 7.276 (3.4); 7.274 (3.3); 7.273 (3.4); 7.2723 (3.4); 7.2715 (3.4); 7.271 (3.4); 7.270 (3.5); 7.269 (3.6); 7.2683 (3.8); 7.2675 (3.9); 7.266 (4.7); 7.259 (444.5); 7.252 (2.9); 7.251 (1.5); 7.250 (1.3); 7.249 (1.2); 7.248 (1.1); 7.2473 (1.0); 7.2465 (0.8); 7.246 (0.8); 7.245 (0.7); 7.244 (0.6); 7.2433 (0.6); 7.2425 (0.5); 7.242 (0.5); 7.241 (0.6); 7.239 (0.6); 7.216 (2.3); 7.211 (3.0); 7.197 (7.9); 7.193 (8.0); 7.179 (10.7); 7.174 (9.8); 7.172 (6.6); 7.167 (8.8); 7.153 (6.2); 7.149 (8.2); 7.130 (11.3); 7.111 (5.5); 7.109 (5.4); 6.995 (2.5); 6.082 (1.5); 5.368 (1.4); 5.182 (2.0); 4.481 (3.6); 4.463 (10.3); 4.446 (10.6); 4.428 (4.0); 4.130 (0.8); 4.112 (0.7); 3.425 (0.5); 3.162 (1.1); 3.144 (1.1); 2.991 (16.0); 2.903 (1.0); 2.887 (1.9); 2.872 (1.2); 2.861 (2.8); 2.845 (5.1); 2.830 (2.7); 2.819 (3.4); 2.804 (5.7); 2.788 (3.4); 2.778 (1.3); 2.761 (2.0); 2.745 (1.1); 2.678 (15.8); 2.086 (1.9); 2.043 (4.1); 1.894 (5.3); 1.878 (5.7); 1.861 (3.3); 1.600 (0.6); 1.460 (44.0); 1.442 (95.1); 1.425 (43.9); 1.372 (2.0); 1.363 (3.3); 1.354 (4.8); 1.347 (5.1); 1.336 (3.1); 1.332 (2.9); 1.304 (1.4); 1.281 (2.1); 1.276 (3.1); 1.264 (5.8); 1.258 (5.4); 1.240 (1.6); 0.899 (3.1); 0.882 (11.5); 0.864 (4.3); 0.146 (0.6); 0.008 (5.5); 0.000 (197.3); −0.009 (5.9); −0.150 (0.6)

Example 1.33: $^1$H-NMR (400.0 MHz, CDCl$_3$): δ=7.876 (0.7); 7.518 (1.4); 7.323 (1.7); 7.309 (1.9); 7.295 (0.9); 7.2922 (1.1); 7.2915 (1.1); 7.290 (0.8); 7.289 (0.9); 7.2883 (0.9); 7.2875 (0.9); 7.287 (0.9); 7.286 (0.9); 7.285 (0.9); 7.2843 (0.9); 7.2835 (0.9); 7.283 (0.9); 7.282 (1.1); 7.281 (1.2); 7.280 (1.5); 7.279 (1.6); 7.278 (1.7); 7.277 (1.6); 7.2764 (1.6); 7.2756 (1.6); 7.275 (1.6); 7.274 (1.7); 7.273 (2.0); 7.269 (11.4); 7.266 (13.6); 7.265 (7.8); 7.260

(242.6); 7.256 (16.7); 7.253 (8.5); 7.249 (1.5); 7.248 (1.2); 7.2474 (1.0); 7.2466 (0.9); 7.246 (0.7); 7.245 (0.7); 7.244 (0.6); 7.2434 (0.6); 7.2426 (0.6); 7.242 (0.7); 7.241 (0.7); 7.237 (2.5); 7.235 (1.7); 7.233 (1.7); 7.228 (4.0); 7.226 (2.9); 7.220 (2.3); 7.214 (3.0); 7.209 (3.3); 7.208 (2.7); 7.206 (2.4); 7.195 (2.2); 7.188 (1.3); 6.995 (1.4); 5.984 (0.8); 5.484 (0.9); 5.364 (0.8); 4.484 (3.0); 4.466 (9.0); 4.448 (9.2); 4.431 (3.2); 3.068 (1.3); 3.058 (1.5); 3.046 (1.5); 3.036 (1.6); 3.028 (2.6); 3.018 (2.7); 3.006 (2.7); 2.997 (2.8); 2.991 (15.6); 2.945 (1.6); 2.924 (3.4); 2.904 (2.7); 2.885 (1.9); 2.864 (1.2); 2.678 (16.0); 2.644 (0.9); 1.965 (1.7); 1.947 (2.2); 1.945 (2.9); 1.933 (1.8); 1.926 (3.0); 1.923 (2.3); 1.915 (2.2); 1.912 (2.8); 1.905 (1.9); 1.894 (2.7); 1.873 (1.5); 1.621 (0.7); 1.603 (0.9); 1.586 (0.8); 1.464 (28.5); 1.446 (61.7); 1.428 (28.4); 1.285 (0.7); 1.264 (1.2); 1.237 (1.0); 1.220 (1.4); 1.176 (1.4); 1.160 (1.4); 0.899 (0.6); 0.882 (2.5); 0.864 (0.9); 0.010 (0.6); 0.008 (3.3); 0.0064 (1.2); 0.0055 (1.3); 0.005 (1.5); 0.004 (2.0); 0.000 (104.1); −0.005 (1.9); −0.006 (1.4); −0.007 (1.0); −0.009 (3.0)

Example 1.34: $^1$H-NMR (400.0 MHz, CDCl$_3$): δ=7.518 (0.7); 7.333 (0.7); 7.322 (0.7); 7.317 (0.8); 7.271 (0.5); 7.270 (0.6); 7.269 (0.7); 7.2684 (0.7); 7.2676 (0.7); 7.267 (0.9); 7.266 (1.1); 7.265 (1.3); 7.2644 (1.6); 7.2635 (2.1); 7.259 (115.2); 7.254 (1.1); 7.253 (0.9); 7.252 (0.8); 7.2514 (0.7); 7.2506 (0.5); 7.216 (0.5); 7.202 (1.5); 7.198 (1.6); 7.184 (2.9); 7.178 (2.7); 7.164 (1.3); 7.159 (1.5); 7.145 (0.5); 7.134 (1.8); 7.129 (1.6); 7.115 (1.0); 7.113 (1.0); 6.995 (0.7); 5.298 (5.9); 2.992 (16.0); 2.979 (15.9); 2.861 (0.6); 2.844 (1.0); 2.822 (0.7); 2.806 (1.1); 2.791 (0.7); 1.912 (0.9); 1.896 (1.3); 1.881 (1.2); 1.865 (0.6); 1.557 (0.6); 1.333 (0.6); 1.284 (1.0); 1.256 (1.6); 0.008 (1.6); 0.0063 (0.6); 0.0055 (0.6); 0.005 (0.7); 0.004 (1.0); 0.000 (51.2); −0.003 (2.7); −0.004 (1.1); −0.005 (0.8); −0.006 (0.6); −0.007 (0.5); −0.009 (1.6)

Example 1.35: $^1$H-NMR (400.0 MHz, CDCl$_3$): δ=7.343 (1.1); 7.325 (1.4); 7.280 (0.6); 7.272 (3.6); 7.269 (4.3); 7.260 (51.6); 7.240 (0.9); 7.235 (1.8); 7.227 (0.9); 7.221 (1.0); 7.217 (1.1); 7.212 (0.8); 7.202 (0.7); 5.298 (4.8); 3.055 (0.5); 3.042 (0.6); 3.033 (0.6); 3.024 (1.0); 3.015 (1.1); 3.002 (1.2); 2.991 (16.0); 2.978 (15.5); 2.944 (0.7); 2.924 (1.4); 2.903 (1.1); 2.884 (0.7); 1.935 (1.0); 1.924 (0.5); 1.916 (1.0); 1.903 (0.9); 1.884 (0.9); 1.284 (0.6); 1.256 (0.9); 0.008 (0.7); 0.000 (21.5); −0.009 (0.7)

Example 1.36: $^1$H-NMR (400.0 MHz, d$_6$-DMSO): δ=8.374 (0.9); 8.353 (0.9); 7.904 (0.9); 7.900 (0.8); 7.895 (0.6); 7.888 (0.6); 7.841 (1.0); 7.787 (1.0); 7.698 (0.6); 7.662 (0.6); 7.548 (0.6); 7.096 (2.5); 7.077 (3.5); 7.000 (2.7); 6.981 (1.9); 6.907 (3.0); 5.017 (0.9); 3.330 (2.2); 3.015 (1.4); 2.995 (1.4); 2.970 (0.6); 2.506 (26.9); 2.502 (33.0); 2.498 (24.8); 2.454 (2.4); 2.440 (2.3); 2.232 (16.0); 1.181 (5.9); 1.169 (4.8); 0.000 (0.8)

Example 1.37: $^1$H-NMR (400.0 MHz, CDCl$_3$): δ=7.518 (2.8); 7.294 (3.2); 7.259 (523.1); 7.233 (16.3); 7.230 (14.8); 7.215 (20.4); 7.211 (17.4); 7.197 (23.8); 7.193 (17.0); 7.180 (16.5); 7.161 (15.7); 7.143 (26.4); 7.125 (13.5); 7.123 (12.9); 6.995 (2.8); 6.257 (4.7); 6.238 (4.7); 5.612 (1.9); 5.414 (13.1); 5.298 (9.5); 5.153 (5.5); 5.133 (5.6); 3.083 (0.8); 2.907 (1.9); 2.891 (3.4); 2.864 (5.5); 2.848 (10.0); 2.823 (8.1); 2.808 (12.7); 2.792 (7.1); 2.781 (2.6); 2.766 (4.2); 2.749 (2.4); 2.161 (1.7); 2.112 (2.6); 2.090 (4.4); 2.078 (5.2); 1.893 (14.7); 1.876 (16.0); 1.861 (7.9); 1.842 (3.3); 1.587 (3.8); 1.333 (0.7); 1.284 (1.2); 1.257 (2.1); 0.146 (0.6); 0.008 (6.4); 0.000 (209.1); −0.007 (1.6); −0.009 (5.8); −0.149 (0.5)

Example 1.38: $^1$H-NMR (400.0 MHz, CDCl$_3$): δ=7.518 (4.5); 7.309 (6.9); 7.296 (14.7); 7.283 (66.7); 7.273 (100.6); 7.259 (824.4); 7.243 (23.6); 7.231 (23.4); 7.225 (14.3); 7.214 (12.9); 7.203 (6.1); 6.995 (4.3); 6.261 (6.4); 5.896 (2.6); 5.491 (4.9); 5.471 (11.4); 5.452 (12.5); 5.416 (16.0); 5.337 (6.1); 5.298 (3.6); 3.972 (1.2); 3.083 (4.6); 3.074 (5.3); 3.061 (5.5); 3.052 (6.4); 3.043 (9.5); 3.034 (9.8); 3.021 (9.9); 3.012 (9.7); 2.954 (7.6); 2.933 (15.0); 2.913 (11.7); 2.894 (8.5); 2.873 (4.7); 2.735 (2.1); 2.672 (3.2); 2.653 (5.2); 2.643 (6.3); 2.621 (6.3); 2.004 (7.3); 1.981 (2.7); 1.960 (6.9); 1.940 (8.6); 1.927 (8.6); 1.908 (7.7); 1.887 (3.6); 1.578 (4.7); 1.370 (1.7); 1.333 (1.3); 1.286 (2.9); 1.255 (4.7); 0.880 (1.0); 0.146 (1.1); 0.008 (9.9); 0.000 (321.3); −0.009 (8.9); −0.150 (1.1)

Example 1.39: $^1$H-NMR (400.0 MHz, CDCl$_3$): δ=7.259 (78.5); 7.109 (1.0); 7.090 (1.8); 7.046 (1.8); 7.029 (1.5); 4.224 (0.7); 4.220 (0.6); 4.208 (0.6); 4.204 (0.7); 4.187 (0.5); 3.098 (0.7); 3.079 (0.8); 3.060 (0.8); 3.041 (0.8); 2.544 (0.6); 2.504 (0.5); 2.329 (0.6); 2.305 (9.9); 2.292 (0.6); 2.044 (0.6); 1.553 (0.6); 1.290 (2.8); 1.269 (16.0); 1.258 (3.5); 1.253 (13.3); 0.899 (1.6); 0.882 (6.0); 0.864 (2.2); 0.008 (1.0); 0.000 (32.0); −0.009 (0.9)

Example 1.40: $^1$H-NMR (400.0 MHz, CDCl$_3$): δ=7.260 (52.4); 7.094 (1.8); 7.075 (3.6); 7.048 (2.9); 7.039 (3.4); 7.020 (1.4); 4.130 (0.8); 4.112 (0.8); 3.364 (5.3); 3.139 (6.3); 3.077 (1.2); 3.057 (1.3); 3.038 (1.5); 3.019 (1.5); 2.555 (1.0); 2.532 (1.2); 2.516 (0.8); 2.494 (1.0); 2.305 (16.0); 2.043 (4.0); 1.290 (7.4); 1.273 (7.5); 1.258 (3.2); 1.240 (1.3); 0.899 (0.7); 0.882 (2.6); 0.864 (1.0); 0.008 (0.6); 0.000 (21.6); −0.009 (0.6)

Example 1.41: $^1$H-NMR (400.0 MHz, CDCl$_3$): δ=7.259 (37.2); 7.101 (1.4); 7.082 (2.8); 7.043 (3.5); 7.026 (2.3); 5.287 (0.5); 3.087 (1.1); 3.068 (1.2); 3.048 (1.3); 3.029 (1.4); 2.990 (13.9); 2.977 (13.8); 2.559 (0.8); 2.537 (1.0); 2.521 (0.7); 2.499 (0.8); 2.302 (16.0); 2.283 (0.6); 2.043 (1.8); 1.283 (4.8); 1.276 (3.4); 1.266 (6.3); 1.258 (3.1); 1.240 (0.8); 0.899 (1.3); 0.882 (4.3); 0.864 (1.7); 0.000 (14.2)

Example 1.42: $^1$H-NMR (400.0 MHz, CDCl$_3$): δ=8.084 (0.6); 7.260 (72.0); 7.106 (1.3); 7.086 (2.5); 7.044 (2.2); 7.025 (2.0); 6.995 (0.5); 4.202 (1.9); 4.184 (6.1); 4.166 (6.2); 4.148 (2.1); 3.739 (1.3); 3.723 (3.8); 3.707 (4.0); 3.691 (1.4); 3.095 (0.9); 3.075 (0.9); 3.056 (1.0); 3.036 (1.1); 2.644 (2.3); 2.628 (4.5); 2.612 (2.2); 2.564 (0.6); 2.541 (0.7); 2.525 (0.5); 2.503 (0.6); 2.323 (0.7); 2.303 (12.8); 2.286 (0.6); 2.043 (1.0); 1.562 (0.6); 1.291 (8.3); 1.273 (16.0); 1.255 (7.3); 1.240 (0.5); 0.899 (0.7); 0.882 (2.5); 0.864 (0.9); 0.008 (0.9); 0.000 (29.9); −0.009 (0.9)

Example 1.43: $^1$H-NMR (400.0 MHz, CDCl$_3$): δ=7.259 (35.9); 7.097 (1.1); 7.077 (2.2); 7.039 (2.6); 7.023 (1.8); 4.278 (2.0); 4.260 (6.2); 4.242 (6.3); 4.225 (2.1); 4.196 (6.1); 4.181 (6.1); 3.091 (0.9); 3.072 (0.9); 3.053 (1.0); 3.034 (1.0); 2.562 (0.6); 2.539 (0.7); 2.501 (0.6); 2.305 (12.3); 2.042 (1.2); 1.323 (7.7); 1.306 (16.0); 1.288 (9.9); 1.275 (2.8); 1.268 (3.7); 1.258 (2.1); 1.240 (0.6); 0.899 (0.9); 0.882 (3.3); 0.864 (1.2); 0.000 (14.5)

Example 1.44: $^1$H-NMR (400.0 MHz, CDCl$_3$): δ=7.260 (30.5); 7.099 (1.0); 7.079 (2.2); 7.046 (2.7); 7.030 (2.0); 4.130 (0.9); 4.112 (0.9); 3.083 (0.8); 3.064 (0.9); 3.044 (1.0); 3.025 (1.1); 3.004 (16.0); 2.999 (5.0); 2.554 (0.7); 2.532 (0.8); 2.516 (0.6); 2.493 (0.8); 2.312 (12.9); 2.292 (0.6); 2.043 (4.5); 1.287 (4.3); 1.279 (3.9); 1.276 (2.9); 1.270 (4.5); 1.262 (4.0); 1.258 (3.6); 1.240 (1.4); 0.000 (13.1)

Example 1.45: $^1$H-NMR (400.0 MHz, CDCl$_3$): δ=7.518 (1.0); 7.271 (1.1); 7.269 (1.3); 7.2664 (2.0); 7.2656 (2.3); 7.265 (2.7); 7.259 (176.5); 7.253 (0.8); 7.120 (1.7); 7.101 (3.4); 7.065 (3.0); 7.046 (1.7); 7.003 (1.7); 6.995 (1.6); 6.110 (0.5); 5.098 (0.9); 5.076 (0.5); 4.130 (1.4); 4.113

(1.5); 3.340 (7.2); 3.117 (1.2); 3.098 (1.2); 3.078 (1.4); 3.059 (1.4); 2.574 (0.7); 2.552 (0.8); 2.536 (0.6); 2.515 (0.7); 2.319 (16.0); 2.043 (6.6); 1.551 (0.6); 1.281 (4.5); 1.276 (4.4); 1.265 (4.8); 1.258 (5.4); 1.241 (2.1); 0.899 (0.7); 0.882 (2.7); 0.864 (1.0); 0.008 (2.3); 0.000 (71.4); −0.009 (2.0)

Example 1.46: $^1$H-NMR (400.0 MHz, CDCl$_3$): δ=8.176 (3.1); 7.518 (3.6); 7.259 (655.3); 7.210 (1.4); 6.995 (3.8); 6.886 (5.1); 6.879 (6.7); 6.865 (9.2); 6.858 (12.7); 6.844 (5.1); 6.833 (12.4); 6.827 (8.2); 6.809 (10.8); 6.803 (8.2); 5.886 (1.6); 5.298 (15.7); 5.255 (4.8); 2.871 (2.9); 2.844 (4.5); 2.829 (8.1); 2.813 (4.4); 2.802 (4.7); 2.786 (8.5); 2.769 (5.1); 2.743 (2.9); 2.727 (1.9); 2.487 (16.0); 2.060 (2.8); 1.883 (9.0); 1.548 (18.4); 1.333 (1.2); 1.284 (2.2); 1.256 (4.8); 0.008 (8.1); 0.000 (266.2); −0.009 (8.8)

Example 1.47: $^1$H-NMR (400.0 MHz, CDCl$_3$): δ=7.518 (2.3); 7.259 (432.0); 7.246 (6.2); 7.231 (6.9); 7.227 (6.1); 7.210 (11.4); 7.192 (7.5); 7.189 (6.6); 6.995 (2.4); 6.935 (8.7); 6.932 (10.0); 6.916 (13.9); 6.913 (15.6); 6.897 (7.2); 6.894 (7.8); 6.876 (16.0); 6.873 (14.9); 6.855 (14.1); 6.853 (13.0); 5.929 (0.9); 5.298 (9.1); 5.268 (4.4); 4.325 (2.6); 4.315 (3.3); 4.309 (2.9); 4.296 (6.4); 4.287 (6.4); 4.281 (7.1); 4.272 (5.8); 4.255 (6.4); 4.247 (7.2); 4.232 (6.5); 4.225 (8.3); 4.219 (3.6); 4.204 (3.4); 4.196 (2.9); 2.842 (1.1); 2.625 (5.8); 2.273 (2.4); 2.182 (2.6); 1.566 (3.1); 1.370 (3.6); 1.333 (1.3); 1.286 (5.5); 1.256 (10.0); 0.880 (1.6); 0.008 (5.5); 0.000 (175.3); −0.009 (5.1)

Example 1.48: $^1$H-NMR (400.6 MHz, CDCl$_3$): δ=7.366 (4.1); 7.348 (4.3); 7.288 (4.3); 7.285 (4.2); 7.268 (9.0); 7.266 (8.9); 7.265 (8.7); 7.261 (30.3); 7.249 (4.9); 7.246 (4.5); 7.148 (0.5); 7.127 (0.6); 7.088 (0.6); 6.957 (7.3); 6.955 (7.4); 6.938 (12.8); 6.936 (12.9); 6.920 (6.1); 6.918 (6.0); 6.886 (8.9); 6.866 (7.9); 6.220 (0.5); 5.589 (0.7); 5.352 (5.0); 5.298 (16.0); 4.768 (1.5); 4.420 (2.0); 2.614 (2.3); 2.513 (0.9); 2.445 (0.8); 1.372 (3.7); 1.333 (0.7); 1.286 (5.3); 1.255 (7.8); 0.880 (1.2); 0.863 (0.6); 0.000 (15.2); −0.009 (0.6)

Example 1.49: $^1$H-NMR (400.0 MHz, CDCl$_3$): δ=7.736 (0.5); 7.519 (0.9); 7.260 (182.3); 7.017 (0.6); 7.009 (0.6); 6.996 (1.3); 6.990 (0.8); 6.980 (1.5); 6.968 (1.6); 6.958 (1.3); 6.939 (1.9); 6.932 (1.2); 6.918 (2.6); 6.910 (2.0); 6.898 (2.2); 6.897 (2.3); 6.890 (1.8); 6.825 (4.5); 6.813 (4.5); 6.803 (2.9); 6.791 (2.7); 5.299 (16.0); 4.301 (0.7); 4.291 (0.8); 4.284 (0.7); 4.272 (2.1); 4.263 (2.0); 4.256 (2.3); 4.246 (2.8); 4.237 (1.6); 4.224 (1.4); 4.216 (1.7); 4.196 (0.5); 4.188 (0.5); 2.487 (4.1); 2.485 (4.2); 2.265 (0.7); 2.146 (0.9); 1.286 (0.6); 1.257 (1.0); 0.008 (2.2); 0.000 (69.0); −0.009 (1.9)

Example 1.50: $^1$H-NMR (400.0 MHz, CDCl$_3$): δ=7.258 (72.2); 7.160 (1.7); 7.141 (2.9); 7.126 (1.1); 7.086 (2.5); 7.067 (1.6); 5.297 (3.7); 5.256 (0.9); 3.968 (0.8); 3.958 (0.8); 3.404 (3.4); 2.990 (0.5); 2.980 (0.6); 2.972 (0.9); 2.963 (0.9); 2.951 (0.9); 2.941 (0.9); 2.890 (0.5); 2.870 (1.1); 2.850 (0.9); 2.831 (0.6); 2.333 (16.0); 1.916 (1.1); 1.905 (0.6); 1.897 (1.1); 1.884 (1.0); 1.876 (0.6); 1.865 (1.0); 0.008 (1.0); 0.000 (30.3); −0.008 (1.0)

Example 1.51: $^1$H-NMR (400.6 MHz, MeOD): δ=7.082 (2.0); 7.063 (3.3); 7.014 (2.8); 6.994 (2.0); 6.982 (3.4); 5.178 (0.5); 4.903 (0.6); 4.877 (77.9); 3.340 (5.9); 3.336 (11.4); 3.332 (16.5); 3.328 (11.3); 3.323 (5.6); 3.122 (20.8); 3.093 (1.2); 3.074 (1.3); 3.055 (1.3); 3.036 (1.3); 2.532 (0.8); 2.509 (1.1); 2.494 (0.7); 2.471 (1.0); 2.388 (0.9); 2.369 (1.1); 2.352 (0.8); 2.279 (1.3); 1.380 (1.1); 1.319 (1.8); 1.309 (2.6); 1.280 (8.5); 1.263 (8.2)

Example 1.52: $^1$H-NMR (400.0 MHz, CDCl$_3$): δ=7.258 (58.1); 7.099 (0.8); 7.020 (10.3); 7.017 (9.6); 5.249 (0.8); 2.808 (0.7); 2.792 (1.2); 2.770 (0.8); 2.754 (1.2); 2.737 (0.7); 2.624 (0.5); 2.282 (16.0); 1.867 (1.3); 1.851 (1.2); 1.564 (0.8); 1.258 (0.9); 0.008 (0.8); 0.000 (23.8); −0.009 (0.6)

Example 1.53: $^1$H-NMR (400.6 MHz, MeOD): δ=6.987 (2.0); 6.968 (3.4); 6.917 (2.7); 6.892 (3.6); 4.803 (0.6); 4.780 (59.4); 3.244 (7.3); 3.240 (14.3); 3.235 (21.4); 3.231 (17.3); 3.227 (7.8); 3.218 (2.4); 3.212 (3.2); 3.206 (2.3); 3.192 (3.3); 2.998 (1.2); 2.979 (1.3); 2.960 (1.5); 2.941 (1.4); 2.437 (0.8); 2.414 (1.1); 2.400 (0.7); 2.377 (1.0); 2.312 (0.6); 2.293 (0.8); 2.290 (0.8); 2.272 (1.3); 2.255 (0.9); 2.238 (0.5); 2.185 (16.0); 1.786 (1.8); 1.780 (0.6); 1.773 (1.2); 1.767 (2.8); 1.761 (1.2); 1.754 (1.3); 1.748 (2.9); 1.742 (1.2); 1.736 (0.6); 1.729 (1.8); 1.224 (0.9); 1.214 (1.7); 1.187 (10.9); 1.170 (10.7); 1.008 (0.5); 0.991 (6.6); 0.972 (13.0); 0.953 (5.7)

Example 1.54: $^1$H-NMR (400.6 MHz, MeOD): δ=8.002 (4.1); 7.981 (4.6); 7.963 (0.9); 7.488 (1.8); 7.481 (3.6); 7.466 (2.0); 7.460 (3.3); 7.071 (2.2); 7.052 (3.6); 7.003 (2.8); 6.983 (1.7); 6.960 (3.3); 5.508 (2.9); 4.877 (66.3); 3.340 (6.6); 3.336 (13.0); 3.332 (18.9); 3.328 (12.8); 3.323 (6.3); 3.079 (1.2); 3.060 (1.4); 3.041 (1.4); 3.022 (1.4); 2.519 (0.8); 2.495 (1.1); 2.481 (0.7); 2.458 (1.0); 2.391 (0.6); 2.370 (0.9); 2.351 (1.2); 2.334 (0.9); 2.284 (0.7); 2.265 (16.0); 1.318 (0.9); 1.309 (1.3); 1.263 (9.9); 1.247 (9.6)

Example 1.55: $^1$H-NMR (400.6 MHz, MeOD): δ=8.035 (2.9); 8.018 (2.9); 7.990 (1.0); 7.987 (1.1); 7.983 (0.6); 7.969 (1.5); 7.966 (1.0); 7.661 (0.7); 7.643 (0.7); 7.614 (1.0); 7.599 (0.7); 7.595 (1.3); 7.577 (0.6); 7.515 (1.4); 7.495 (4.1); 7.476 (2.9); 7.461 (0.9); 7.076 (2.1); 7.057 (3.5); 7.006 (2.7); 6.986 (1.7); 6.968 (3.5); 5.510 (1.3); 4.899 (0.8); 4.877 (97.6); 3.351 (0.6); 3.347 (0.8); 3.340 (12.9); 3.336 (25.8); 3.332 (37.5); 3.328 (25.2); 3.323 (12.6); 3.085 (1.2); 3.066 (1.3); 3.047 (1.4); 3.028 (1.4); 2.524 (0.9); 2.501 (1.1); 2.486 (0.7); 2.463 (1.1); 2.394 (0.6); 2.373 (0.9); 2.355 (1.2); 2.338 (0.9); 2.271 (16.0); 1.381 (0.8); 1.320 (1.3); 1.311 (1.8); 1.270 (11.6); 1.253 (11.3)

Example 1.56: $^1$H-NMR (400.6 MHz, MeOD): δ=8.336 (4.2); 8.331 (1.7); 8.318 (2.6); 8.314 (6.7); 8.244 (7.1); 8.239 (2.1); 8.227 (1.7); 8.222 (4.3); 8.215 (0.8); 7.072 (2.0); 7.053 (3.4); 7.006 (2.7); 7.004 (2.7); 6.985 (2.5); 6.958 (3.1); 5.509 (16.0); 4.878 (103.7); 4.857 (0.8); 3.340 (8.7); 3.336 (16.9); 3.332 (24.2); 3.328 (16.7); 3.324 (8.2); 3.081 (1.1); 3.062 (1.3); 3.055 (0.6); 3.043 (1.4); 3.024 (1.4); 2.520 (0.8); 2.497 (1.1); 2.483 (0.7); 2.459 (0.9); 2.395 (0.7); 2.373 (1.0); 2.355 (1.4); 2.338 (1.0); 2.315 (0.6); 2.277 (4.8); 2.265 (14.9); 1.380 (0.8); 1.361 (0.5); 1.327 (0.9); 1.318 (1.5); 1.308 (2.7); 1.282 (3.0); 1.264 (10.3); 1.247 (8.7)

Example 1.57: $^1$H-NMR (400.6 MHz, MeOD): δ=7.088 (1.9); 7.070 (3.1); 7.017 (2.5); 6.996 (3.7); 5.510 (4.5); 4.904 (1.7); 4.878 (144.6); 3.340 (10.9); 3.336 (21.4); 3.332 (31.7); 3.328 (21.9); 3.323 (10.9); 3.102 (1.1); 3.084 (1.2); 3.065 (1.3); 3.047 (4.8); 2.538 (0.8); 2.515 (1.1); 2.500 (0.7); 2.477 (1.0); 2.422 (0.6); 2.401 (0.9); 2.383 (1.2); 2.370 (0.9); 2.366 (1.0); 2.286 (16.0); 1.906 (0.7); 1.848 (0.6); 1.400 (0.6); 1.380 (1.2); 1.361 (0.6); 1.329 (1.5); 1.320 (2.5); 1.310 (5.3); 1.286 (10.6); 1.269 (10.6); 1.200 (0.5); 1.034 (0.8); 1.016 (0.6); 0.922 (1.0); 0.904 (0.5)

Example 1.58: $^1$H-NMR (400.0 MHz, CDCl$_3$): δ=7.258 (53.4); 7.122 (3.0); 7.111 (2.9); 7.061 (2.3); 7.041 (1.3); 5.323 (1.8); 4.130 (0.6); 4.112 (0.6); 2.930 (0.8); 2.921 (0.9); 2.908 (0.8); 2.900 (0.9); 2.859 (0.6); 2.839 (1.3); 2.819 (1.0); 2.800 (0.6); 2.652 (0.6); 2.642 (0.5); 2.631

(0.6); 2.323 (16.0); 2.043 (2.7); 1.856 (1.1); 1.845 (0.5); 1.837 (1.0); 1.824 (1.0); 1.805 (0.9); 1.586 (0.7); 1.276 (1.4); 1.265 (1.6); 1.258 (2.5); 1.240 (0.9); 0.899 (0.9); 0.882 (3.3); 0.864 (1.2); 0.008 (0.7); 0.000 (22.7); −0.009 (0.7)

Example 1.59: $^1$H-NMR (400.0 MHz, CDCl$_3$): δ=7.518 (2.0); 7.332 (4.5); 7.315 (6.2); 7.291 (0.6); 7.289 (0.7); 7.283 (0.8); 7.259 (368.1); 7.254 (17.7); 7.247 (11.0); 7.244 (17.6); 7.241 (10.6); 7.235 (1.7); 7.233 (2.1); 7.224 (6.4); 7.223 (4.8); 7.212 (4.5); 7.208 (2.9); 7.206 (3.9); 7.204 (2.7); 7.202 (2.2); 7.197 (1.7); 7.193 (3.3); 7.184 (1.5); 6.995 (1.9); 5.533 (1.3); 5.292 (4.2); 4.148 (1.1); 4.130 (3.3); 4.112 (3.4); 4.095 (1.2); 3.038 (1.6); 3.029 (1.9); 3.016 (1.8); 3.007 (2.0); 2.998 (3.2); 2.989 (3.4); 2.977 (3.3); 2.967 (3.3); 2.921 (2.5); 2.900 (5.2); 2.880 (4.0); 2.861 (2.7); 2.840 (1.7); 2.681 (1.4); 2.671 (1.7); 2.651 (1.7); 2.641 (1.4); 2.043 (16.0); 1.913 (2.1); 1.895 (2.5); 1.892 (4.1); 1.881 (2.3); 1.874 (4.0); 1.871 (2.6); 1.863 (2.6); 1.860 (3.8); 1.852 (2.2); 1.842 (3.7); 1.839 (2.3); 1.820 (1.8); 1.575 (1.2); 1.304 (0.6); 1.276 (6.1); 1.265 (3.0); 1.258 (11.6); 1.240 (5.1); 0.899 (1.6); 0.882 (6.2); 0.864 (2.3); 0.008 (4.6); 0.006 (1.5); 0.0054 (1.7); 0.0046 (1.9); 0.000 (157.2); −0.006 (1.8); −0.007 (1.6); −0.009 (4.6); −0.011 (0.6)

Example 1.60: $^1$H-NMR (400.0 MHz, d$_6$-DMSO): δ=13.312 (0.7); 8.719 (2.2); 8.697 (2.1); 8.076 (0.7); 7.946 (0.6); 7.905 (3.4); 7.902 (6.3); 7.897 (4.5); 7.892 (3.9); 7.888 (2.9); 7.885 (3.2); 7.882 (1.7); 7.715 (1.9); 7.710 (1.8); 7.698 (2.2); 7.695 (2.2); 7.693 (2.1); 7.690 (2.1); 7.621 (0.9); 7.566 (3.5); 7.546 (5.5); 7.525 (2.4); 7.169 (12.3); 7.150 (16.0); 7.133 (5.0); 7.129 (3.2); 6.871 (5.0); 6.868 (5.5); 6.852 (7.5); 6.849 (8.9); 6.833 (4.2); 6.831 (4.2); 6.791 (9.5); 6.788 (9.4); 6.782 (1.8); 6.769 (8.9); 6.766 (7.3); 5.542 (0.6); 5.150 (1.8); 4.403 (0.6); 4.385 (0.8); 4.301 (2.4); 4.280 (2.3); 4.192 (2.3); 3.305 (109.6); 3.275 (0.5); 3.059 (1.2); 2.998 (0.6); 2.892 (0.7); 2.674 (2.2); 2.669 (3.2); 2.665 (2.4); 2.591 (0.9); 2.523 (10.2); 2.518 (14.6); 2.509 (177.1); 2.505 (379.9); 2.500 (526.5); 2.496 (365.4); 2.491 (164.4); 2.450 (1.2); 2.385 (0.8); 2.381 (1.0); 2.376 (0.7); 2.336 (1.1); 2.332 (2.1); 2.327 (3.2); 2.322 (2.2); 2.095 (2.2); 2.072 (2.5); 2.047 (2.4); 1.988 (1.5); 1.908 (0.5); 1.352 (0.8); 1.334 (1.8); 1.316 (0.8); 1.281 (0.6); 1.259 (0.8); 1.236 (2.1); 1.175 (0.7); 1.157 (0.6); 0.000 (121.1); −0.009 (3.6)

Example 1.61: $^1$H-NMR (400.0 MHz, d$_6$-DMSO): δ=8.614 (0.9); 8.593 (0.9); 7.139 (2.3); 7.119 (3.3); 7.027 (3.6); 7.011 (3.0); 5.398 (0.8); 5.377 (0.8); 4.038 (0.8); 4.021 (0.8); 3.306 (29.7); 2.911 (0.7); 2.896 (0.7); 2.761 (0.8); 2.741 (0.7); 2.721 (0.5); 2.674 (0.6); 2.669 (0.8); 2.665 (0.6); 2.526 (4.6); 2.523 (2.6); 2.518 (3.3); 2.509 (42.9); 2.505 (92.7); 2.500 (129.0); 2.496 (90.7); 2.491 (41.7); 2.468 (0.6); 2.455 (0.6); 2.450 (0.8); 2.445 (0.8); 2.417 (0.7); 2.407 (0.7); 2.395 (0.6); 2.332 (0.6); 2.327 (0.8); 2.322 (0.6); 2.249 (16.0); 1.988 (3.6); 1.980 (1.3); 1.970 (0.5); 1.958 (1.2); 1.949 (1.2); 1.927 (1.0); 1.192 (1.0); 1.175 (2.0); 1.157 (1.0); 0.008 (0.8); 0.000 (28.0); −0.009 (0.9)

Example 1.62: $^1$H-NMR (400.6 MHz, d$_6$-DMSO): δ=8.867 (1.2); 8.850 (1.2); 7.899 (4.9); 7.897 (3.5); 7.895 (3.5); 7.894 (3.9); 7.890 (2.7); 7.883 (2.1); 7.880 (2.5); 7.877 (1.4); 7.694 (1.6); 7.691 (1.7); 7.689 (1.6); 7.686 (1.5); 7.674 (1.9); 7.671 (1.9); 7.669 (1.9); 7.666 (1.7); 7.550 (2.5); 7.546 (0.6); 7.535 (0.7); 7.530 (4.0); 7.510 (1.8); 7.402 (1.5); 7.385 (1.8); 7.369 (1.0); 7.351 (0.7); 7.238 (2.4); 7.235 (2.4); 7.219 (3.7); 7.217 (4.7); 7.216 (4.7); 7.199 (2.9); 7.197 (2.8); 6.898 (3.7); 6.896 (4.3); 6.879 (6.8); 6.877 (7.8); 6.859 (10.1); 6.839 (6.0); 5.632 (1.0); 4.739 (1.3); 4.716 (1.7); 4.693 (0.8); 4.406 (1.9); 4.393 (2.1); 4.382 (1.9); 4.369 (1.7); 3.325 (0.7); 3.000 (16.0); 2.891 (0.5); 2.593 (16.2); 2.526 (1.8); 2.521 (2.3); 2.512 (17.7); 2.508 (35.8); 2.503 (48.5); 2.499 (34.2); 2.494 (15.5); 2.087 (4.1); 1.990 (1.8); 1.259 (0.6); 1.234 (1.4); 1.193 (0.6); 1.183 (0.6); 1.175 (1.1); 1.167 (0.6); 1.158 (0.6); 0.986 (0.9); 0.978 (1.4); 0.970 (0.9); 0.962 (1.5); 0.000 (1.3)

Example 1.63: $^1$H-NMR (400.0 MHz, d$_6$-DMSO): δ=8.614 (5.1); 8.591 (5.1); 7.994 (1.5); 7.975 (1.6); 7.735 (1.3); 7.588 (1.6); 7.204 (4.3); 7.188 (6.0); 7.181 (6.0); 7.166 (3.9); 6.967 (6.8); 6.958 (9.6); 6.952 (15.4); 6.928 (16.0); 5.464 (1.1); 5.069 (3.3); 4.038 (0.9); 4.020 (0.8); 3.307 (174.7); 3.276 (0.6); 3.029 (0.5); 2.998 (1.0); 2.781 (4.0); 2.743 (7.3); 2.698 (1.9); 2.674 (3.2); 2.669 (4.3); 2.665 (3.3); 2.591 (1.1); 2.525 (9.4); 2.523 (13.6); 2.518 (18.4); 2.510 (238.4); 2.505 (517.3); 2.500 (721.0); 2.496 (506.0); 2.491 (228.9); 2.466 (0.6); 2.451 (1.1); 2.332 (3.0); 2.327 (4.2); 2.323 (2.9); 2.072 (1.4); 1.988 (5.9); 1.964 (6.9); 1.952 (7.3); 1.940 (7.8); 1.830 (2.6); 1.809 (4.2); 1.791 (4.4); 1.765 (3.0); 1.741 (2.4); 1.723 (2.9); 1.701 (3.0); 1.334 (0.9); 1.235 (1.0); 1.192 (1.3); 1.175 (2.4); 1.157 (1.3); 0.008 (4.8); 0.000 (163.2); −0.009 (5.0); −0.150 (0.5)

Example 1.64: $^1$H-NMR (400.0 MHz, d$_6$-DMSO): δ=8.738 (3.3); 8.718 (3.3); 8.117 (1.2); 7.899 (2.8); 7.893 (2.5); 7.889 (2.0); 7.884 (1.7); 7.881 (1.9); 7.701 (1.7); 7.683 (1.9); 7.558 (1.2); 7.537 (1.8); 7.517 (0.9); 7.031 (2.8); 7.024 (4.7); 7.003 (16.0); 6.982 (11.7); 6.823 (8.3); 6.811 (9.4); 6.800 (6.5); 6.789 (6.6); 5.530 (0.9); 5.122 (2.9); 5.108 (2.8); 4.302 (2.0); 4.282 (4.0); 4.263 (4.0); 4.201 (3.4); 4.181 (3.4); 4.056 (0.6); 4.039 (2.0); 4.021 (1.9); 4.003 (0.7); 3.307 (45.4); 2.998 (15.9); 2.675 (1.0); 2.670 (1.5); 2.666 (1.0); 2.591 (16.0); 2.523 (5.1); 2.510 (89.1); 2.506 (185.7); 2.501 (253.3); 2.496 (181.3); 2.492 (85.3); 2.332 (1.2); 2.328 (1.6); 2.323 (1.2); 2.097 (3.5); 2.033 (3.9); 1.988 (9.8); 1.352 (0.5); 1.335 (1.0); 1.317 (0.6); 1.279 (1.1); 1.247 (5.0); 1.193 (2.4); 1.175 (4.8); 1.157 (2.5); 0.875 (2.3); 0.858 (7.4); 0.841 (2.8); 0.008 (1.5); 0.000 (41.0); −0.008 (1.6)

Example 1.66: $^1$H-NMR (400.6 MHz, CDCl$_3$): δ=7.519 (4.8); 7.399 (0.9); 7.360 (1.4); 7.286 (5.9); 7.260 (870.0); 7.237 (2.2); 7.221 (5.3); 7.217 (5.5); 7.203 (8.4); 7.198 (9.1); 7.194 (5.7); 7.176 (4.4); 7.149 (6.4); 7.131 (4.0); 6.997 (4.8); 6.046 (1.5); 5.570 (0.8); 5.357 (1.2); 5.149 (1.8); 4.149 (1.2); 4.131 (3.2); 4.113 (3.3); 4.095 (0.9); 3.457 (1.5); 3.364 (4.0); 3.325 (16.0); 2.898 (1.4); 2.855 (3.5); 2.831 (2.9); 2.815 (4.3); 2.799 (2.6); 2.772 (1.6); 2.086 (1.6); 2.045 (15.6); 1.901 (5.6); 1.885 (5.5); 1.547 (43.6); 1.277 (5.0); 1.260 (9.9); 1.242 (4.2); 0.899 (1.2); 0.882 (4.1); 0.864 (1.7); 0.008 (6.8); 0.000 (220.5); −0.009 (6.3)

Example 1.67: $^1$H-NMR (400.0 MHz, CDCl$_3$): δ=7.518 (0.6); 7.270 (0.5); 7.269 (0.5); 7.268 (0.6); 7.2674 (0.7); 7.2666 (0.7); 7.266 (0.9); 7.265 (1.0); 7.264 (1.3); 7.2634 (1.7); 7.2625 (2.3); 7.259 (93.3); 7.256 (1.3); 7.255 (0.6); 7.209 (0.6); 7.165 (1.1); 7.146 (1.8); 7.120 (0.6); 7.089 (1.5); 7.068 (0.9); 6.995 (0.5); 2.966 (0.5); 2.954 (0.5); 2.944 (0.5); 2.874 (0.6); 2.626 (2.2); 2.335 (9.9); 1.921 (0.6); 1.919 (0.8); 1.907 (0.5); 1.900 (0.8); 1.897 (0.6); 1.889 (0.6); 1.887 (0.7); 1.868 (0.7); 1.551 (16.0); 0.882 (1.1); 0.008 (1.0); 0.000 (43.0); −0.009 (1.3)

Example 1.68: $^1$H-NMR (400.0 MHz, CDCl$_3$): δ=7.260 (80.3); 7.071 (1.8); 7.030 (11.6); 7.027 (11.2); 6.996 (0.6); 5.108 (0.5); 4.130 (1.4); 4.112 (1.4); 3.361 (1.2); 3.323 (5.5); 2.991 (0.9); 2.816 (0.6); 2.801 (1.2); 2.785 (0.6); 2.776 (0.8); 2.760 (1.4); 2.743 (0.8); 2.679 (0.9); 2.290

(16.0); 2.044 (6.9); 1.872 (1.6); 1.857 (1.7); 1.276 (2.2); 1.259 (4.3); 1.241 (1.9); 0.899 (0.6); 0.882 (2.0); 0.864 (0.8); 0.008 (1.0); 0.000 (34.8); −0.009 (1.0)

Example 1.69: $^1$H-NMR (400.0 MHz, CDCl$_3$): δ=7.269 (0.6); 7.268 (0.7); 7.2673 (0.8); 7.2665 (0.9); 7.266 (1.0); 7.265 (1.2); 7.264 (1.4); 7.263 (1.9); 7.260 (59.9); 7.257 (0.7); 7.221 (0.9); 7.124 (1.2); 7.017 (11.5); 7.014 (10.5); 6.970 (2.5); 5.298 (2.2); 3.025 (1.4); 2.997 (15.3); 2.988 (4.2); 2.803 (0.7); 2.787 (1.2); 2.766 (1.0); 2.750 (1.6); 2.734 (1.0); 2.708 (0.7); 2.692 (0.5); 2.312 (4.2); 2.284 (16.0); 2.266 (0.8); 2.052 (0.9); 2.043 (2.3); 2.040 (0.8); 1.927 (0.6); 1.920 (0.7); 1.913 (0.8); 1.901 (1.0); 1.897 (0.9); 1.879 (1.2); 1.865 (1.5); 1.849 (1.4); 1.699 (0.5); 1.693 (0.6); 1.684 (0.8); 1.677 (1.1); 1.668 (1.3); 1.663 (1.4); 1.447 (1.0) 1.276 (0.7); 1.258 (1.7); 1.240 (0.6); 0.008 (0.7); 0.003 (0.5); 0.002 (0.9); 0.000 (24.9); −0.0026 (1.2); −0.0034 (0.9); −0.004 (0.5); −0.008 (0.7)

Example 1.70: $^1$H-NMR (400.0 MHz, d$_6$-DMSO): δ=8.619 (1.0); 8.598 (1.0); 7.139 (2.3); 7.119 (3.3); 7.027 (4.0); 7.011 (2.8); 5.399 (0.8); 5.379 (0.8); 3.316 (31.9); 2.912 (0.7); 2.897 (0.7); 2.762 (0.8); 2.741 (0.7); 2.723 (0.5); 2.519 (0.6); 2.510 (8.2); 2.506 (17.9); 2.501 (25.1); 2.496 (17.5); 2.492 (7.7); 2.446 (0.5); 2.427 (0.6); 2.419 (0.6); 2.407 (0.7); 2.397 (0.6); 2.249 (16.0); 1.981 (1.2); 1.972 (0.5); 1.960 (1.2); 1.950 (1.1); 1.929 (1.0); 0.008 (0.5); 0.000 (18.3)

Example 1.71: $^1$H-NMR (400.0 MHz, CDCl$_3$): δ=7.260 (44.1); 7.157 (1.7); 7.138 (3.5); 7.083 (2.2); 7.062 (1.3); 4.130 (0.6); 4.112 (0.6); 3.026 (2.0); 2.998 (16.0); 2.990 (5.3); 2.974 (0.7); 2.965 (0.9); 2.956 (0.9); 2.943 (0.9); 2.935 (0.8); 2.885 (0.6); 2.865 (1.2); 2.845 (0.9); 2.825 (0.6); 2.335 (15.0); 2.043 (2.9); 1.906 (1.1); 1.895 (0.6); 1.887 (1.1); 1.874 (1.0); 1.866 (0.6); 1.855 (1.0); 1.651 (0.9); 1.463 (0.5); 1.446 (1.1); 1.428 (0.5); 1.276 (0.9); 1.258 (1.9); 1.240 (0.9); 0.000 (18.5); −0.009 (0.7)

Example 1.72: $^1$H-NMR (400.0 MHz, CDCl$_3$): δ=7.278 (0.5); 7.276 (0.8); 7.275 (0.8); 7.268 (69.7); 7.219 (0.7); 7.167 (2.0); 7.148 (3.2); 7.114 (1.1); 7.088 (2.5); 7.067 (1.5); 5.491 (0.8); 5.300 (0.7); 3.017 (0.5); 3.008 (0.8); 3.004 (0.5); 2.995 (0.6); 2.986 (0.9); 2.977 (0.9); 2.965 (0.9); 2.956 (0.9); 2.880 (1.0); 2.861 (0.8); 2.840 (1.7); 2.717 (5.5); 2.330 (16.0); 1.969 (0.8); 1.949 (1.4); 1.938 (0.9); 1.930 (1.4); 1.927 (1.0); 1.919 (1.1); 1.917 (1.3); 1.909 (0.8); 1.898 (1.2); 1.877 (0.7); 1.737 (6.4); 1.277 (1.0); 1.265 (2.3); 1.259 (1.8); 1.241 (0.5); 1.237 (1.3); 1.220 (1.2); 0.899 (1.3); 0.882 (4.6); 0.864 (1.7); 0.008 (0.8); 0.000 (30.3); −0.009 (0.9)

Example 1.73: $^1$H-NMR (400.0 MHz, CDCl$_3$): δ=7.519 (0.5); 7.260 (87.4); 7.210 (0.6); 7.172 (1.8); 7.152 (3.1); 7.097 (3.4); 7.078 (1.5); 6.996 (0.5); 5.449 (0.6); 5.431 (0.6); 4.130 (1.2); 4.112 (1.2); 3.326 (4.5); 2.991 (0.7); 2.987 (0.8); 2.978 (0.9); 2.966 (0.8); 2.956 (0.9); 2.882 (1.0); 2.862 (0.8); 2.842 (0.6); 2.341 (16.0); 2.044 (5.6); 1.934 (0.9); 1.923 (0.6); 1.915 (0.9); 1.902 (0.9); 1.883 (0.8); 1.571 (7.3); 1.276 (1.9); 1.270 (1.1); 1.265 (1.1); 1.259 (3.8); 1.241 (1.7); 0.899 (0.5); 0.882 (1.9); 0.864 (0.7); 0.008 (0.9); 0.000 (36.3); −0.009 (1.2)

Example 1.74: $^1$H-NMR (400.0 MHz, d$_6$-DMSO): δ=7.828 (0.5); 7.556 (0.5); 7.138 (1.7); 7.118 (2.4); 7.020 (3.5); 7.006 (1.6); 4.345 (1.1); 4.329 (3.6); 4.311 (3.9); 4.293 (1.3); 3.315 (13.9); 2.999 (1.8); 2.922 (0.5); 2.915 (0.6); 2.900 (0.5); 2.894 (0.5); 2.592 (1.7); 2.511 (6.2); 2.506 (13.4); 2.501 (18.7); 2.497 (13.0); 2.492 (5.8); 2.244 (12.2); 1.995 (1.1); 1.989 (1.1); 1.974 (1.1); 1.964 (1.0); 1.943 (0.9); 1.343 (7.1); 1.325 (16.0); 1.307 (6.9); 1.246 (0.8); 1.175 (0.7); 0.858 (1.5); 0.840 (0.5); 0.000 (8.0)

Example 1.75: $^1$H-NMR (400.0 MHz, d$_6$-DMSO): δ=8.416 (0.6); 8.396 (0.6); 7.905 (0.6); 7.816 (0.6); 7.140 (2.2); 7.121 (3.1); 7.029 (7.0); 7.010 (2.0); 5.416 (0.5); 3.313 (0.9); 3.169 (1.3); 2.954 (0.5); 2.931 (0.6); 2.915 (0.8); 2.900 (0.8); 2.767 (0.8); 2.748 (0.7); 2.729 (0.5); 2.524 (0.7); 2.519 (1.0); 2.510 (16.9); 2.506 (37.5); 2.501 (52.7); 2.497 (37.4); 2.492 (17.4); 2.456 (1.4); 2.451 (1.5); 2.447 (1.3); 2.248 (16.0); 1.996 (1.3); 1.987 (0.6); 1.975 (1.4); 1.965 (1.3); 1.953 (0.6); 1.944 (1.2); 0.008 (0.9); 0.000 (33.6); −0.009 (1.1)

Example 1.76: $^1$H-NMR (400.0 MHz, CDCl$_3$): δ=7.266 (0.5); 7.260 (40.9); 7.158 (1.6); 7.138 (3.7); 7.079 (2.0); 7.058 (1.2); 2.990 (15.9); 2.977 (16.0); 2.968 (0.8); 2.958 (0.8); 2.945 (0.8); 2.936 (0.8); 2.868 (1.0); 2.848 (0.8); 2.829 (0.5); 2.327 (13.4); 2.043 (2.1); 1.913 (1.0); 1.902 (0.5); 1.894 (1.0); 1.881 (0.9); 1.862 (0.9); 1.602 (1.0); 1.276 (1.0); 1.265 (0.9); 1.258 (1.7); 1.240 (0.7); 0.899 (0.5); 0.882 (1.9); 0.864 (0.7); 0.000 (18.9); −0.009 (0.5)

Example 1.77: $^1$H-NMR (400.0 MHz, CDCl$_3$): δ=7.519 (0.5); 7.270 (0.6); 7.269 (0.7); 7.2674 (1.0); 7.2665 (1.1); 7.265 (1.7); 7.260 (80.5); 7.256 (0.7); 7.157 (2.6); 7.149 (2.5); 7.139 (3.4); 7.076 (2.3); 7.056 (1.4); 4.148 (0.9); 4.130 (2.9); 4.112 (2.9); 4.095 (1.0); 3.364 (5.0); 3.140 (6.3); 2.973 (0.5); 2.965 (0.8); 2.956 (0.9); 2.943 (0.9); 2.935 (0.8); 2.885 (0.6); 2.864 (1.3); 2.844 (1.0); 2.825 (0.7); 2.331 (16.0); 2.043 (13.5); 1.934 (0.5); 1.913 (1.3); 1.902 (0.6); 1.894 (1.2); 1.881 (1.2); 1.873 (0.6); 1.862 (1.1); 1.587 (0.8); 1.276 (4.2); 1.258 (8.8); 1.241 (4.1); 0.882 (0.9); 0.008 (1.0); 0.000 (36.9); −0.009 (1.1)

Example 1.78: $^1$H-NMR (400.0 MHz, d$_6$-DMSO): δ=8.035 (0.6); 7.363 (0.6); 7.131 (2.2); 7.112 (3.0); 7.019 (6.3); 7.000 (1.9); 6.999 (1.8); 4.039 (0.8); 4.021 (0.8); 3.315 (18.2); 2.945 (0.5); 2.930 (0.6); 2.923 (0.6); 2.913 (0.8); 2.906 (0.8); 2.891 (0.8); 2.884 (0.7); 2.761 (0.9); 2.741 (0.7); 2.722 (0.6); 2.519 (0.6); 2.510 (8.4); 2.506 (18.4); 2.501 (25.7); 2.497 (17.8); 2.492 (7.8); 2.429 (0.5); 2.245 (16.0); 2.008 (0.5); 1.988 (4.2); 1.977 (0.6); 1.965 (1.4); 1.955 (1.3); 1.943 (0.6); 1.933 (1.2); 1.193 (1.1); 1.175 (2.2); 1.157 (1.1); 0.000 (3.9)

Example 1.79: $^1$H-NMR (400.0 MHz, CDCl$_3$): δ=7.636 (5.3); 7.631 (2.1); 7.615 (6.7); 7.485 (7.8); 7.480 (2.4); 7.469 (2.6); 7.464 (5.4); 7.259 (32.9); 7.086 (3.9); 7.069 (3.3); 7.039 (2.9); 7.019 (1.4); 5.095 (2.4); 4.129 (1.4); 4.111 (1.4); 3.067 (1.0); 3.048 (1.1); 3.029 (1.2); 3.010 (1.3); 2.554 (2.2); 2.530 (1.2); 2.515 (0.9); 2.492 (1.0); 2.311 (16.0); 2.282 (1.2); 2.262 (0.9); 2.042 (6.0); 1.338 (0.7); 1.303 (11.4); 1.287 (11.8); 1.276 (4.7); 1.265 (6.0); 1.258 (6.3); 1.240 (2.5); 0.899 (2.6); 0.882 (7.2); 0.864 (3.2); 0.008 (0.6); 0.000 (12.3)

Example 1.80: $^1$H-NMR (400.0 MHz, CDCl$_3$): δ=7.259 (60.2); 7.076 (1.6); 7.057 (3.5); 7.048 (2.8); 7.026 (2.7); 7.007 (1.2); 6.786 (2.5); 6.757 (2.7); 6.742 (2.9); 6.713 (2.9); 6.088 (1.6); 6.044 (1.4); 5.519 (4.0); 5.516 (3.9); 5.491 (3.8); 5.488 (3.9); 5.057 (2.4); 4.130 (1.6); 4.112 (1.6); 4.094 (0.5); 3.054 (1.1); 3.035 (1.2); 3.016 (1.3); 2.996 (1.3); 2.539 (0.9); 2.517 (1.1); 2.501 (0.8); 2.478 (1.0); 2.296 (16.0); 2.280 (1.0); 2.260 (1.0); 2.242 (0.8); 2.044 (7.4); 1.304 (0.6); 1.281 (12.9); 1.276 (4.6); 1.264 (15.2); 1.258 (7.2); 1.240 (4.0); 0.899 (1.8); 0.882 (6.9); 0.864 (2.6); 0.008 (0.6); 0.000 (26.1); −0.009 (0.8)

Example 1.81: $^1$H-NMR (400.0 MHz, CDCl$_3$): δ=7.518 (2.1); 7.290 (0.5); 7.259 (358.1); 7.209 (2.2); 7.105 (1.7); 7.086 (3.3); 7.066 (1.9); 7.046 (2.7); 7.027 (1.3); 6.995 (2.0); 6.348 (1.9); 6.345 (5.0); 6.341 (4.9); 6.338 (1.7); 5.981 (1.8); 5.977 (5.0); 5.974 (5.0); 5.970 (1.8); 4.961 (1.9); 3.094 (1.2); 3.074 (1.3); 3.055 (1.5); 3.036 (1.5); 2.559 (0.9); 2.535 (1.1); 2.519 (0.8); 2.497 (1.1); 2.343

(0.5); 2.312 (16.0); 2.284 (0.9); 2.264 (0.5); 2.026 (0.5); 1.732 (0.5); 1.541 (3.7); 1.495 (0.6); 1.491 (0.6); 1.323 (3.0); 1.294 (12.5); 1.284 (2.1); 1.277 (9.4); 1.269 (4.8); 1.259 (3.3); 1.243 (2.6); 1.209 (3.0); 1.193 (3.0); 0.882 (1.5); 0.864 (0.6); 0.008 (3.6); 0.000 (141.8); −0.009 (4.1); −0.050 (0.9)

Example 1.87: $^1$H-NMR (400.6 MHz, $d_6$-DMSO): δ=8.6232 (2.4); 8.6013 (2.4); 7.9920 (1.4); 7.2133 (7.2); 7.2063 (16.0); 7.1953 (2.5); 7.1842 (2.7); 7.1762 (2.8); 7.1658 (4.0); 7.1570 (3.7); 7.1444 (2.1); 7.1205 (7.1); 7.1025 (3.6); 6.9008 (0.9); 5.7607 (1.4); 5.5596 (0.7); 5.4129 (3.7); 5.4004 (4.2); 5.2366 (1.4); 5.2171 (2.4); 5.1976 (1.4); 4.4550 (1.0); 4.4366 (2.7); 4.4188 (3.1); 4.4052 (2.3); 4.3870 (0.8); 3.4495 (0.6); 3.3886 (0.9); 3.3684 (7.5); 3.3478 (382.5); 3.3244 (6.7); 3.3055 (20.7); 3.2816 (0.5); 3.1942 (2.8); 3.1761 (2.8); 3.1556 (3.4); 3.1375 (3.0); 2.9765 (0.7); 2.7490 (1.9); 2.7296 (1.9); 2.7105 (1.6); 2.6910 (1.2); 2.6781 (0.6); 2.5179 (28.9); 2.5137 (57.4); 2.5092 (76.8); 2.5047 (56.0); 2.4765 (0.5); 1.9958 (0.7); 1.2431 (0.8)

Example 1.82: $^1$H-NMR (400.6 MHz, MeOD): δ=7.2752 (0.8); 7.2396 (16.0); 7.2278 (11.9); 5.4090 (1.4); 4.9255 (0.5); 4.8765 (83.3); 4.4781 (1.2); 4.4608 (3.0); 4.4443 (3.1); 4.4268 (1.3); 3.3372 (8.3); 3.3332 (15.6); 3.3291 (23.1); 3.3252 (16.8); 3.3212 (8.9); 3.3096 (4.7); 3.2884 (4.9); 3.2705 (4.5); 2.8872 (2.1); 2.8695 (2.1); 2.8478 (1.9); 2.8303 (1.8)

Example 1.101: $^1$H-NMR (400.0 MHz, CDCl$_3$): δ=7.2596 (45.1); 7.0743 (1.5); 7.0554 (3.0); 7.0344 (3.0); 7.0212 (2.6); 7.0021 (1.2); 5.5520 (1.0); 5.2974 (1.7); 4.8164 (16.0); 4.1475 (0.6); 4.1296 (1.7); 4.1117 (1.7); 4.0939 (0.6); 3.0502 (1.0); 3.0309 (1.2); 3.0117 (1.3); 2.9924 (1.3); 2.5334 (1.0); 2.5107 (1.1); 2.4949 (0.9); 2.4722 (1.0); 2.2933 (14.9); 2.2660 (0.8); 2.2470 (1.0); 2.2288 (0.8); 2.0430 (7.9); 2.0074 (0.6); 1.2757 (3.6); 1.2711 (11.0); 1.2579 (6.8); 1.2543 (11.0); 1.2401 (2.4); 0.0080 (0.6); −0.0002 (16.9); −0.0084 (0.5)

Example 1.140: $^1$H-NMR (400.6 MHz, MeOD): δ=7.3046 (3.6); 7.2843 (7.3); 7.2732 (2.7); 7.2582 (5.1); 7.2393 (4.9); 7.2209 (3.0); 7.2034 (0.9); 5.4693 (1.3); 4.8742 (111.1); 4.6656 (1.8); 4.1465 (1.3); 4.1286 (3.6); 4.1108 (3.6); 4.0930 (1.2); 3.3375 (9.8); 3.3334 (18.8); 3.3293 (26.8); 3.3252 (18.4); 3.3211 (9.1); 3.2149 (1.0); 3.2033 (1.0); 3.1740 (1.5); 3.1628 (1.3); 3.0096 (3.7); 3.0067 (3.8); 2.9685 (2.5); 2.6912 (0.9); 2.6096 (0.6); 2.0317 (16.0); 1.3442 (1.0); 1.3305 (1.0); 1.3085 (0.8); 1.2770 (4.3); 1.2591 (8.4); 1.2413 (4.1); 0.9204 (0.8)

Example 1.91: $^1$H-NMR (400.6 MHz, MeOD): δ=7.3040 (7.6); 7.2837 (16.0); 7.2771 (8.8); 7.2730 (7.0); 7.2591 (10.8); 7.2576 (11.3); 7.2375 (10.6); 7.2200 (6.7); 7.2028 (2.3); 5.6777 (0.7); 5.5083 (1.9); 5.4679 (2.9); 4.8977 (2.2); 4.8747 (217.5); 4.8496 (2.7); 4.6663 (4.1); 3.3526 (0.8); 3.3375 (19.6); 3.3333 (38.2); 3.3292 (56.7); 3.3252 (39.3); 3.3210 (20.3); 3.3042 (1.2); 3.3000 (1.1); 3.2956 (0.9); 3.2150 (2.3); 3.2023 (2.2); 3.1737 (3.4); 3.1611 (3.0); 3.0095 (7.7); 3.0063 (8.1); 2.9685 (5.4); 2.9652 (5.4); 2.7232 (1.0); 2.6908 (2.2); 2.0315 (2.0); 1.3463 (1.4); 1.3273 (2.4); 1.3082 (6.4); 1.2768 (1.2); 1.2589 (1.5); 1.2411 (0.8); 0.9372 (3.1); 0.9203 (11.0); 0.9026 (4.2)

Example 1.90: $^1$H-NMR (400.0 MHz, $d_6$-DMSO): δ=8.6554 (2.4); 8.6334 (2.5); 8.0343 (0.6); 8.0131 (0.6); 7.6352 (0.7); 7.2244 (0.6); 7.2075 (3.8); 7.2044 (5.0); 7.1999 (5.8); 7.1938 (15.3); 7.1918 (16.0); 7.1804 (2.1); 7.1685 (2.7); 7.1607 (3.8); 7.1500 (3.8); 7.1417 (3.6); 7.1284 (2.0); 7.0868 (5.6); 7.0683 (3.5); 5.5649 (0.6); 5.4050 (3.8); 5.3923 (4.1); 5.3636 (0.9); 5.3495 (0.8); 5.2155 (1.5); 5.1956 (2.4); 5.1758 (1.5); 4.4438 (0.5); 4.4251 (1.7); 4.4074 (2.2); 4.3936 (2.0); 4.3755 (0.9); 3.3651 (1.0); 3.3142 (134.9); 3.1796 (2.0); 3.1614 (2.2); 3.1409 (2.6); 3.1226 (2.3); 2.7377 (1.9); 2.7179 (1.8); 2.6964 (1.7); 2.6945 (1.7); 2.6787 (1.5); 2.6694 (0.8); 2.6648 (0.5); 2.5550 (0.6); 2.5506 (0.6); 2.5228 (2.4); 2.5181 (3.4); 2.5094 (37.0); 2.5049 (76.7); 2.5003 (105.5); 2.4957 (73.2); 2.4912 (33.5); 2.3271 (0.7); 1.9828 (1.0); −0.0002 (14.4)

Example 1.139: $^1$H-NMR (400.0 MHz, $d_6$-DMSO): δ=7.2584 (2.0); 7.2411 (4.0); 7.2317 (1.3); 7.2279 (1.3); 7.2124 (2.4); 7.2081 (1.5); 7.1954 (1.4); 7.1905 (2.2); 7.1866 (1.6); 7.1716 (1.4); 5.7518 (6.8); 5.1244 (0.8); 4.5305 (0.9); 4.0380 (0.9); 4.0202 (0.9); 3.3143 (5.4); 3.0973 (0.5); 3.0853 (0.5); 3.0570 (0.8); 3.0446 (0.7); 2.9808 (0.7); 2.9427 (16.0); 2.8866 (1.3); 2.8465 (0.9); 2.5226 (0.7); 2.5179 (1.0); 2.5091 (10.4); 2.5046 (21.5); 2.5000 (29.5); 2.4954 (20.4); 2.4909 (9.3); 1.9874 (4.3); 1.1921 (1.3); 1.1743 (2.6); 1.1565 (1.2); −0.0002 (6.2)

Example 1.138: $^1$H-NMR (400.0 MHz, $d_6$-DMSO): δ=7.8905 (0.8); 7.8870 (0.6); 7.8853 (0.6); 7.2586 (2.1); 7.2410 (4.2); 7.2316 (1.4); 7.2280 (1.4); 7.2126 (2.4); 7.2083 (1.6); 7.1955 (1.4); 7.1906 (2.2); 7.1717 (1.4); 5.7520 (2.2); 5.1234 (0.7); 4.5287 (0.9); 4.0381 (1.5); 4.0203 (1.5); 3.3125 (6.6); 3.0975 (0.6); 3.0849 (0.6); 3.0571 (0.8); 3.0449 (0.8); 2.9810 (0.9); 2.9428 (16.0); 2.8865 (1.3); 2.8460 (0.9); 2.5227 (1.0); 2.5180 (1.5); 2.5093 (14.8); 2.5047 (30.6); 2.5002 (42.0); 2.4956 (28.9); 2.4910 (13.1); 1.9875 (6.9); 1.2368 (0.6); 1.1922 (2.0); 1.1744 (4.0); 1.1566 (2.0); 1.0703 (0.5); 1.0542 (0.5); −0.0002 (8.5)

Example 1.88: $^1$H-NMR (400.6 MHz, MeOD): δ=7.3208 (1.9); 7.3033 (4.2); 7.2851 (3.5); 7.2797 (2.2); 7.2781 (1.9); 7.2758 (2.0); 7.2741 (1.8); 7.2619 (3.2); 7.2603 (3.4); 7.2584 (2.7); 7.2429 (3.8); 7.2381 (2.9); 7.2244 (2.2); 7.2201 (1.8); 7.2066 (0.7); 5.5092 (16.0); 5.4823 (0.8); 4.8741 (41.5); 4.6780 (1.2); 4.1466 (0.6); 4.1288 (1.9); 4.1109 (1.9); 4.0931 (0.7); 3.3373 (5.4); 3.3333 (10.4); 3.3293 (14.6); 3.3252 (10.7); 3.3212 (6.0); 3.2945 (22.6); 3.2228 (0.9); 3.2106 (0.8); 3.1809 (1.1); 3.1694 (1.1); 3.0132 (2.5); 3.0101 (2.6); 2.9722 (1.8); 2.9690 (1.8); 2.0318 (9.0); 1.3090 (0.9); 1.2771 (2.6); 1.2592 (5.2); 1.2414 (2.6)

Example 1.137: $^1$H-NMR (400.6 MHz, MeOD): δ=7.3216 (2.9); 7.3041 (6.2); 7.2858 (5.2); 7.2764 (2.9); 7.2610 (4.8); 7.2438 (5.7); 7.2389 (4.4); 7.2254 (3.2); 7.2081 (1.1); 5.5097 (16.0); 5.4802 (1.2); 4.8751 (78.2); 4.6759 (2.0); 4.1469 (0.5); 4.1291 (1.6); 4.1112 (1.6); 4.0936 (0.5); 3.3372 (11.1); 3.3333 (20.8); 3.3293 (28.7); 3.3253 (21.4); 3.3214 (12.1); 3.2961 (30.2); 3.2227 (1.4); 3.2112 (1.4); 3.1813 (1.8); 3.1712 (1.7); 3.0107 (3.9); 2.9697 (2.6); 2.0321 (7.3); 1.3092 (1.2); 1.2773 (2.0); 1.2595 (4.0); 1.2417 (2.0)

Example 1.95: $^1$H-NMR (400.6 MHz, CDCl$_3$): δ=8.0523 (0.7); 7.5198 (0.6); 7.4128 (0.6); 7.3932 (0.9); 7.2875 (0.7); 7.2862 (0.7); 7.2831 (1.3); 7.2741 (4.2); 7.2717 (5.6); 7.2614 (106.3); 7.2557 (1.7); 7.2548 (1.5); 7.2540 (1.4); 7.2533 (1.3); 7.2524 (1.2); 7.2508 (0.8); 7.2500 (0.9); 7.2492 (0.8); 7.2476 (0.7); 7.2468 (0.6); 7.2461 (0.6); 7.2444 (0.7); 7.2436 (0.6); 7.2405 (1.1); 7.2357 (1.6); 7.2342 (1.7); 7.2285 (1.2); 7.2222 (1.0); 7.2127 (0.9); 7.2032 (1.0); 7.1921 (0.7); 6.9977 (0.6); 6.8516 (0.7); 6.8318 (0.8); 5.4976 (0.7); 5.4842 (0.8); 5.4760 (0.7); 5.4633 (0.7); 5.3954 (1.3); 4.3177 (0.6); 4.2189 (0.7); 4.2089 (1.0); 4.1971 (0.6); 3.4071 (2.1); 3.3972 (16.0); 3.1904 (0.6); 3.1494 (1.2); 3.1258 (0.8); 3.0797

(0.5); 3.0688 (0.6); 3.0479 (0.9); 3.0366 (0.9); 3.0064 (0.5); 2.0877 (1.0); 1.7916 (0.8); 0.0080 (1.6); −0.0002 (57.9); −0.0085 (1.5)

Example 1.93: $^1$H-NMR (400.6 MHz, d$_6$-DMSO): δ=7.2885 (1.1); 7.2705 (1.9); 7.2501 (2.9); 7.2469 (3.7); 7.2288 (2.3); 7.2109 (1.1); 7.2080 (0.8); 7.1982 (1.7); 7.1934 (1.3); 7.1805 (1.7); 7.1759 (1.4); 7.1629 (0.6); 7.1584 (0.5); 4.2042 (0.9); 3.4093 (0.6); 3.4037 (0.6); 3.3990 (0.6); 3.3949 (0.7); 3.3923 (0.8); 3.3886 (2.1); 3.3854 (1.3); 3.3775 (2.2); 3.3743 (1.8); 3.3658 (3.8); 3.3618 (5.6); 3.3391 (2197.7); 3.3212 (3.4); 3.3197 (3.3); 3.3143 (1.3); 3.3133 (1.1); 3.3092 (0.6); 3.3077 (0.7); 3.3070 (0.7); 3.2977 (1.7); 3.2903 (0.7); 3.2879 (0.7); 3.2839 (0.8); 3.2741 (16.0); 3.1010 (0.8); 3.0201 (0.6); 3.0065 (0.6); 2.6757 (1.2); 2.6710 (1.7); 2.6664 (1.2); 2.5248 (3.8); 2.5201 (4.9); 2.5114 (97.7); 2.5068 (214.7); 2.5022 (302.0); 2.4976 (207.4); 2.4931 (92.7); 2.4729 (0.8); 2.4660 (0.6); 2.4611 (0.7); 2.4570 (0.6); 2.3385 (0.6); 2.3339 (1.4); 2.3293 (1.9); 2.3246 (1.4); 2.3201 (0.7); 1.9886 (1.3); 1.2475 (0.8); 1.1745 (0.8); 0.8584 (1.8); 0.8407 (0.6); 0.0079 (0.7); −0.0002 (33.6); −0.0085 (1.1)

Example 1.136: $^1$H-NMR (400.0 MHz, CDCl$_3$): δ=7.5186 (0.5); 7.3097 (0.8); 7.2597 (85.7); 7.2497 (2.0); 7.2433 (1.6); 7.2219 (0.5); 7.2180 (0.5); 7.2108 (0.5); 4.1305 (0.9); 4.1126 (1.0); 3.3917 (16.0); 3.3899 (13.6); 3.1606 (0.6); 3.1200 (1.1); 3.0413 (0.8); 3.0286 (0.8); 2.9999 (5.7); 2.9610 (0.8); 2.0436 (4.3); 1.5464 (2.3); 1.2764 (1.3); 1.2585 (2.8); 1.2407 (1.2); 0.0080 (1.4); −0.0002 (47.7); −0.0085 (1.6)

Example 1.83: $^1$H-NMR (400.0 MHz, CDCl$_3$): δ=7.2595 (41.1); 7.2437 (5.6); 7.2257 (2.3); 7.2064 (0.9); 7.1920 (1.5); 7.1740 (2.6); 7.1212 (0.9); 4.1457 (1.2); 4.1278 (3.5); 4.1099 (3.6); 4.0921 (1.2); 3.2229 (1.0); 3.2110 (1.0); 3.1814 (1.5); 3.1700 (1.4); 3.0202 (3.2); 2.9791 (2.2); 2.0414 (16.0); 1.2748 (4.4); 1.2570 (9.0); 1.2391 (4.3); 0.0698 (1.0); −0.0002 (15.0)

Example 1.84: $^1$H-NMR (400.0 MHz, CDCl$_3$): δ=7.5182 (1.3); 7.3092 (0.7); 7.2593 (233.6); 7.2445 (6.8); 7.2300 (5.3); 7.2128 (8.0); 7.1757 (2.7); 7.1611 (2.9); 6.9952 (1.5); 5.2976 (16.0); 4.8038 (1.3); 4.1288 (1.0); 4.1111 (1.0); 3.2326 (2.8); 3.2203 (2.8); 3.1913 (4.2); 3.1791 (3.9); 3.0275 (7.3); 3.0244 (7.3); 2.9860 (5.1); 2.9830 (4.9); 2.8929 (0.8); 2.0422 (4.6); 1.5706 (4.1); 1.2754 (1.4); 1.2576 (3.3); 1.2397 (1.7); 0.0080 (2.5); −0.0002 (79.4); −0.0085 (2.1)

Example 1.105: $^1$H-NMR (400.0 MHz, CDCl$_3$): δ=7.2594 (27.4); 7.0824 (1.0); 7.0628 (3.7); 7.0221 (1.5); 7.0180 (1.2); 7.0015 (0.8); 4.1291 (1.0); 4.1112 (1.0); 3.0592 (0.7); 3.0400 (0.7); 3.0206 (0.8); 3.0015 (0.8); 2.5349 (0.6); 2.5124 (0.6); 2.4966 (0.5); 2.4741 (0.6); 2.2962 (9.3); 2.2746 (0.8); 2.2550 (0.8); 2.2377 (0.6); 2.0423 (4.6); 1.7104 (16.0); 1.7090 (15.8); 1.2829 (7.4); 1.2756 (2.1); 1.2661 (7.5); 1.2577 (3.3); 1.2398 (1.5); −0.0002 (10.0)

Example 1.103: $^1$H-NMR (400.0 MHz, CDCl$_3$): δ=7.5186 (0.5); 7.2597 (84.6); 7.0875 (1.8); 7.0685 (3.4); 7.0533 (2.7); 7.0268 (2.6); 7.0075 (1.4); 6.9957 (0.6); 5.6023 (0.9); 5.2980 (3.4); 5.1096 (1.1); 5.0930 (3.1); 5.0764 (3.2); 5.0598 (1.1); 4.1478 (1.1); 4.1300 (3.5); 4.1121 (3.6); 4.0942 (1.2); 3.0667 (1.2); 3.0476 (1.3); 3.0282 (1.4); 3.0089 (1.5); 2.5409 (1.0); 2.5186 (1.2); 2.5027 (0.9); 2.4797 (1.0); 2.2977 (15.7); 2.2811 (1.2); 2.2623 (1.2); 2.2435 (0.8); 2.0432 (16.0); 1.6467 (10.4); 1.6452 (9.8); 1.6301 (10.7); 1.6287 (9.8); 1.2833 (7.5); 1.2798 (7.4); 1.2761 (6.2); 1.2665 (7.7); 1.2630 (7.5); 1.2582 (10.6); 1.2404 (4.8); 0.0079 (1.1); −0.0002 (33.3); −0.0085 (1.2)

Example 1.96: $^1$H-NMR (400.0 MHz, CDCl$_3$): δ=7.2595 (28.9); 7.2464 (1.2); 7.2336 (0.7); 3.3848 (16.0); 2.0432 (1.2); 1.4658 (1.6); 1.4480 (3.2); 1.4301 (1.6); 1.2582 (0.8); −0.0002 (10.7)

Example 1.141: $^1$H-NMR (400.0 MHz, CDCl$_3$): δ=7.2591 (70.4); 7.0837 (1.2); 7.0638 (2.8); 7.0321 (3.2); 7.0157 (3.0); 5.3266 (0.9); 4.1302 (0.9); 4.1123 (0.9); 3.6459 (8.5); 3.0621 (1.0); 3.0428 (1.2); 3.0236 (1.2); 3.0042 (1.3); 2.5441 (0.9); 2.5213 (1.0); 2.5056 (0.8); 2.4826 (0.9); 2.2998 (16.0); 2.2653 (0.6); 2.0431 (4.0); 1.2757 (2.9); 1.2711 (10.4); 1.2579 (4.8); 1.2544 (9.9); 1.2403 (1.4); 0.8988 (0.7); 0.8818 (2.3); 0.8641 (0.9); 0.0079 (0.7); −0.0002 (24.8); −0.0085 (0.8)

Example 1.143: $^1$H-NMR (400.0 MHz, CDCl$_3$): δ=7.2591 (8.0); 7.0042 (0.5); 2.2925 (2.3); 1.2597 (2.0); 1.2429 (1.7); 0.8818 (0.6); 0.3010 (0.6); 0.2922 (16.0); 0.2833 (0.5); −0.0002 (3.0)

Example 1.145: $^1$H-NMR (400.0 MHz, CDCl$_3$): δ=7.2593 (56.4); 7.0821 (2.0); 7.0620 (1.2); 7.0133 (0.9); 6.9952 (0.8); 5.1820 (0.6); 5.1602 (1.0); 5.1391 (0.6); 4.1305 (0.5); 4.1126 (0.5); 4.0816 (1.0); 4.0458 (16.0); 4.0113 (1.0); 3.0207 (0.5); 3.0009 (0.6); 2.2940 (6.2); 2.0434 (2.3); 1.5600 (1.0); 1.2828 (5.6); 1.2764 (1.1); 1.2659 (5.5); 1.2585 (1.7); 1.2406 (0.7); 0.0079 (0.6); −0.0002 (20.1); −0.0085 (0.6)

Example 1.147: $^1$H-NMR (400.0 MHz, CDCl$_3$): δ=7.26 (21.0); 7.08 (0.6); 7.06 (1.3); 7.02 (2.8); 7.01 (0.6); 3.03 (0.5); 3.01 (0.6); 2.99 (0.6); 2.29 (7.4); 2.17 (17.4); 1.27 (5.4); 1.25 (5.2); 0.00 (18.5)

Example 1.149: $^1$H-NMR (400.6 MHz, CDCl$_3$): δ=8.81 (1.8); 8.70 (1.3); 7.26 (21.0); 7.14 (1.9); 7.12 (3.9); 7.08 (3.6); 7.06 (2.6); 7.00 (1.5); 5.61 (0.6); 5.27 (0.7); 3.16 (0.8); 3.14 (0.9); 3.12 (1.0); 3.10 (1.0); 2.76 (5.9); 2.74 (7.0); 2.60 (0.7); 2.58 (0.9); 2.57 (0.6); 2.45 (0.6); 2.43 (1.0); 2.42 (1.0); 2.40 (0.6); 2.33 (0.6); 2.31 (17.5); 1.58 (2.1); 1.34 (2.5); 1.32 (2.7); 1.29 (3.4); 1.27 (3.0); 1.01 (0.6); 0.99 (0.6) 0.00 (19.6)

Example 1.107: $^1$H-NMR (400.6 MHz, CDCl$_3$): δ=8.3244 (0.7); 7.2607 (5.0); 7.1277 (1.8); 7.1082 (3.2); 7.0592 (5.9); 7.0407 (1.8); 5.7635 (0.2); 5.3068 (0.4); 3.4285 (0.4); 3.1276 (1.2); 3.1085 (1.3); 3.0890 (1.5); 3.0699 (1.5); 2.5807 (1.0); 2.5595 (1.2); 2.5422 (0.9); 2.5210 (1.1); 2.4098 (0.5); 2.3906 (1.1); 2.3735 (1.3); 2.3722 (1.3); 2.3535 (1.0); 23336 (0.6); 2.3039 (17.6); 1.6388 (63.1); 1.2982 (10.7); 1.2813 (10.9); −0.0002 (0.7)

Example 1.109: $^1$H-NMR (400.6 MHz, CDCl$_3$) δ=8.2973 (3.3); 7.2606 (34.0); 7.1296 (1.3); 7.1095 (2.3); 7.0590 (2.2); 7.0493 (1.6); 7.0433 (2.0); 5.0781 (1.5); 5.0617 (1.5); 5.0453 (0.5); 3.1276 (0.8); 3.1084 (0.9); 3.0889 (1.0); 3.0697 (1.0); 2.5872 (0.7); 2.5655 (0.8); 2.5488 (0.6); 2.5270 (0.7); 2.3792 (0.6); 2.3602 (0.7); 2.3412 (0.6); 2.3268 (0.8); 2.3068 (11.5); 1.6290 (15.8); 1.6126 (16.0); 1.5892 (0.6); 1.5838 (0.6); 1.5786 (0.5); 1.3247 (0.7); 1.3074 (1.3); 1.3013 (6.7); 1.2845 (6.8); 1.2644 (1.1); 1.2594 (1.2); 1.2562 (1.2); 0.8820 (1.4); 0.8643 (0.6); −0.0002 (5.2)

B. FORMULATION EXAMPLES a) A dusting product is obtained by mixing 10 parts by weight of a compound of the formula (I) and/or salts thereof and 90 parts by weight of talc as an inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a friction ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
75 parts by weight of a compound of the formula (I) and/or salts thereof,
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill, and granulating the powder in a fluidized bed by spray application of water as a granulating liquid.

f) Water-dispersible granules are also obtained by homogenizing and precomminuting, in a colloid mill,
25 parts by weight of a compound of the formula (I) and/or salts thereof,
5 parts by weight of sodium 2,2'-dinaphthylmethane-6,6'-disulfonate
2 parts by weight of sodium oleoylmethyltaurate,
1 part by weight of polyvinyl alcohol,
17 parts by weight of calcium carbonate and
50 parts by weight of water,
then grinding the mixture in a bead mill and atomizing and drying the resulting suspension in a spray tower by means of a one-phase nozzle.

C. BIOLOGICAL EXAMPLES

Test Description

1. Pre-Emergence Herbicidal Effect and Crop Plant Compatibility

Seeds of monocotyledonous and dicotyledonous weed plants and crop plants are laid out in sandy loam soil in wood-fiber pots and covered with soil. The compounds of the invention, formulated in the form of wettable powders (WP) or as emulsion concentrates (EC), are then applied to the surface of the covering soil as aqueous suspension or emulsion at a water application rate equating to 600 to 800 L/ha with addition of 0.2% wetting agent.

After the treatment, the pots are placed in a greenhouse and kept under good growth conditions for the trial plants. The damage to the test plants is scored visually after a test period of 3 weeks by comparison with untreated controls (herbicidal activity in percent (%): 100% activity=the plants have died, 0% activity=like control plants).

In the tables below, the following abbreviations are used:

Undesired plants/weeds:

ABUTH: *Abutilon theophrasti*    ALOMY: *Alopecurus myosuroides*
AMARE: *Amaranthus retroflexus*    AVEFA: *Avena fatua*
CYPES: *Cyperus esculentus*    ECHCG: *Echinochloa crus-galli*
LOLMU: *Lolium multiflorum*    MATIN: *Matricaria inodora*
PHBPU: *Ipomoea purpurea*    POLCO: *Polygonum convolvulus*
SETVI: *Setaria viridis*    STEME: *Stellaria media*
VERPE: *Veronica persica*    VIOTR: *Viola tricolor*

TABLE 2

Pre-emergence effectiveness

| Example No. | Application rate [g/ha] | Herbicidal activity with respect to [%] | | | | | | | | |
|---|---|---|---|---|---|---|---|---|---|---|
| | | ALOMY | ECHCG | LOLMU | SETVI | ABUTH | MATIN | POLCO | STEME | VERPE |
| 1.70 | 320 | 100 | 100 | 100 | 100 | 100 | 100 | 100 | 100 | 100 |
| 1.3 | 320 | 100 | 100 | 100 | 100 | 100 | 100 | 100 | 100 | 100 |
| 1.73 | 320 | 100 | 100 | 100 | 100 | 100 | 100 | 100 | 100 | 100 |
| 1.23 | 320 | 100 | 100 | 90 | 100 | 100 | 100 | 100 | 100 | 100 |
| 1.45 | 320 | 100 | 100 | 100 | 100 | 90 | 100 | 100 | 100 | 100 |
| 1.24 | 320 | 100 | 100 | 100 | 100 | 80 | 100 | 100 | 100 | 100 |
| 1.67 | 320 | 100 | 100 | 100 | 100 | 80 | 100 | 100 | 100 | 100 |
| 1.72 | 320 | 100 | 100 | 100 | 100 | 100 | 100 | 100 | 100 | 100 |
| 1.25 | 320 | 100 | 100 | 100 | 100 | 100 | 100 | 100 | 100 | 100 |
| 1.52 | 320 | 100 | 100 | 100 | 100 | 100 | 100 | 100 | 100 | 100 |
| 1.44 | 320 | 100 | 100 | 100 | 100 | 100 | 100 | 100 | 100 | 100 |
| 1.71 | 320 | 100 | 100 | 100 | 100 | 100 | 100 | 100 | 100 | 100 |
| 1.22 | 320 | 100 | 100 | | 100 | 90 | 100 | 100 | 100 | 100 |
| 1.40 | 320 | 100 | 100 | 100 | 100 | 90 | 100 | 100 | 100 | 100 |
| 1.26 | 320 | 100 | 100 | | 100 | 100 | 100 | 100 | 100 | 100 |
| 1.49 | 320 | 100 | 100 | 100 | 100 | | 100 | 100 | 100 | 100 |
| 1.68 | 320 | 100 | 100 | 100 | 100 | 100 | 100 | 100 | 100 | 100 |
| 1.46 | 320 | 90 | 100 | 90 | 100 | | 100 | 100 | 100 | 100 |
| 1.65 | 320 | | 100 | 100 | 100 | 90 | 100 | 100 | 100 | 100 |
| 1.66 | 320 | 80 | 100 | 100 | 100 | 100 | | 100 | 100 | 100 |
| 1.31 | 320 | 100 | 100 | 100 | 100 | | 100 | 100 | 100 | 100 |
| 1.69 | 320 | 90 | 100 | 90 | 100 | | 100 | 100 | 100 | 100 |
| 1.4 | 320 | 100 | 100 | 100 | 100 | | 100 | 100 | 100 | 100 |
| 1.41 | 320 | 100 | 100 | 100 | 100 | | 100 | 100 | 100 | 100 |
| 1.78 | 320 | 100 | 100 | | 100 | 100 | 100 | 90 | | |
| 1.76 | 320 | 100 | 100 | | 100 | 100 | 100 | 100 | | |

TABLE 2-continued

Pre-emergence effectiveness

| Example No. | Application rate [g/ha] | Herbicidal activity with respect to [%] ALOMY | ECHCG | LOLMU | SETVI | ABUTH | MATIN | POLCO | STEME | VERPE |
|---|---|---|---|---|---|---|---|---|---|---|
| 1.37 | 320 | 100 | 100 | 100 | 100 |  | 100 | 100 | 100 | 100 |
| 1.39 | 320 | 80 | 90 |  | 100 |  | 100 | 80 | 100 | 100 |
| 1.74 | 320 | 80 | 100 |  | 100 |  | 100 | 100 |  |  |
| 1.59 | 320 |  | 80 | 90 | 80 |  | 100 | 80 | 100 | 100 |
| 1.47 | 320 | 80 | 100 |  | 100 |  | 100 | 100 | 100 | 100 |
| 1.21 | 320 | 90 | 100 |  | 100 |  | 100 | 100 |  | 80 |
| 1.64 | 320 |  | 100 |  | 100 |  | 90 | 100 | 100 | 100 |
| 1.77 | 320 | 100 | 100 |  | 100 | 90 | 100 | 100 |  |  |

TABLE 3

Pre-emergence effectiveness

| Example No. | Application rate [g/ha] | Herbicidal activity with respect to [%] ECHCG | MATIN | POLCO | STEME | VERPE |
|---|---|---|---|---|---|---|
| 1.32 | 320 | 100 | 100 |  | 100 | 100 |
| 1.33 | 320 | 80 | 100 | 100 | 100 | 100 |
| 1.30 | 320 | 80 | 100 | 100 | 100 | 100 |
| 1.38 | 320 | 80 |  |  | 100 | 100 |
| 1.29 | 320 |  | 100 | 80 | 90 | 90 |
| 1.48 | 320 | 100 | 100 |  | 100 | 100 |
| 1.22 | 320 | 100 | 100 | 100 | 100 | 100 |
| 1.105 | 320 | 100 | 100 | 100 | 100 | 100 |
| 1.26 | 320 | 100 | 100 | 100 | 100 | 100 |
| 1.103 | 320 | 100 | 100 | 100 | 100 | 100 |
| 1.81 | 320 | 100 | 100 | 100 | 100 | 100 |
| 1.31 | 320 | 100 | 100 | 100 | 100 | 100 |
| 1.41 | 320 | 100 | 100 | 100 | 100 | 100 |
| 1.65 | 320 | 100 | 100 | 100 | 100 | 100 |
| 1.66 | 320 | 100 | 100 | 100 | 100 | 100 |
| 1.46 | 320 | 100 | 100 | 100 | 100 | 100 |
| 1.49 | 320 | 100 | 100 | 100 | 100 | 100 |
| 1.37 | 320 | 100 | 100 | 100 | 100 | 100 |
| 1.69 | 320 | 100 | 100 | 100 | 100 | 100 |
| 1.4 | 320 | 100 | 100 | 100 | 100 | 100 |
| 1.39 | 320 | 90 | 100 | 80 | 100 | 100 |
| 1.59 | 320 | 80 | 80 | 80 | 100 | 100 |
| 1.47 | 320 | 100 | 100 | 100 | 100 | 100 |

TABLE 4

Pre-emergence effectiveness

| Example No. | Application rate [g/ha] | Herbicidal activity with respect to [%] ECHCG | SETVI | MATIN | POLCO |
|---|---|---|---|---|---|
| 1.21 | 320 | 100 | 100 | 100 | 100 |
| 1.76 | 320 | 100 | 100 | 100 | 100 |
| 1.77 | 320 | 100 | 100 | 100 | 100 |
| 1.64 | 320 | 100 | 100 | 90 | 100 |
| 1.78 | 320 | 100 | 100 | 100 | 90 |
| 1.82 | 320 |  | 100 | 100 | 100 |
| 1.32 | 320 | 100 | 90 | 100 |  |
| 1.33 | 320 | 80 |  | 100 | 100 |
| 1.30 | 320 | 80 |  | 100 | 100 |
| 1.74 | 320 | 100 | 100 | 100 | 100 |

TABLE 5

Pre-emergence effectiveness

| Example No. | Application rate [g/ha] | Herbicidal activity with respect to [%] MATIN | STEME | VERPE |
|---|---|---|---|---|
| 1.5 | 320 | 90 |  | 100 |
| 1.43 | 320 | 100 | 100 | 100 |
| 1.6 | 320 | 90 |  | 100 |
| 1.53 | 320 |  | 100 | 100 |
| 1.2 | 320 | 90 | 100 | 100 |
| 1.60 | 320 |  | 100 | 100 |
| 1.57 | 320 |  | 100 | 100 |
| 1.55 | 320 |  | 100 | 90 |
| 1.56 | 320 |  | 100 | 100 |
| 1.8 | 320 |  | 80 | 100 |
| 1.42 | 320 |  | 100 | 80 |
| 1.7 | 320 | 90 |  | 100 |

TABLE 6

Pre-emergence effectiveness

| Example No. | Application rate [g/ha] | Herbicidal activity with respect to [%] STEME | VERPE |
|---|---|---|---|
| 1.29 | 320 | 90 | 90 |
| 1.48 | 320 | 100 | 100 |
| 1.5 | 320 |  | 100 |
| 1.53 | 320 | 100 | 100 |
| 1.80 | 320 | 100 | 100 |
| 1.87 | 320 | 100 | 90 |
| 1.60 | 320 | 100 | 100 |
| 1.2 | 320 | 100 | 100 |
| 1.43 | 320 | 100 | 100 |
| 1.6 | 320 |  | 100 |
| 1.79 | 320 | 100 | 100 |
| 1.84 | 320 | 100 | 100 |
| 1.7 | 320 |  | 100 |
| 1.42 | 320 | 100 | 80 |
| 1.8 | 320 | 80 | 100 |
| 1.57 | 320 | 100 | 100 |
| 1.55 | 320 | 100 | 90 |
| 1.56 | 320 | 100 | 100 |
| 1.63 | 320 | 100 |  |
| 1.35 | 320 |  | 100 |
| 1.14 | 320 | 90 |  |
| 1.61 | 320 | 80 |  |
| 1.10 | 320 | 80 |  |

As shown by the results, the compounds of the invention have good herbicidal pre-emergence activity against a broad spectrum of weed grasses and broad-leaved weeds. For example, the compounds of Tables 2 to 6 have very good herbicidal activity against harmful plants such as *Veronica* persicam, Stellaria media and Matricaria inodora in the pre-emergence method at an application rate of 320 g/ha and less of active substance per hectare. The compounds of the invention are therefore suitable for control of unwanted plant growth by the pre-emergence method.

2. Post-Emergence Herbicidal Effect and Crop Plant Compatibility

Seeds of monocotyledonous and dicotyledonous weed and crop plants are laid out in sandy loam soil in wood-fiber pots, covered with soil and cultivated in a greenhouse under good growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants as aqueous suspension or emulsion at a water application rate equating to 600 to 800 L/ha with addition of 0.2% wetting agent. After the test plants have been left to stand in the greenhouse under optimal growth conditions for about 3 weeks, the action of the preparations is assessed visually in comparison to untreated controls (herbicidal action in percent (%): 100% activity=the plants have died, 0% activity=like control plants).

TABLE 7

Post-emergence activity

| Example No. | Application rate [g/ha] | Herbicidal activity with respect to [%] | | | | | |
|---|---|---|---|---|---|---|---|
| | | ALOMY | ECHCG | AMARE | STEME | VIOTR | VERPE |
| 1.23 | 320 | 100 | 100 | 100 | 100 | 100 | 90 |
| 1.67 | 320 | 90 | 100 | 100 | 100 | 100 | 90 |
| 1.3 | 320 | 90 | 80 | 100 | 100 | 100 | 100 |
| 1.73 | 320 | 100 | 100 | 100 | 100 | 90 | 100 |
| 1.52 | 320 | 100 | 100 | 100 | 100 | 90 | 90 |
| 1.25 | 320 | 100 | 100 | 90 | 100 | 90 | 100 |
| 1.22 | 320 | 100 | 100 | 100 | 100 | 100 | 100 |
| 1.71 | 320 | 90 | 100 | 80 | 100 | 90 | 80 |
| 1.70 | 320 | 100 | 100 | 90 | 100 | 90 | 100 |
| 1.24 | 320 | 100 | 100 | 90 | 100 | 100 | 100 |
| 1.72 | 320 | 100 | 100 | 90 | 100 | 90 | 80 |
| 1.47 | 320 | 100 | 100 | 100 | 100 | 100 | 100 |
| 1.21 | 320 | 80 | 80 | 90 | 100 | 80 | 100 |
| 1.44 | 320 | 100 | 90 | 100 | 90 | 90 | 100 |
| 1.45 | 320 | | 100 | 80 | 90 | 90 | 90 |
| 1.68 | 320 | 100 | 80 | | 100 | 90 | 80 |
| 1.69 | 320 | 90 | 80 | 90 | 100 | 80 | 80 |
| 1.26 | 320 | | 100 | 90 | 100 | 100 | 100 |
| 1.78 | 320 | 100 | | 80 | 100 | 80 | |
| 1.49 | 320 | 80 | 80 | 80 | 90 | 90 | 100 |
| 1.76 | 320 | 80 | | 80 | 100 | | |

TABLE 8

Post-emergence activity

| Example No. | Application rate [g/ha] | Herbicidal activity with respect to [%] | | | |
|---|---|---|---|---|---|
| | | AMARE | STEME | VIOTR | VERPE |
| 1.66 | 320 | | 100 | 90 | 100 |
| 1.37 | 320 | | 100 | | 100 |
| 1.64 | 320 | 100 | 90 | 80 | 100 |
| 1.65 | 320 | | 100 | 80 | 80 |
| 1.4 | 320 | 90 | 90 | 80 | 90 |
| 1.32 | 320 | 80 | 80 | | 80 |
| 1.39 | 320 | | 80 | 90 | 100 |
| 1.40 | 320 | | | 80 | 100 |
| 1.41 | 320 | 80 | | 80 | 100 |

TABLE 8-continued

Post-emergence activity

| Example No. | Application rate [g/ha] | Herbicidal activity with respect to [%] | | | |
|---|---|---|---|---|---|
| | | AMARE | STEME | VIOTR | VERPE |
| 1.77 | 320 | | 100 | 90 | |
| 1.60 | 320 | 80 | 90 | | 100 |

TABLE 9

Post-emergence activity

| Example No. | Application rate [g/ha] | Herbicidal activity with respect to [%] | | |
|---|---|---|---|---|
| | | STEME | VIOTR | VERPE |
| 1,103 | 320 | 80 | 90 | 90 |
| 1.65 | 320 | 100 | 80 | 80 |
| 1.37 | 320 | 100 | | 100 |

TABLE 9-continued

Post-emergence activity

| Example No. | Application rate [g/ha] | Herbicidal activity with respect to [%] | | |
|---|---|---|---|---|
| | | STEME | VIOTR | VERPE |
| 1.66 | 320 | 100 | 90 | 100 |
| 1.84 | 320 | | 90 | 80 |
| 1.4 | 320 | 90 | 80 | 90 |
| 1.77 | 320 | 100 | 90 | |
| 1,105 | 320 | | 90 | 80 |
| 1.60 | 320 | 90 | | 100 |
| 1.64 | 320 | 90 | 80 | 100 |
| 1.38 | 320 | | 90 | |
| 1.48 | 320 | 100 | | 80 |
| 1.32 | 320 | 80 | | 80 |
| 1.55 | 320 | | 80 | 80 |

TABLE 9-continued

Post-emergence activity

| Example No. | Application rate [g/ha] | Herbicidal activity with respect to [%] | | |
|---|---|---|---|---|
| | | STEME | VIOTR | VERPE |
| 1.31 | 320 | 90 | | |
| 1.59 | 320 | 100 | | 80 |
| 1.74 | 320 | 100 | | |
| 1.75 | 320 | 100 | | |
| 1.39 | 320 | 80 | 90 | 100 |
| 1.40 | 320 | | 80 | 100 |
| 1.41 | 320 | | 80 | 100 |
| 1.80 | 320 | | 100 | |
| 1.43 | 320 | | 80 | 80 |
| 1.46 | 320 | 100 | | 80 |
| 1,101 | 320 | | | |
| 1.6 | 320 | | 80 | 80 |
| 1.81 | 320 | | 80 | |
| 1.30 | 320 | 80 | | 80 |
| 1.7 | 320 | | | 90 |
| 1.53 | 320 | | | 80 |
| 1.5 | 320 | | | 80 |
| 1.33 | 320 | | | 80 |
| 1.29 | 320 | 90 | 80 | |
| 1.34 | 320 | | | 90 |
| 1.57 | 320 | | | 80 |

TABLE 10

Post-emergence activity

| Example No. | Application rate [g/ha] | Herbicidal activity with respect to [%] | |
|---|---|---|---|
| | | STEME | VERPE |
| 1.74 | 320 | 100 | |
| 1.6 | 320 | | 80 |
| 1.48 | 320 | 100 | 80 |
| 1.46 | 320 | 100 | 80 |
| 1.31 | 320 | 90 | |
| 1.30 | 320 | 80 | 80 |
| 1.29 | 320 | 90 | |
| 1.7 | 320 | | 90 |
| 1.59 | 320 | 100 | 80 |
| 1.5 | 320 | | 80 |
| 1.55 | 320 | | 80 |
| 1.43 | 320 | | 80 |
| 1.33 | 320 | | 80 |
| 1.75 | 320 | 100 | |
| 1.34 | 320 | | 90 |
| 1.53 | 320 | | 80 |
| 1.57 | 320 | | 80 |

As the results show, compounds according to the invention have good herbicidal post-emergence efficacy against a broad spectrum of weed grasses and broad-leaved weeds. For example, the compounds of Tables 7 to 10 have very good herbicidal activity against harmful plants such as *Veronica persicam* and *Stellaria media* in the post-emergence method at an application rate of 320 g/ha and less of active substance per hectare. The compounds of the invention are therefore suitable for control of unwanted plant growth by the post-emergence method.

The invention claimed is:

1. A compound of formula (I)

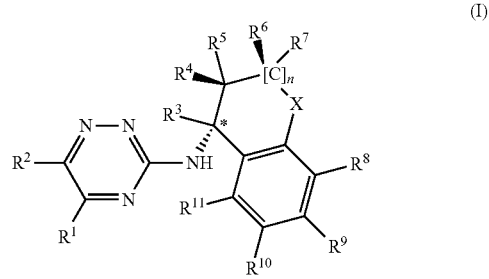

and/or an agrochemically acceptable salt thereof in which
R$^1$ represents hydrogen, amino, hydrazino, hydroxyamino, (($C_1$-$C_6$)-alkyl)-amino, (($C_3$-$C_6$)-cycloalkyl)-amino, di-(($C_1$-$C_6$)-alkyl)-amino, ($C_1$-$C_6$)-alkylcarbonylamino, bis-(($C_1$-$C_6$)-alkyl)-carbonylamino;

R$^2$ is selected from the group consisting of hydrogen, halogen, hydroxy, nitro, amino, cyano, C(O)OH, C(O)NH$_2$; ($C_1$-$C_6$)-alkyl, ($C_1$-$C_6$)-haloalkyl, ($C_1$-$C_6$)-alkylcarbonyl, ($C_1$-$C_6$)-haloalkylcarbonyl, ($C_1$-$C_6$)-alkylcarbonyloxy, ($C_1$-$C_6$)-haloalkylcarbonyloxy, ($C_1$-$C_6$)-alkylcarbonyl-($C_1$-$C_4$)-alkyl; ($C_1$-$C_6$)-alkoxy, ($C_1$-$C_6$)-haloalkoxy, ($C_1$-$C_6$)-alkoxycarbonyl, ($C_1$-$C_6$)-haloalkoxycarbonyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkoxycarbonyl-($C_1$-$C_6$)-haloalkyl, ($C_1$-$C_6$)-haloalkoxycarbonyl-($C_1$-$C_6$)-haloalkyl; ($C_2$-$C_6$)-alkenyl, ($C_2$-$C_6$)-haloalkenyl, ($C_2$-$C_6$)-alkenylcarbonyl, ($C_2$-$C_6$)-haloalkenylcarbonyl, ($C_2$-$C_6$)-alkenyloxy, ($C_2$-$C_6$)-haloalkenyloxy, ($C_2$-$C_6$)-alkenyloxycarbonyl, ($C_2$-$C_6$)-haloalkenyloxycarbonyl; ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl; tri-($C_1$-$C_6$)-alkylsilyl-($C_2$-$C_6$)-alkynyl, di-($C_1$-$C_6$)-alkylsilyl-($C_2$-$C_6$)-alkynyl, ($C_1$-$C_6$)-alkylsilyl-($C_2$-$C_6$)-alkynyl; phenylsilyl-($C_2$-$C_6$)-alkynyl; ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted in the aryl moiety by halogen, ($C_1$-$C_6$)-alkyl and/or ($C_1$-$C_6$)-haloalkyl; ($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy; aminocarbonyl-($C_1$-$C_6$)-alkyl, di-($C_1$-$C_6$)-alkylaminocarbonyl-($C_1$-$C_6$)-alkyl; N—(($C_1$-$C_6$)-haloalkanoyl)aminocarbonyl, (($C_6$-$C_{14}$)-aryl)aminocarbonyl, di-(($C_6$-$C_{14}$)-aryl)aminocarbonyl, (($C_1$-$C_6$)-alkyl)aminocarbonyl, di-(($C_1$-$C_6$)-alkyl)aminocarbonyl, N—(($C_1$-$C_6$)-alkylsulfonyl)aminocarbonyl, N—(($C_1$-$C_6$)-haloalkylsulfonyl)aminocarbonyl, N—(($C_6$-$C_{14}$)-arylsulfonyl)aminocarbonyl; ($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy; ($C_3$-$C_8$)-cycloalkyl which may optionally be substituted in the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)- haloalkylcarbonyl, $(C_3-C_8)$-cycloalkyl-$(C_1-C_6)$-alkoxycarbonyl, $(C_3-C_8)$-cycloalkyl-$(C_1-C_6)$-haloalkoxycarbonyl, $(C_3-C_8)$-cycloalkylcarbonyloxy, $(C_3-C_8)$-cycloalkoxycarbonyloxy, $(C_3-C_8)$-cycloalkyl-$(C_1-C_6)$-alkylcarbonyloxy, $(C_3-C_8)$-cycloalkyl-$(C_1-C_6)$-haloalkylcarbonyloxy, $(C_3-C_8)$-cycloalkyl-$(C_1-C_6)$-alkoxycarbonyloxy, $(C_3-C_8)$-cycloalkyl-$(C_1-C_6)$-haloalkoxycarbonyloxy; $(C_3-C_8)$-cycloalkenyl, $(C_3-C_8)$-cycloalkenyloxy, $(C_3-C_8)$-cycloalkenyl-$(C_1-C_6)$-alkyl, $(C_3-C_8)$-cycloalkenyl-$(C_1-C_6)$-haloalkyl, $(C_3-C_8)$-cycloalkenyl-$(C_1-C_6)$-alkoxy, $(C_3-C_8)$-cycloalkenyl-$(C_1-C_6)$-haloalkoxy, $(C_3-C_8)$-cycloalkenylcarbonyl, $(C_3-C_8)$-cycloalkenyloxycarbonyl, $(C_3-C_8)$-cycloalkenyl-$(C_1-C_6)$-alkylcarbonyl, $(C_3-C_8)$-cycloalkenyl-$(C_1-C_6)$-haloalkylcarbonyl, $(C_3-C_8)$-cycloalkenyl-$(C_1-C_6)$-alkoxycarbonyl, $(C_3-C_8)$-cycloalkenyl-$(C_1-C_6)$-haloalkoxycarbonyl, $(C_3-C_8)$-cycloalkenylcarbonyloxy, $(C_3-C_8)$-cycloalkenyloxycarbonyloxy, $(C_3-C_8)$-cycloalkenyl-$(C_1-C_6)$-alkylcarbonyloxy, $(C_3-C_8)$-cycloalkenyl-$(C_1-C_6)$-haloalkylcarbonyloxy, $(C_3-C_8)$-cycloalkenyl-$(C_1-C_6)$-alkoxycarbonyloxy, $(C_3-C_8)$-cycloalkenyl-$(C_1-C_6)$-haloalkoxycarbonyloxy; hydroxy-$(C_1-C_6)$-alkyl, hydroxy-$(C_1-C_6)$-alkoxy, cyano-$(C_1-C_6)$-alkoxy, cyano-$(C_1-C_6)$-alkyl; and $(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylthio, $(C_1-C_6)$-haloalkylsulfinyl, $(C_1-C_6)$-alkylsulfonyl-$(C_1-C_6)$-alkyl, $(C_1-C_6)$-alkylthio-$(C_1-C_6)$-alkyl, $(C_1-C_6)$-alkylsulfinyl-$(C_1-C_6)$-alkyl, $(C_1-C_6)$-haloalkylsulfonyl-$(C_1-C_6)$-alkyl, $(C_1-C_6)$-haloalkylthio-$(C_1-C_6)$-alkyl, $(C_1-C_6)$-haloalkylsulfinyl-$(C_1-C_6)$-alkyl, $(C_1-C_6)$-alkylsulfonyl-$(C_1-C_6)$-haloalkyl, $(C_1-C_6)$-alkylthio-$(C_1-C_6)$-haloalkyl, $(C_1-C_6)$-alkylsulfinyl-$(C_1-C_6)$-haloalkyl, $(C_1-C_6)$-haloalkylsulfonyl-$(C_1-C_6)$-haloalkyl, $(C_1-C_6)$-haloalkylthio-$(C_1-C_6)$-haloalkyl, $(C_1-C_6)$-haloalkylsulfinyl-$(C_1-C_6)$-haloalkyl, $(C_1-C_6)$-alkylsulfonyloxy, $(C_1-C_6)$-haloalkylsulfonyloxy, $(C_1-C_6)$-alkylthiocarbonyl, $(C_1-C_6)$-haloalkylthiocarbonyl, $(C_1-C_6)$-alkylthiocarbonyloxy, $(C_1-C_6)$-haloalkylthiocarbonyloxy, $(C_1-C_6)$-alkylthio-$(C_1-C_6)$-alkyl, $(C_1-C_6)$-alkylthio-$(C_1-C_6)$-alkoxy, $(C_1-C_6)$-alkylthio-$(C_1-C_6)$-alkylcarbonyl, $(C_1-C_6)$-alkylthio-$(C_1-C_6)$-alkylcarbonyloxy; $(C_4-C_{14})$-arylsulfonyl, $(C_6-C_{14})$-arylthio, $(C_6-C_{14})$-arylsulfinyl, $(C_3-C_8)$-cycloalkylthio, $(C_3-C_8)$-alkenylthio, $(C_3-C_8)$-cycloalkenylthio and $(C_3-C_6)$-alkynylthio; or $R^1$ may be attached to $R^2$ via a bond, resulting in a 5- to 7-membered partially hydrogenated carbocycle or heterocycle having at least one heteroatom selected from the group consisting of N, O, S and P, which carbocycle or heterocycle is optionally substituted by one or more substituents selected from the group consisting of hydroxy, =O, =N—O—H, =N—O—$(C_1-C_6)$-alkyl, =N—O-benzyl, =N—O-phenyl, phenyl, phenyl substituted by one or more identical or different halogen atoms, $(C_1-C_6)$-alkyl, $(C_3-C_6)$-cycloalkyl and $(C_1-C_6)$-haloalkyl;

$R^3$ is selected from the group consisting of hydrogen, $(C_1-C_6)$-alkyl, $(C_1-C_6)$-alkoxy, $(C_1-C_6)$-alkoxy-$(C_1-C_6)$-alkyl, $(C_1-C_6)$-alkoxycarbonyl and aminocarbonyl;

$R^4$ and $R^5$ are each independently of one another selected from the group consisting of hydrogen, $(C_1-C_6)$-alkyl, $(C_1-C_6)$-haloalkyl, hydroxy, $(C_1-C_6)$-alkoxy and $(C_1-C_6)$-haloalkoxy; or $R^4$ and $R^5$ together with the carbon atom to which they are attached form a saturated three- to seven-membered ring which may contain one or more heteroatoms selected from the group consisting of oxygen, sulfur and nitrogen;

$R^6$ and $R^7$ are each independently of one another selected from the group consisting of hydrogen, $(C_1-C_6)$-alkyl, $(C_1-C_6)$-haloalkyl, $(C_1-C_6)$-alkoxy, $(C_1-C_6)$-haloalkoxy, $(C_6-C_{14})$-aryl, $(C_6-C_{14})$-aryloxy, $(C_6-C_{14})$-arylcarbonyl and $(C_6-C_{14})$-aryloxycarbonyl; or the $R^6$ and $R^7$ radicals together form a $(C_1-C_7)$-alkylene group which may contain one or more oxygen and/or sulfur atoms, where the $(C_1-C_7)$-alkylene group may be mono- or polysubstituted by halogen and the respective halogen substituents may be identical or different;

n is 0, 1 or 2;

$R^8$, $R^9$, $R^{10}$ and $R^{11}$ are each independently of one another selected from the group consisting of hydrogen, halogen, cyano, C(O)OH, C(O)NH$_2$, $(C_1-C_6)$-alkyl, $(C_1-C_6)$-alkylcarbonyl, $(C_1-C_6)$-alkyloxycarbonyl, $(C_1-C_6)$-alkylaminocarbonyl, $(C_1-C_6)$-dialkylaminocarbonyl, $(C_1-C_6)$-haloalkyl, $(C_1-C_6)$-alkoxy, $(C_1-C_6)$-haloalkoxy, $(C_2-C_6)$-alkenyl, $(C_2-C_6)$-alkynyl, $(C_2-C_6)$-haloalkynyl, $(C_2-C_6)$-alkynylcarbonyl, $(C_2-C_6)$-haloalkynylcarbonyl, $(C_2-C_6)$-alkynyloxy, $(C_2-C_6)$-haloalkynyloxy, $(C_2-C_6)$-alkynyloxycarbonyl, $(C_2-C_6)$-haloalkynyloxycarbonyl and nitro, where the $R^9$ and $R^{10}$ radicals may be attached to one another via an —O—CH$_2$—O— group forming a ring;

X represents a bond, CH$_2$, O, S, carbonyl, NH, CR$^{12}$R$^{13}$, NR$^{14}$, CH$_2$O or CH$_2$S, where in the two last-mentioned groups the carbon atom is attached to the aromatic moiety and the heteroatom O or S is attached to the partially hydrogenated moiety of the amine;

$R^{12}$ and $R^{13}$ are each independently of one another selected from the group consisting of hydrogen, $(C_1-C_6)$-alkyl and $(C_1-C_6)$-haloalkyl; and $R^{14}$ is selected from the group consisting of hydrogen, $(C_1-C_6)$-alkyl and $(C_1-C_6)$-haloalkyl.

2. The compound of formula (I) and/or salt as claimed in claim 1, wherein $R^1$ is selected from the group consisting of hydrogen, amino, ((C$_1$-C$_6$)-alkyl)amino, ((C$_3$-C$_6$)-cycloalkyl)amino and di-((C$_1$-C$_6$)-alkyl)amino.

3. The compound of formula (I) and/or salt as claimed in claim 1, wherein
$R^2$ is selected from the group consisting of hydrogen, halogen, hydroxy, nitro, amino, cyano, C(O)OH, C(O)NH$_2$; $(C_1-C_6)$-alkyl, $(C_1-C_6)$-haloalkyl; $(C_1-C_6)$-alkylcarbonyl, $(C_1-C_6)$-haloalkylcarbonyl, $(C_1-C_6)$-alkoxycarbonyl, $(C_1-C_6)$-haloalkoxycarbonyl; $(C_2-C_6)$-alkenyl, $(C_2-C_6)$-haloalkenyl; $(C_2-C_6)$-alkynyl, $(C_2-C_6)$-haloalkynyl; $(C_6-C_{14})$-aryl which may be substituted in the aryl moiety by halogen, $(C_1-C_6)$-alkyl and/or $(C_1-C_6)$-haloalkyl; $(C_1-C_6)$-alkoxy-$(C_1-C_6)$-alkyl, hydroxy-$(C_1-C_6)$-alkyl; ((C$_1$-C$_6$)-alkyl)aminocarbonyl, di-((C$_1$-C$_6$)-alkyl)aminocarbonyl, N—((C$_1$-C$_6$)-alkylsulfonyl)aminocarbonyl, N—((C$_1$-C$_6$)-haloalkylsulfonyl)aminocarbonyl, $(C_3-C_8)$-cycloalkylcarbonyl, $(C_3-C_8)$-cycloalkoxycarbonyl; $(C_1-C_6)$-alkylsulfonyl, $(C_1-C_6)$-alkylthio, $(C_1-C_6)$-alkylsulfinyl, $(C_1-C_6)$-haloalkylsulfonyl, $(C_1-C_6)$-haloalkylsulfinyl, $(C_4-C_{14})$-arylsulfonyl and $(C_6-C_{14})$-arylsulfinyl.

4. The compound of formula (I) and/or salt as claimed in claim 1, wherein $R^3$ represents hydrogen.

5. The compound of formula (I) and/or salt as claimed in claim 1, wherein $R^4$ and $R^5$ together with the carbon atom to which they are attached form a saturated three- to seven-membered ring which may contain an oxygen atom.

6. The compound of formula (I) and/or salt as claimed in claim 1, wherein $R^6$ and $R^7$ are independently of one another selected from the group consisting of hydrogen, $(C_1-C_6)$-alkyl and $(C_6-C_{14})$-aryl.

7. The compound of formula (I) and/or salt as claimed in claim 1, wherein $R^9$ is selected from the group consisting of hydrogen, halogen, $(C_1-C_6)$-alkyl and $(C_1-C_6)$-alkoxy.

8. The compound of formula (I) and/or salt as claimed in claim 1, wherein $R^{11}$ is selected from the group consisting of hydrogen and $(C_1-C_6)$-alkyl.

9. The compound of formula (I) and/or salt as claimed in claim 1, wherein X is selected from the group consisting of a chemical bond, $CH_2$, O, S, carbonyl, NH, $CH(C_1-C_6)$-alkyl, $N(C_1-C_6)$-alkyl, $OCH_2$ and $SCH_2$, where in the two last-mentioned groups the carbon atom is attached to the aromatic moiety and the heteroatom O or S is attached to the partially hydrogenated moiety of the amine.

10. The compound of formula (I) and/or salt as claimed in claim 1, wherein n is 0 or 1.

11. The compound of formula (I) and/or salt

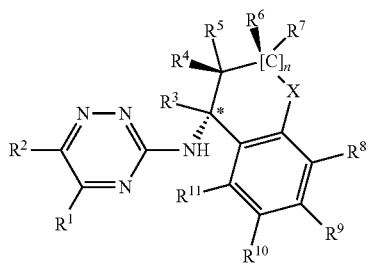
(I)

as claimed in claim 1, wherein the chiral carbon atom marked by (*) has an (R) configuration.

12. The compound of formula (I) and/or salt

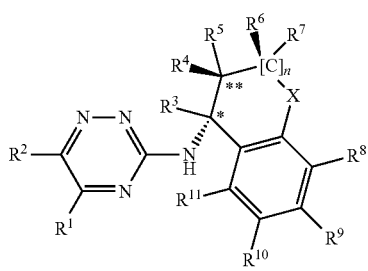
(I)

as claimed in claim 1, wherein the chiral carbon atom marked by (*) has an (R) configuration and the chiral carbon atom marked by (**) has an (S) configuration.

13. A process for preparing one or more compounds of formula (I) and/or agrochemically acceptable salts thereof as claimed in claim 1, said process comprising reacting a compound of formula (II)

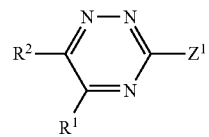
(II)

where $Z^1$ represents an exchangeable radical or a leaving group selected from the group consisting of fluorine, chlorine, bromine, iodine, $(C_1-C_4)$-alkylsulfanyl, $(C_1-C_4)$-alkylsulfinyl, $(C_1-C_4)$-alkylsulfonyl, unsubstituted phenyl-$(C_1-C_4)$-alkylsulfonyl or phenyl-$(C_1-C_4)$-alkylsulfonyl which is mono- or polysubstituted by fluorine, chlorine, bromine or $(C_1-C_4)$-alkyl or $(C_1-C_4)$-alkoxy and represents $(C_1-C_4)$-alkylphenylsulfonyl;

with an amine of formula (III) or an acid addition salt of the amine of formula (III)

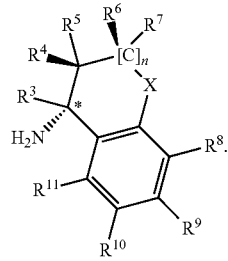
(III)

14. A process for preparing one or more compounds of formula (I):

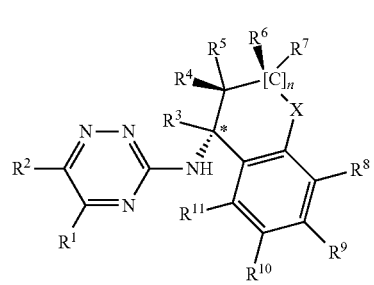
(I)

in which
$R^1$ represents hydrogen, amino, hydrazino, hydroxyamino, $((C_1-C_6)$-alkyl)-amino, $((C_3-C_6)$-cycloalkyl)-amino, di-$((C_1-C_6)$-alkyl)-amino, $(C_1-C_6)$-alkylcarbonylamino, bis-$((C_1-C_6)$-alkyl)-carbonylamino;
$R^2$ is selected from the group consisting of hydrogen, halogen, hydroxy, nitro, amino, cyano, C(O)OH, $C(O)NH_2$; $(C_1-C_6)$-alkyl, $(C_1-C_6)$-haloalkyl, $(C_1-C_6)$-alkylcarbonyl, $(C_1-C_6)$-haloalkylcarbonyl, $(C_1-C_6)$-alkylcarbonyloxy, $(C_1-C_6)$-haloalkylcarbonyloxy, $(C_1-C_6)$-alkylcarbonyl-$(C_1-C_4)$-alkyl; $(C_1-C_6)$-alkoxy, $(C_1-C_6)$-haloalkoxy, $(C_1-C_6)$-alkoxycarbonyl, $(C_1-C_6)$-haloalkoxycarbonyl, $(C_1-C_6)$-alkoxycarbonyl-$(C_1-C_6)$-alkyl, $(C_1-C_6)$-haloalkoxycarbonyl-$(C_1-C_6)$-alkyl, $(C_1-C_6)$-alkoxycarbonyl-$(C_1-C_6)$-haloalkyl, $(C_1-C_6)$-haloalkoxycarbonyl-$(C_1-C_6)$-haloalkyl; $(C_2-C_6)$-alkenyl, $(C_2-C_6)$-haloalkenyl, $(C_2-C_6)$-alkenylcarbonyl, $(C_2-C_6)$-haloalkenylcarbonyl, $(C_2-C_6)$-alkenyloxy, $(C_2-C_6)$-haloalkenyloxy, ($C_2$-$C_6$)-alkenyloxycarbonyl, ($C_2$-$C_6$)-haloalkenyloxycarbonyl; ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl; tri-($C_1$-$C_6$)-alkylsilyl-($C_2$-$C_6$)-alkynyl, di-($C_1$-$C_6$)-alkylsilyl-($C_2$-$C_6$)-alkynyl, ($C_1$-$C_6$)-alkylsilyl-($C_2$-$C_6$)-alkynyl; phenylsilyl-($C_2$-$C_6$)-alkynyl; ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl, each of which may be substituted in the aryl moiety by halogen, ($C_1$-$C_6$)-alkyl and/or ($C_1$-$C_6$)-haloalkyl; ($C_6$-$C_{14}$)-aryl-($C_1$-$C_6$)-alkyl, ($C_6$-$C_{14}$)-aryl-($C_1$-$C_6$)-alkoxy, ($C_6$-$C_{14}$)-aryl-($C_1$-$C_6$)-alkylcarbonyl, ($C_6$-$C_{14}$)-aryl-($C_1$-$C_6$)-alkylcarbonyloxy, ($C_6$-$C_{14}$)-aryl-($C_1$-$C_6$)-alkoxycarbonyl, ($C_6$-$C_{14}$)-aryl-($C_1$-$C_6$)-alkoxycarbonyloxy; aminocarbonyl-($C_1$-$C_6$)-alkyl, di-($C_1$-$C_6$)-alkylaminocarbonyl-($C_1$-$C_6$)-alkyl; N—(($C_1$-$C_6$)-haloalkanoyl)aminocarbonyl, (($C_6$-$C_{14}$)-aryl)aminocarbonyl, di-(($C_6$-$C_{14}$)-aryl)aminocarbonyl, (($C_1$-$C_6$)-alkyl)aminocarbonyl, di-(($C_1$-$C_6$)-alkyl)aminocarbonyl, N—(($C_1$-$C_6$)-alkylsulfonyl)aminocarbonyl, N—(($C_1$-$C_6$)-haloalkylsulfonyl)aminocarbonyl, N—(($C_6$-$C_{14}$)-arylsulfonyl)aminocarbonyl; ($C_1$-$C_6$)-alkoxy-($C_1$-$C_6$)-alkyl, ($C_1$-$C_6$)-alkoxy-($C_1$-$C_6$)-alkoxy, ($C_1$-$C_6$)-alkoxycarbonyl-($C_1$-$C_6$)-alkoxy; ($C_3$-$C_8$)-cycloalkyl which may optionally be substituted in the cycloalkyl radical by ($C_1$-$C_6$)-alkyl and/or halogen; ($C_3$-$C_8$)-cycloalkoxy, ($C_3$-$C_8$)-cycloalkyl-($C_1$-$C_6$)-alkyl, ($C_3$-$C_8$)-cycloalkyl-($C_1$-$C_6$)-haloalkyl, ($C_3$-$C_8$)-cycloalkyl-($C_1$-$C_6$)-alkoxy, ($C_3$-$C_8$)-cycloalkyl-($C_1$-$C_6$)-haloalkoxy, ($C_3$-$C_8$)-cycloalkylcarbonyl, ($C_3$-$C_8$)-cycloalkoxycarbonyl, ($C_3$-$C_8$)-cycloalkyl-($C_1$-$C_6$)-alkylcarbonyl, ($C_3$-$C_8$)-cycloalkyl-($C_1$-$C_6$)-haloalkylcarbonyl, ($C_3$-$C_8$)-cycloalkyl-($C_1$-$C_6$)-alkoxycarbonyl, ($C_3$-$C_8$)-cycloalkyl-($C_1$-$C_6$)-haloalkoxycarbonyl, ($C_3$-$C_8$)-cycloalkylcarbonyloxy, ($C_3$-$C_8$)-cycloalkoxycarbonyloxy, ($C_3$-$C_8$)-cycloalkyl-($C_1$-$C_6$)-alkylcarbonyloxy, ($C_3$-$C_8$)-cycloalkyl-($C_1$-$C_6$)-haloalkylcarbonyloxy, ($C_3$-$C_8$)-cycloalkyl-($C_1$-$C_6$)-alkoxycarbonyloxy, ($C_3$-$C_8$)-cycloalkyl-($C_1$-$C_6$)-haloalkoxycarbonyloxy; ($C_3$-$C_8$)-cycloalkenyl, ($C_3$-$C_8$)-cycloalkenyloxy, ($C_3$-$C_8$)-cycloalkenyl-($C_1$-$C_6$)-alkyl, ($C_3$-$C_8$)-cycloalkenyl-($C_1$-$C_6$)-haloalkyl, ($C_3$-$C_8$)-cycloalkenyl-($C_1$-$C_6$)-alkoxy, ($C_3$-$C_8$)-cycloalkenyl-($C_1$-$C_6$)-haloalkoxy, ($C_3$-$C_8$)-cycloalkenylcarbonyl, ($C_3$-$C_8$)-cycloalkenyloxycarbonyl, ($C_3$-$C_8$)-cycloalkenyl-($C_1$-$C_6$)-alkylcarbonyl, ($C_3$-$C_8$)-cycloalkenyl-($C_1$-$C_6$)-haloalkylcarbonyl, ($C_3$-$C_8$)-cycloalkenyl-($C_1$-$C_6$)-alkoxycarbonyl, ($C_3$-$C_8$)-cycloalkenyl-($C_1$-$C_6$)-haloalkoxycarbonyl, ($C_3$-$C_8$)-cycloalkenylcarbonyloxy, ($C_3$-$C_8$)-cycloalkenyloxycarbonyloxy, ($C_3$-$C_8$)-cycloalkenyl-($C_1$-$C_6$)-alkylcarbonyloxy, ($C_3$-$C_8$)-cycloalkenyl-($C_1$-$C_6$)-haloalkylcarbonyloxy, ($C_3$-$C_8$)-cycloalkenyl-($C_1$-$C_6$)-alkoxycarbonyloxy, ($C_3$-$C_8$)-cycloalkenyl-($C_1$-$C_6$)-haloalkoxycarbonyloxy; hydroxy-($C_1$-$C_6$)-alkyl, hydroxy-($C_1$-$C_6$)-alkoxy, cyano-($C_1$-$C_6$)-alkoxy, cyano-($C_1$-$C_6$)-alkyl; and ($C_1$-$C_6$)-alkylsulfonyl, ($C_1$-$C_6$)-alkylthio, ($C_1$-$C_6$)-alkylsulfinyl, ($C_1$-$C_6$)-haloalkylsulfonyl, ($C_1$-$C_6$)-haloalkylthio, ($C_1$-$C_6$)-haloalkylsulfinyl, ($C_1$-$C_6$)-alkylsulfonyl-($C_1$-$C_6$)-alkyl, ($C_1$-$C_6$)-alkylthio-($C_1$-$C_6$)-alkyl, ($C_1$-$C_6$)-alkylsulfinyl-($C_1$-$C_6$)-alkyl, ($C_1$-$C_6$)-haloalkylsulfonyl-($C_1$-$C_6$)-alkyl, ($C_1$-$C_6$)-haloalkylthio-($C_1$-$C_6$)-alkyl, ($C_1$-$C_6$)-haloalkylsulfinyl-($C_1$-$C_6$)-alkyl, ($C_1$-$C_6$)-alkylsulfonyl-($C_1$-$C_6$)-haloalkyl, ($C_1$-$C_6$)-alkylthio-($C_1$-$C_6$)-haloalkyl, ($C_1$-$C_6$)-alkylsulfinyl-($C_1$-$C_6$)-haloalkyl, ($C_1$-$C_6$)-haloalkylsulfonyl-($C_1$-$C_6$)-haloalkyl, ($C_1$-$C_6$)-haloalkylthio-($C_1$-$C_6$)-haloalkyl, ($C_1$-$C_6$)-haloalkylsulfinyl-($C_1$-$C_6$)-haloalkyl, ($C_1$-$C_6$)-alkylsulfonyloxy, ($C_1$-$C_6$)-haloalkylsulfonyloxy, ($C_1$-$C_6$)-alkylthiocarbonyl, ($C_1$-$C_6$)-haloalkylthiocarbonyl, ($C_1$-$C_6$)-alkylthiocarbonyloxy, ($C_1$-$C_6$)-haloalkylthiocarbonyloxy, ($C_1$-$C_6$)-alkylthio-($C_1$-$C_6$)-alkyl, ($C_1$-$C_6$)-alkylthio-($C_1$-$C_6$)-alkoxy, ($C_1$-$C_6$)-alkylthio-($C_1$-$C_6$)-alkylcarbonyl, ($C_1$-$C_6$)-alkylthio-($C_1$-$C_6$)-alkylcarbonyloxy; ($C_4$-$C_{14}$)-arylsulfonyl, ($C_6$-$C_{14}$)-arylthio, ($C_6$-$C_{14}$)-arylsulfinyl, ($C_3$-$C_8$)-cycloalkylthio, ($C_3$-$C_8$)-alkenylthio, ($C_3$-$C_8$)-cycloalkenylthio and ($C_3$-$C_6$)-alkynylthio; or $R^1$ may be attached to $R^2$ via a bond, resulting in a 5- to 7-membered partially hydrogenated carbocycle or heterocycle having at least one heteroatom selected from the group consisting of N, O, S and P, which carbocycle or heterocycle is optionally substituted by one or more substituents selected from the group consisting of hydroxy, =O, =N—O—H, =N—O—($C_1$-$C_6$)-alkyl, =N—O-benzyl, =N—O-phenyl, phenyl, phenyl substituted by one or more identical or different halogen atoms, ($C_1$-$C_6$)-alkyl, ($C_3$-$C_6$)-cycloalkyl and ($C_1$-$C_6$)-haloalkyl;

$R^3$ is selected from the group consisting of hydrogen, ($C_1$-$C_6$)-alkyl, ($C_1$-$C_6$)-alkoxy, ($C_1$-$C_6$)-alkoxy-($C_1$-$C_6$)-alkyl, ($C_1$-$C_6$)-alkoxycarbonyl and aminocarbonyl;

$R^4$ and $R^5$ are each independently of one another selected from the group consisting of hydrogen, ($C_1$-$C_6$)-alkyl, ($C_1$-$C_6$)-haloalkyl, hydroxy, ($C_1$-$C_6$)-alkoxy and ($C_1$-$C_6$)-haloalkoxy; or $R^4$ and $R^5$ together with the carbon atom to which they are attached form a saturated three- to seven-membered ring which may contain one or more heteroatoms selected from the group consisting of oxygen, sulfur and nitrogen;

$R^6$ and $R^7$ are each independently of one another selected from the group consisting of hydrogen, ($C_1$-$C_6$)-alkyl, ($C_1$-$C_6$)-haloalkyl, ($C_1$-$C_6$)-alkoxy, ($C_1$-$C_6$)-haloalkoxy, ($C_6$-$C_{14}$)-aryl, ($C_6$-$C_{14}$)-aryloxy, ($C_6$-$C_{14}$)-arylcarbonyl and ($C_6$-$C_{14}$)-aryloxycarbonyl; or the $R^6$ and $R^7$ radicals together form a ($C_1$-$C_7$)-alkylene group which may contain one or more oxygen and/or sulfur atoms, where the ($C_1$-$C_7$)-alkylene group may be mono- or polysubstituted by halogen and the respective halogen substituents may be identical or different;

n is 0, 1 or 2;

$R^8$, $R^9$, $R^{10}$ and $R^{11}$ are each independently of one another selected from the group consisting of hydrogen, halogen, cyano, C(O)OH, C(O)NH$_2$, ($C_1$-$C_6$)-alkyl, ($C_1$-$C_6$)-alkylcarbonyl, ($C_1$-$C_6$)-alkyloxycarbonyl, ($C_1$-$C_6$)-alkylaminocarbonyl, ($C_1$-$C_6$)-dialkylaminocarbonyl, ($C_1$-$C_6$)-haloalkyl, ($C_1$-$C_6$)-alkoxy, ($C_1$-$C_6$)-haloalkoxy, ($C_2$-$C_6$)-alkenyl, ($C_2$-$C_6$)-alkynyl, ($C_2$-$C_6$)-haloalkynyl, ($C_2$-$C_6$)-alkynylcarbonyl, ($C_2$-$C_6$)-haloalkynylcarbonyl, ($C_2$-$C_6$)-alkynyloxy, ($C_2$-$C_6$)-haloalkynyloxy, ($C_2$-$C_6$)-alkynyloxycarbonyl, ($C_2$-$C_6$)-haloalkynyloxycarbonyl and nitro, where the $R^9$ and $R^{10}$ radicals may be attached to one another via an —O—CH$_2$—O— group forming a ring;

X represents a bond, CH$_2$, O, S, carbonyl, NH, CR$^{12}$R$^{13}$, NR$^{14}$, CH$_2$O or CH$_2$S, where in the two last-mentioned groups the carbon atom is attached to the aromatic moiety and the heteroatom O or S is attached to the partially hydrogenated moiety of the amine;

$R^{12}$ and $R^{13}$ are each independently of one another selected from the group consisting of hydrogen, ($C_1$-$C_6$)-alkyl and ($C_1$-$C_6$)-haloalkyl; and $R^{14}$ is selected from the group consisting of hydrogen, ($C_1$-$C_6$)-alkyl and ($C_1$-$C_6$)-haloalkyl, and where a compound of formula (II-a)

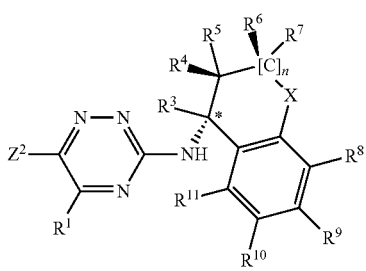

(II-a)

where $Z^2$ is selected from the group consisting of halogen, cyano, $(C_1-C_6)$-alkoxycarbonyl, $(C_1-C_6)$-alkylcarbonyl and $(C_1-C_6)$-alkylthio is prepared by the process as claimed in claim 13 and subsequently the $Z^2$ radical is converted into an $R^2$ radical.

15. A process for preparing one or more compounds of formula (I) and/or agrochemically acceptable salts thereof of claim 1, in which $R^1$ represents amino, and where a guanidine compound of formula (IV) or an acid addition salt thereof

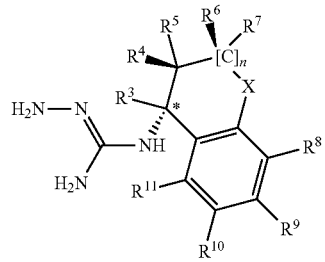

(IV)

is condensed with one or more acylcyanides of formula (V)

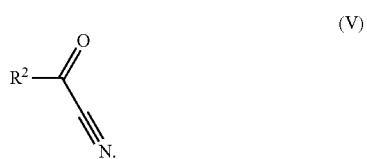

(V)

16. A herbicidal composition or plant growth-regulating composition, comprising one or more compounds of formula (I) or salts thereof as claimed in claim 1.

17. A method of controlling one or more harmful plants and/or of regulating growth of one or more plants, comprising applying an effective amount of one or more compounds of formula (I) or salts thereof as claimed in claim 1 to one or more plants, plant parts, plant seeds and/or an area under cultivation.

18. The method as claimed in claim 17, wherein the one or more plants are crops of useful plants or ornamental plants.

19. The method as claimed in claim 18, wherein the one or more crop plants are transgenic crop plants.

20. The compound of formula (I) and/or salt according to claim 12, wherein $R^1$ represents amino;
$R^2$ represents $CF_3$;
$R^3$ represents hydrogen;
$R^4$ represents methyl;
$R^5$ represents hydrogen;
$R^6$ represents hydrogen;
$R^7$ represents hydrogen;
$R^8$ represents hydrogen;
$R^9$ represents hydrogen;
$R^{10}$ represents methyl;
$R^{11}$ represents hydrogen;
n is 1; and
X represents a bond.

\* \* \* \* \*